United States Patent [19]

Carr et al.

[11] Patent Number: 5,733,882
[45] Date of Patent: Mar. 31, 1998

[54] RETROVIRAL PROTEASE INHIBITORS

[75] Inventors: Thomas Joseph Carr, Phoenixville; Peter Lawrence DeMarsh, Downingtown; Geoffrey Bainbridge Dreyer, Malvern; Ashley Edward Fenwick, Radnor, all of Pa.

[73] Assignee: SmithKline Beecham Corporation, Philadelphia, Pa.

[21] Appl. No.: 396,356

[22] Filed: Feb. 28, 1995

Related U.S. Application Data

[63] Continuation of Ser. No. 193,026, Jan. 17, 1994, abandoned.

[51] Int. Cl.$^6$ .................... C07D 233/64; A61K 31/415
[52] U.S. Cl. .................... 514/19; 514/365; 514/370; 514/377; 514/342; 514/397; 514/398; 514/400; 546/175; 546/278; 548/193; 548/194; 548/200; 548/204; 548/233; 548/236; 548/312.7; 548/315.1; 548/328.5; 548/332.5; 548/335.5; 548/338.1; 548/338.5
[58] Field of Search .................... 548/103, 104, 548/200, 204, 233, 236, 312.7, 315.1, 328.5, 332.5, 335.5, 338.1, 338.5; 514/365, 370, 377, 392, 397, 398, 400; 546/175, 278

[56] References Cited

U.S. PATENT DOCUMENTS

| 4,431,653 | 2/1984 | Wei et al. | 514/19 |
| 4,661,473 | 4/1987 | Boger et al. | 514/19 |
| 4,713,445 | 12/1987 | Szelke et al. | 514/19 |
| 4,812,442 | 3/1989 | Boger et al. | 514/19 |
| 5,142,056 | 8/1992 | Kempe et al. | 514/19 |

FOREIGN PATENT DOCUMENTS

| 0 356 223 | 8/1989 | European Pat. Off. . |
| 0 337 714 | 10/1989 | European Pat. Off. . |
| 0 342 541 A2 | 11/1989 | European Pat. Off. . |
| 0 357 332 A2 | 3/1990 | European Pat. Off. . |
| 0 434 365 A2 | 6/1991 | European Pat. Off. . |
| 0 486 948 A2 | 5/1992 | European Pat. Off. . |
| 0 487 270 A2 | 5/1992 | European Pat. Off. . |
| 0 528 661 A2 | 2/1993 | European Pat. Off. . |
| 0 534 511 A1 | 3/1993 | European Pat. Off. . |
| 0 539 192 A1 | 4/1993 | European Pat. Off. . |
| 0 541 168 A1 | 5/1993 | European Pat. Off. . |
| 0 550 924 A1 | 7/1993 | European Pat. Off. . |

OTHER PUBLICATIONS

Young et al., J. Med. Chem., 35, 1992, pp. 1702–1709.
Thaisrivongs et al., J. Med. Chem. 1991, 34 pp. 2344–2356.
deSolms et al., J. Med. Chem., 1991, 34, pp. 2852–2857.
Roberts et al., Science, 248, 1990, pp. 358–361.
Sham et al., J. Chem. Soc., Chem. Commun., 1991, pp. 110–112.
Green, Protective Groups in Org. Sym. pp. 335–338, 366.67 (1991).

*Primary Examiner*—Robert Gerstl
*Attorney, Agent, or Firm*—Charles M. Kinzig; Edward T. Lentz

[57] ABSTRACT

The present invention provides compounds, more particularly dipeptide analogs, which bind to retroviral proteases. These compounds are inhibitors of retroviral proteases and are useful for treating diseases related to infection by retroviruses.

18 Claims, No Drawings

RETROVIRAL PROTEASE INHIBITORS

This is a continuation of application Ser. No. 08/193,026, filed Jan. 17, 1994 now abandoned.

BACKGROUND OF THE INVENTION

The present invention relates to retroviral protease inhibitor compounds, pharmaceutical compositions thereof, and a method of treating retroviral diseases therewith, including a method of treating disease states associated with human immunodeficiency virus (HIV-1, HIV-2).

Retroviruses, that is, viruses within the family of Retroviridae, are a class of viruses which transport their genetic material as ribonucleic acid rather than deoxyribonucleic acid. Also known as RNA-tumor viruses, their presence has been associated with a wide range of diseases in humans and animals. They are believed to be the causative agents in pathological states associated with infection by Rous sarcoma virus (RSV), murine leukemia virus (MLV), mouse mammary tumor virus (MMTV), feline leukemia virus (FeLV), bovine leukemia virus (BLV), Mason-Pfizer monkey virus (MPMV), simian sarcoma virus (SSV), simian acquired immunodeficiency syndrome (SAIDS), human T-lymphotropic virus (HTLV-I, -II) and human immunodeficiency virus (HIV-1, HIV-2), which is the etiologic agent of AIDS (acquired immunodeficiency syndrome) and AIDS related complexes, and many others. Although the pathogens have, in many of these cases, been isolated, no effective method for treating this type of infection has been developed.

Retroviral replication occurs only in host cells. Critical to this replication is the production of functional viral proteins. Protein synthesis is accomplished by translation of the appropriate open reading frames into polyprotein constructs, which are processed, at least in part, by a viral protease into the functional proteins. The proteolytic activity provided by the viral protease in processing the polyproteins cannot be provided by the host and is essential to the life cycle of the retrovirus. In fact, it has been demonstrated that retroviruses which lack the protease or contain a mutated form of it, lack infectivity. See Katoh et al., *Virology*, 145, 280–92 (1985), Crawford, et al., *J. Virol.*, 53, 899–907(1985) and Debouk, et al., *Proc. Natl. Acad. Sci. USA*, 84, 8903–6(1987). Inhibition of retroviral protease, therefore, presents a method of therapy for retroviral disease.

The use of isosteric replacements has been disclosed as a strategy for the development of protease inhibitors for HIV-1. European Patent Applications EP-A 337 714, EP-A 357 332, EP-A 346 847, EP-A 342 541, EP-A 352 000, EP-A 393 445 and EP-A 434 365 are representative, and are incorporated herein by reference. These references disclose dipeptide analogs of the natural polyprotein substrates of retroviral proteases. As discussed therein, these dipeptide analogs bind selectively and competitively to retroviral proteases; however, the protease is unable to cleave the carbon-carbon bond presented to it instead of the scissile amide bond of the natural substrate. Thus, such compounds are useful for inhibiting viral replication by inactivation of the protease. The incorporation of heterocyclic elements in the P3' and P4' substrate positions of compounds containing a dipeptide isostere has been disclosed by deSolms et al., *J. Med. Chem.*, 34, 2852 (1991). However, these compounds can be less than desirable for obtaining optimal drug delivery in mammalian organisms, particularly in humans. Some of these compounds can also have a less than desirable serum half-life, and therefore duration of action, because they contain amide bonds in relatively high proportion, and thus are prone to metabolic degradation, hepatic clearance, or other elimination mechanisms.

There exists a need for novel compounds which inhibit retroviral protease activity, and a need for compounds which possess desirable pharmacokinetic properties for good drug delivery and metabolic stability for good serum half-life and duration of action. Such pharmaceutical uses provide therapies for retroviral diseases in mammals, especially in humans, which have been heretofore difficult to treat.

SUMMARY OF THE INVENTION

The present invention provides compounds, hereinafter represented as formula (I), which bind to retroviral proteases. These compounds are inhibitors of retroviral proteases and are useful for treating diseases related to infection by retroviruses.

The present invention also provides a pharmaceutical composition comprising a compound of formula (I) and a pharmaceutically acceptable carrier.

The present invention additionally provides a method for treating retroviral disease, comprising administering to a mammal in need thereof an effective amount of a compound of formula (I).

DETAILED DESCRIPTION OF THE INVENTION

The compounds of the present invention are illustrated by formula (I):

wherein:

$R^1$ and $R^3$ are each independently Q, Q—$C_{1-6}$alkyl, Q—$C_{2-6}$alkenyl, Q—$C_{2-6}$alkynyl or $C_{1-6}$alkyl substituted by one to five fluorine atoms, each optionally substituted by $R^{23}$;

Q is H, $C_{3-6}$cycloalkyl, $C_{5-6}$cycloalkenyl, Ar or Het $R^2$ is H or OH;

$R^4$ is $R^6$—$NR^{11}$— or $CONR^{11}CHR^6R^7$;

$R^5$ is $R^6$—$NR^{11}$— or $R^{10}$—$NR^{11}$—;

$R^6$ is

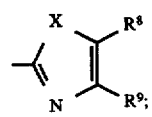

X is $NR^{11}$, O or S;

$R^7$ is Q, Q—$C_{1-6}$alkyl or Q—$C_{2-6}$alkenyl;

$R^8$ and $R^9$ are each independently H, OH, halo, $NO_2$, $COR^{12}$, $CF_3$, Ar, $C_{1-6}$alkyl-$R^{15}$, or $R^{17}(R^{18}R^{19}C)_m$, or together form a fused $C_{2-4}$alkylene, aryl or heteroaryl moiety;

$R^{10}$ is A—$(B)_n$—;

$R^{11}$ is H or $C_{1-4}$alkyl;

$R^{12}$ is $R^7$, $OR^7$, $NR^7R^{11}$ or an amino acid or amino alcohol;

B is an amino acid;

A is H, Ar, Het, $R^{17}(R^{18}R^{19}C)_m$, Ar—W, Het—W or $R^{17}(R^{18}R^{19}C)_m$—W, or phthaloyl each optionally substituted by one to three groups chosen from $R^{15}$ or $C_{1-6}$alkyl-$R^{15}$;

W is C=O, OC(=O), $NR^{11}$C(=O), SC(=O), $NR^{11}$C (=S), $SO_2$, $NR^{11}SO_2$ or P (=O) ($OR^{22}$);

$R^{15}$ is H, nitro, $C_{1-6}$alkoxy, $C_{1-6}$alkylthio, O (C=O) $R^{16}$, C=$OR^{22}$, $CO_2R^{22}$, CON ($R^{16}$)$_2$, N ($R^{22}$)$_2$, NHC(=N)NH—A, I, Br, Cl, F, $OR^{10}$, or OH, provided that when $R^{15}$ is a substituent of the carbon adjacent to W, $R^{15}$ is not halogen or OH when W is OC(=O) or NHCO;

$R^{16}$ is H or $C_{1-6}$alkyl;

$R^{17}$, $R^{18}$ and $R^{19}$ are independently: i) H, $R^{15}$ or $C_{1-4}$alkyl, $C_{2-6}$alkenyl, phenyl, naphthyl, $C_{3-6}$cycloalkyl or Het, each optionally substituted by one to three $R^{15}$ or $R^{15}$—$C_{1-6}$alkyl groups, or ii) $R^{17}$ is as above and ($R^{18}R^{19}$C) are joined together to form a phenyl, naphthyl, $C_{3-6}$cycloalkyl or Het ring, or iii) $R^{17}$ is as above and $R^{18}$ and $R^{19}$ together are =O;

$R^{22}$ is H, $C_{1-6}$alkyl, phenyl or phenyl-$C_{1-4}$alkyl;

$R^{23}$ is —X'—(CH$_2$)$_q$NR$^{24}$R$^{25}$, X"[((CH$_2$)$_r$O)$_s$]R$^{26}$, CH$_2$X"[((CH$_2$)$_r$O)$_s$]R$^{26}$, or benzofuryl, indolyl, azacycloalkyl, azabicyclo $C_{7-11}$cycloalkYl or benzopiperidinyl, optionally substituted with $C_{1-4}$alkyl;

q is 2–5;

s is 1–6 and r is 1–3 within each repeating unit s;

X' is CH$_2$, O, S or NH;

X" is CH$_2$, NR', O, S, SO or SO$_2$;

$R^{24}$ and $R^{25}$ are i) $C_{1-6}$alkyl, optionally substituted by OH, $C_{1-3}$alkoxy, or N(R')$_2$, ii) the same or different and joined together to form a 5–7 member heterocycle containing up to two additional heteroatoms selected from NR, O, S, SO, SO$_2$, said heterocycle optionally substituted with $C_{1-4}$alkyl, iii) aromatic heterocycle, optionally substituted with $C_{1-4}$alkyl or N(R')$_2$;

R' is H or $C_{1-4}$alkyl;

$R^{26}$ is H, $C_{1-4}$alkyl, C(=O)$R^{27}$, C(=O)U[(CH$_2$)$_m$O]nR', P(=O)(OM)$_2$, CO$_2$R$^{27}$, C(=O)NR$^{27}$R$^{28}$, where M is a mono or divalent metal ion, and U is NR' or O;

$R^{27}$ is $C_{1-6}$alkyl or Ar, optionally substituted with one or more hydroxy, carboxy, halo, $C_{1-3}$alkoxy, CONR'$_2$, NR'$_2$, CO$_2$R', SO$_2$NR'$_2$, CH$_2$NR$_2$, NR'COR', NR'SO$_2$R', X"[(CH$_2$)$_r$O]sR' or CH$_2$X"[(CH$_2$)$_r$O]$_s$R';

$R^{28}$ is H, $C_{1-6}$alkyl or together with $R^{27}$ forms a 5–7 membered heterocycle or a 6 membered heterocycle containing a heteroatom selected from N, O and S;

m is 1–4; and n is 0 or 1; or a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

Formula (I) is intended to encompass all unique nonracemic stereoisomers which may occur due to the presence of asymmetric carbon atoms in the molecule. Such compounds may occur as pure enantiomers or diastereomers or as a mixture of individual stereoisomers. The definition of any substituent moiety which may occur more than once in formula (I) is independent of any other occurrence. Combinations of substituents and/or variables are permissible only if such combinations result in stable compounds.

Compounds of this invention which include acyclic double bonds may be present in either the cis (Z) or trans (E) geometrical configuration with respect to any two substituents.

When X is NH, it will be appreciated that the heterocyclic ring is an imidazole which can undergo tautomerization. All tautomeric forms of the imidazole are within the scope of this invention.

Suitably $R^1$ and $R^3$ are $C_{1-6}$alkyl, Ar—$C_{1-6}$alkyl, Ar—$C_{2-6}$alkenyl, Ar—$C_{2-6}$alkynyl, $C_{1-6}$alkyl optionally substituted by one to five fluorine atoms or benzyl substituted in the 4-position by $R^{23}$. Preferably $R^1$ is benzyl and $R^3$ is benzyl, 4-hydroxybenzyl or phenylpropenyl.

Suitably $R^2$ is H.

Suitably X is S or N—$R^{11}$. Preferably X is NH.

Preferably $R^4$ is CONR$^{11}$CHR$^6$R$^7$.

Suitably $R^5$ is $R^{10}$—NR$^{11}$. Preferably $R^5$ is t-butyloxycarbonylamino or isopropyloxycarbonylamino.

Suitably $R^7$ is H, $C_{1-6}$alkyl, $C_{3-6}$cycloalkyl, phenyl or benzyl. Preferably $R^7$ is $C_{1-6}$alkyl. Isopropyl is most preferred.

Suitably $R^8$ is H, $C_{1-6}$alkyl, COR$^{12}$, NO$_2$ or Br. Preferably $R^8$ is H.

Suitably $R^9$ is H, NO$_2$, Br, COR$^{12}$, CF$_3$, Ar, $C_{1-6}$alkyl or $C_{1-6}$alkyl-$R^{15}$, wherein $R^{12}$ is H, $C_{1-6}$alkyl, Ar, OC$_{1-6}$alkyl, NH$_2$, and $R^{15}$ is OH. Preferably $R^9$ is H or COR$^{12}$.

Suitably B is Ala or Val. Preferably m is 0 and B is absent.

Suitably A is Het, $R^{17}$($R^{18}R^{19}$C)$_m$—W, Ar—W or Het—W. Suitably $R^{17}$, $R^{18}$ and $R^{19}$ are H, or $C_{1-4}$alkyl, Het or Ar optionally substituted by one or two $R^{15}$ or $C_{1-6}$alkyl-$R^{15}$, or ($R^{18}R^{19}$C) are joind together to form a phenyl, $C_{3-6}$cycloalkyl or Het ring.

Suitably W is C=O, OC(=O), NHC(=O), NHC(=S), or SC(C=O).

Suitably $R^{17}$($R^{18}R^{19}$C)$_m$— is Ar—CH$_2$, Ar, Het, Het—CH$_2$, $C_{1-6}$alkyl or $C_{3-6}$cycloalkyl optionally substituted by one to three groups selected from $R^{15}$. Suitably $R^{15}$ is OH. When $R^{17}$ or ($R^{18}R^{19}$C) are Het or Ar, Het is suitably quinolinyl, pyridyl, imidazolyl, thiazolyl, tetrahydrothiopyranyl or tetrahydropyranyl and Ar is phenyl.

Suitably $R^{23}$ is hydroxy-$C_{1-4}$alkoxy, $C_{1-4}$alkoxy-$C_{1-4}$alkoxy, or —O(CH$_2$)$_2$NR$^{24}$R$^{25}$, wherein $R^{24}$ and $R^{25}$ are are a 5- or 6-membered heterocycle, such as morpholino.

In one preferred embodiment W is C=O.

In another preferred embodiment W is OC(=O).

In a third preferred embodiment $R^{10}$ is $C_{1-6}$alkylOC(=O) or $C_{5-6}$cycloalkylOC(=O) substituted by one or two OH or CH$_2$OH groups.

Representative compounds of this invention are:

(2R,4S,5S,1'S)-2-phenylmethyl-4-hydroxy-5-(t-butoxycarbonyl)-amino-6-phenyl-N-[1'-isopropyl-1'-(4-aminocarbonyl-thiazo-2-yl)]methyl-hexanamide;

(2R,4S,5S,1'S)-2-phenylmethyl-4-hydroxy-5-(t-butoxycarbonyl)-amino-6-phenyl-N-[1'-isopropyl-1'-(thiazo-2-yl)]methyl-hexanamide;

(2R,4S,5S,1'S)-2-phenylmethyl-4-hydroxy-5-(t-butoxycarbonyl)-amino-6-phenyl-N-(1'-imidazo-2-yl) methyl-hexanamide hydrochloride;

(2R,4S,5S,1'S)-2-phenylmethyl-4-hydroxy-5-(t-butoxycarbonyl)-amino-6-phenyl-N-[1'-methyl-1'-(imidazo-2-yl)] methyl-hexanamide hydrochloride;

(2R,4S,5S,1'S)-2-phenylmethyl-4-hydroxy-5-(t-butoxycarbonyl)-amino-6-phenyl-N-[1'-benzyl-1'-(imidazo-2-yl)]methyl-hexanamide hydrochloride;

(2R,4S,5S,1'S)-5-(carbobenzyloxy)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4,5-dimethyl)imidazol-2-yl]methyl-6-phenyl-2-phenylmethyl-hexanamide;

(2R,4S,5S,1'S)-5-(t-butoxycarbonyl)amino-4-hydroxy-N-[1'-isopropyl-1'-(N'-methyl)imidazol-2-yl]methyl-6-phenyl-2-phenylmethyl-hexanamide;

(2R,4S,5S,1'S)-5-(t-butoxycarbonyl)amino-4-hydroxy-N-(1'-isopropyl-1'-imidazol-2-yl)methyl-6-phenyl-2-(3-phenylpropargyl)hexanamide;

(2R,4S,5S,1'S)-5-(benzyloxyethoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(methoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(ethoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-(1'-isopropyl-1'-imidazol-2-yl)methyl-6-phenyl-2-(3-phenyl-2-propenyl)hexanamide;

(2R,4S,5S,1'S)-5-(t-butoxycarbonyl)amino-4-hydroxy-N-[1'-isopropyl-1'-(4-nitroimidazol-2-yl)]methyl-6-phenyl-2-phenylmethyl-hexanamide;

(2R,4S,5S,1'S)-5-(t-butoxycarbonyl)amino-4-hydroxy-N-(1'-ethyl-1'-imidazol-2-yl)methyl-6-phenyl-2-phenylmethyl-hexanamide;

(2R,4S,5S,1'S)-5-(t-butoxycarbonyl)amino-4-hydroxy-N-(1'-propyl-1'-imidazol -2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4-bromoimidazol -2-yl)]methyl-6-phenyl-2-phenylmethyl-hexanamide;

(2R,4S,5S,1'S)-5-(t-butoxycarbonyl)aminno-4-hydroxy-N-[1'-isopropyl-1'-(4,5-dibromoimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-methylimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-trifluoromethylimidazol-2-yl)]methyl-6-phenyl-2-phenylmethyl-hexanamide;

(2R,4S,5S,1'S)-5-(t-butoxycarbonyl)amino-4-hydroxy-N-methyl-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4-carbomethoxyimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-methylcarbonylimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-phenylcarbonyl-imidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-formylimidazol-2-yl)]methyl-6-phenyl-2-phenylmethyl-hexanamide; (2R,4S,5S,1'S)-5-(t-butoxycarbonyl)amino-4-hydroxy-N-[1'-isopropyl-1'-(4-(hydroxymethyl)-imidazol-2-yl)]methyl-6-phenyl-2-phenylmethyl-hexanamide;

(2R,4S,5S,1'S)-5-((tetrahydrothiopyran-4-yl)oxycarbonyl)-amino-4-hydroxy-N-(1'-isopropyl-1'-imidazol-2-yl)methyl-6-phenyl-2-phenylmethyl-hexanamide;

(2R,4S,5S,1'S)-5-((tetrahydro-4H-pyran-4-yl)oxycarbonyl)-amino-4-hydroxy-N-(1'-isopropyl-1'-imidazol-2-yl)methyl-6-phenyl-2-phenylmethyl-hexanamide;

(2R,4S,5S,1'S)-5-(4-picolinyloxy)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-(1'-isopropyl-1'-imidazol-2-yl)methyl-6-phenyl-2-(4,4,4-trifluorobut-1-yl)hexanamide;

(2R,4S,5S,1'S)-5-(t-butoxycarbonyl)amino-4-hydroxy-N-[1'-isopropyl-1'-(4-((1RS)-1-hydroxyethyl)-imidazol-2-yl)]methyl-6-phenyl-2-phenylmethyl-hexanamide;

(2R,4S,5S,1'S)-5-(t-butoxycarbonyl)amino-4-hydroxy-N-[1'-(1-methyl)propyl-1'-(imidazol-2-yl)]methyl-6-phenyl-2-phenylmethyl-hexanamide;

(2R,4S,5S,1'S)-5-(propylaminocarbonyl)amino-4-hydroxy-N-[1'-isopropyl-1'-(imidazol-2-yl)]methyl-6-phenyl-2-phenylmethyl-hexanamide;

(2R,4S,5S,1'S)-5-(4-hydroxybutanoyl)amino-4-hydroxy-N-(1'-isopropyl-1'-imidazol-2-yl)methyl-6-phenyl-2-phenylmethylhexanamide;

(2R,4S,5S,1'S)-2-phenylmethyl-4-hydroxy-5-(benzyloxycarbonyl)valylamino-6-phenyl-N-(1'-isobutyl-1'-imidazo-2-yl)methyl-hexanamide;

(2R,4S,5S,1'S)-2-phenylmethyl-4-hydroxy-5-(N-acetylvalyl)-amino-6-phenyl-N-(1'-isobutyl-1'-imidazo-2-yl)methyl-hexanamide;

(2R,4S,5S,1'S)-5-[(imidazol-2-yl)methyloxycarbonyl]amino-4-hydroxy-N-(1'-isopropyl-1'-imidazol-2-yl)methyl-6-phenyl-2-phenylmethyl-hexanamide;

(2R,4S,5S,1'S,1"RS)-5-((1"-(imidazol-2-yl)-2"-methyl)-propyloxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4-(imidazol-2-yl)imidazol-2-yl)]methyl-6-phenyl-2-phenylmethyl-hexanamide;

(2R,4S,5S,1'S)-5-(1-oxo-thian-4-yl)oxycarbonyl)amino-4-hydroxy-N-(1'-isopropyl-1'-imidazol-2-yl)methyl-6-phenyl-2-phenylmethylhexanamide;

(2R,4S,5S,1'S)-5-((tetrahydrosulfonylpyran-4-yl)oxycarbonyl)amino-4-hydroxy-N-(1'-isopropyl-1'-imidazo-2-yl)methyl-6-phenyl-2-phenylmethylhexanamide;

(2R,4S,5S,1'S)-5-((1,1-dimethyl-2-(benzyloxycarbonyl-glycyloxy)ethoxycarbonyl)amino-4-hydroxy-N-(1'-isopropyl'-imidazol- 2-yl)methyl-6-phenyl-2-phenylmethyl-hexanamide hydrochloride salt;

(2R,4S,5S,1'S)-5-((1,1-dimethyl-2-glycyloxy)ethoxycarbonyl)-amino-4-hydroxy-N-(1'-isopropyl-1'-imidazol-2-yl)methyl-6-phenyl-2-phenylmethyl-hexanamidedihydrochloridesalt;

(2R,4S,5S,1'S)-5-((1-acetyl)amino-4-hydroxy-N-(1'-isopropyl-1'-imidazol-2-yl)methyl-6-phenyl-2-phenylmethylhexanamide;

(2R,4S,5S,1'S)-5-(t-butoxycarbonyl)amino-4-hydroxy-N-(1'-isopropyl-1'imidazol-2-yl)methyl-6-phenyl-2-(4-benzyloxyphenylmethyl)hexanamide;

(2R,4S,5S,1'S)-5-(t-butoxycarbonyl)amino-4-hydroxy-N-(1'-isopropyl-1'imidazol-2-yl)methyl-6-phenyl-2-(4-hydroxyphenylmethyl)hexanamide;

(2R,4S,5S)-5-(t-butoxycarbonyl)amino-4-hydroxy-2-phenylmethyl-6-phenyl-N-[1'-cyclopropyl-1'-imidazol-2-yl]methyl-hexanamide;

(2R,4S,5S,1'S)-5-((isopropylthiol)carbonyl)-amino-4-hydroxy-2-phenylmethyl-6-phenyl-N-[1-isopropyl-1'-imidazol-2-yl]methyl-hexanamide;

(2R,4S,5S,1'S)-5-[3-(1H-imidazol-2-yl)-3-hydroxy-4-methylpentylamido]-4-hydroxy-N-(1'-isopropyl-1'-imidazol-2-yl)methyl-6-phenyl-2-phenylmethyl-hexanamide;

(2R,4S,5S,1'S)-5-[(4-methoxyphenoxy)carbonyl]amino-4-hydroxy-N-(1'-isopropyl-1'-imidazol-2-yl)methyl-6-phenyl-2-phenylmethyl-hexanamide;

2R,4S,5S,1'S)-5-(t-butylaminocarbonyl)amino-4-hydroxy-N-(1'-isopropyl-1'-imidazol-2-yl)methyl-6-phenylmethyl-hexanamide;

(2R,4S,5S,1'S)-5-(methylaminocarbonyl)-; amino-4-hydroxy-N-(1'-isopropyl-1'-imidazol-2-yl)methyl-6-phenylmethyl-hexanamide;

(2R,4S,5S,1'S)-5-phenylaminocarbonyl)amino-4-hydroxy-N-(1'-isopropyl-1'-imidazol-2-yl)methyl-6-phenylmethyl-hexamide;
(2R,4S,5S,1'S)-5-N-(propylaminocarbonyl)amino-4-hydroxy-N-(1'-isopropyl-1'-imidazol-2-yl)methyl-6-phenylmethyl-hexamide;
(2R,4S,5S,1'S)-5-(n-propylaminothiono)amino-4-hydroxy-N-(1'isopropyl-1'-imidazol-2-yl)methyl-6-phenylmethyl-hexamide;
2R,4S,5S,1'S)-5-(isopropylaminocarbonyl)-amino-4-hydroxy-N-(1'-isopropyl-1'-imidazol-2-yl)methyl-6-phenylmethyl-hexamide;
(2R,4S,5S,1'S)-5-(aminocarbonyl)amino-4-hydroxy-N-(1'-isopropyl-1'-imidazol-2-yl)methyl-6-phenylmethyl-hexamide;
(2R,4S,5S,1'S)-5-(6-quinolinylmethyloxy-carbonyl)amino-4-hydroxy-N-(1'-isopropyl-1'-imidazol-2-yl)methyl-6-phenylmethyl-hexanamide;
(2R,4S,5S,1'S)-5-(benzoyl)amino-4-hydroxy-N-(1'-isopropyl-1'-imidazol-2-yl)methyl-6-phenylmethyl-hexanamide;
(2R,4S,5S,1'S)-5-(2-furylcarbonyl)amino-4-hydroxy-N-(1'-isopropyl-1'-imidazol-2-yl)methyl-6-phenylmethyl-hexanamide;
(2R,4S,5S,1'S)-5-(4-methoxybenzoyl)amino-4-hydroxy-N-(1'-isopropyl-1-imidazol-2-yl)methyl-6-phenylmethyl-hexanamide;
(2R,4S,5S,1'S)-5-benzylcarbonyl)amino-4-hydroxy-N-(1'-isopropyl-1'-imidazol-2-yl)methyl-6-phenylmethyl-hexamide;
(2R,4S,5S,1'S)-5-(4-hydroxybenzoyl)amino-4-hydroxy-N-(1'-isopropyl-1'-imidazol-2-yl)methyl-6-phenylmethyl-hexanamide;
(2R,4S,5S,1'S)-5-(cinnamoyl)amino-4-hydroxy-N-(1'-isopropyl-1'-imidazol-2-yl)methyl-6-phenylmethyl-hexanamide;
(2R,4S,5S,1'S)-5-(2-hydroxybenzoyl)amino-4-hydroxy-N-(1'-isopropyl-1'-imidazol-2-yl)methyl-6-phenylmethyl-hexanamide;
(2R,4S,5S,1'S)-5-(imidazoyl-4-yl-acetyl)amino-4-hydroxy-N-(1'-isopropyl-1'-imidazol-2-yl)methyl-6-phenylmethyl-hexanamide;
(2R,4S,5S,1'S)-5-(t-butoxycarbonyl)amino-4-hydroxy-N-[1'-isopropyl-1'-(4-carbomethoxyethylimidazol-2-yl)]methyl-6-phenyl-2-phenylmethyl-hexanamide;
(2R,4S,5S,1'S)-5-(t-butoxycarbonyl)amino-4-hydroxy-N-[1'-isopropyl-1'-(4-carboxamidoimidazol-2-yl)]methyl-6-phenyl-2-phenylmethyl-hexanamide;
(2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide;
(2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide;
(2R,4S,5S,1'S)-2-phenylmethyl-4-hydroxy-5-(5-propyl-2-thiazolyl)amino)-6-phenyl-N-(1'-isopropyl-1'-(imidazo-2-yl))methyl-hexanamide; and
(2R,4S,5S,1'S)-5-(nicotinyl)amino-4-hydroxy-N-(1'-isopropyl-1'-imidazol-2-yl)methyl-6-phenylmethyl-hexamide.

Another group of preferred representative compounds are:
(2R,4S,5S,1'S)-5-[di(hydroxymethyl)-methoxycarbonyl]amino-4-hydroxy-N-(1'-isopropyl-1'-imidazol-2-yl)methyl-6-phenyl-2-phenylmethyl-hexanamide;
(2R,4S,5S,1'S)-5-(1,1-dimethyl-2-acetoxyethoxycarbonyl)amino-4-hydroxy-N-(1'-isopropyl-1'-imidazol-2-yl)methyl-6-phenyl-2-phenylmethyl-hexanamide;
(2R,4S,5S,1'S)-5-((1,1-dimethyl-2-hydroxy)ethoxycarbonyl)amino-4-hydroxy-N-(1'-isopropyl-1'-(4-isopropylcarbonyl-imidazol-2-yl))methyl-6-phenyl-2-phenylmethyl-hexanamide dihydrochloride salt;
(2R,4S,5S,1'S)-5-((1S)-1-methyl-2-hydroxyethoxycarbonyl)-amino-4-hydroxy-N-(1'-isopropyl-1'-imidazol-2-yl)methyl-6-phenyl-2-phenylmethylhexanamide;
(2R,4S,5S,1'S)-5-((1R)-1-methyl-2-hydroxyethoxycarbonyl)-amino-4-hydroxy-N-(1'-isopropyl-1'-imidazol-2-yl)methyl-6-phenyl-2-phenylmethylhexanamide;
(2R,4S,5S,1'S)5-(1-hydroxymethyl-cyclopentyloxycarbonyl)-amino-4-hydroxy-N-(1'-isopropyl-1'-imidazol-2-yl)methyl-6-phenyl-2-phenylmethyl-hexamide;
(2R,4S,5S,1'S)-5-(1,1-dimethyl-2-hydroxyethoxycarbonyl)amino-4-hydroxy-N-(1'-isopropyl-1'-imidazol-2-yl)methyl-6-phenyl-2-phenylmethyl-hexanamide hydrochloride;
(2R,4S,5S,1'S)-5-(hydroxyethoxycarbonyl)amino-4-hydroxy-N-(1'-isopropyl-1'-imidazol-2-yl)methyl-6-phenyl-2-phenylmethylhexanamide; and
(2R,4S,5S,1'S)-5-(2-hydroxy-1-methylethoxycarbonyl)amino-4-hydroxy-N-(1'-isopropyl-1'-imidazol-2-yl)methyl-6-phenyl-2-phenylmethylhexanamide.

More preferred representative compounds are:
(2R,4S,5S,1'S)-2-phenylmethyl-4-hydroxy-5-(t-butoxycarbonyl)-amino-6-phenyl-N-(1'-isopropyl-1'-(imidazo-2-yl))methyl-hexanamide hydrochloride;
(2R,4S,5S,1'S)-5-(isopropoxycarbonyl)amino-4-hydroxy-N-(1'-isopropyl-1'-imidazol-2-yl)methyl-6-phenyl-2-phenylmethyl-hexanamide;
(2R,4S,5S,1'S)-5-(t-butoxycarbonyl)amino-4-hydroxy-N-[1'-isopropyl-1'-(4-isopropylcarbonyl-imidazol-2-yl)]methyl-6-phenyl-2-phenylmethyl-hexanamide;
(2R,4S,5S,1'S)-5-(1,1-dimethyl-2-hydroxyethoxycarbonyl)amino-4-hydroxy-N-(1'-isopropyl-1'-imidazol-2-yl)methyl-6-phenyl-2-phenylmethyl-hexanamide hydrochloride;
(2R,4S,5S,1'S)-5-(hydroxyethoxycarbonyl)amino-4-hydroxy-N-(1'-isopropyl-1'-imidazol-2-yl)methyl-6-phenyl-2-phenylmethylhexanamide; and
(2R,4S,5S,1'S)-5-(2-hydroxy-1-methylethoxycarbonyl)amino-4-hydroxy-N-(1'-isopropyl-1'-imidazol-2-yl)methyl-6-phenyl-2-phenylmethylhexanamide.

The term "alkyl" refers to a straight or branched chain alkyl radical of the indicated number of carbon atoms. "$C_{1-4}$alkyl" as applied herein is meant to include methyl, ethyl, propyl, isopropyl, butyl, isobutyl, sec-butyl, tert-butyl; "$C_{1-6}$alkyl" includes additionally pentyl, isopentyl, 2-methylbutyl, 1-methylbutyl, 2-ethylpropyl, neopentyl, n-hexyl 2,2-dimethylbutyl, 2-methylpentyl, and the like. "Alkoxy" refers to an alkyl group of the indicated number of carbon atoms attached through a bridging oxygen atom. "Alkylthio" refers to an alkyl group of the indicated number of carbon atoms attached through a bridging sulfur atom.

The term "substituted alkyl" as used herein is meant to include $C_{1-6}$alkyl, Ar-$C_{1-6}$alkyl, Het-$C_{1-6}$alkyl, $C_{2-6}$alkenyl, Ar-$C_{2-6}$alkenyl, Het-$C_{2-6}$alkenyl, $C_{3-6}$cycloalkyl-$C_{1-6}$alkyl, $C_{3-6}$cycloalkenyl-$C_{1-6}$alkyl or $C_{1-6}$alkyl substituted with acyl or hydroxyl.

"Alkenyl" refers to a straight or branched hydrocarbon chain of the indicated number of carbon atoms, which contains one or more carbon-carbon double bonds at any stable point along the chain, such as ethenyl, propenyl, butenyl, pentenyl, 2-methylpropenyl, hexenyl, and the like.

"Alkynyl" refers to a straight or branched hydrocarbon chain of the indicated number of carbon atoms which contains a carbon-carbon triple bond at any stable point along the chain, such as ethynyl, 2-propynyl, 2-butynyl, 4-pentynyl, 2-methyl-3-propynyl, hexynyl and the like.

The term "acyl" means $R^{12}$—CO, wherein $R^{12}$ is H, $C_{1-6}$alkyl, Ar-$C_{1-6}$alkyl, Het-$C_{1-6}$alkyl, $C_{2-6}$alkenyl, Ar-$C_{2-6}$alkenyl, Het-$C_{2-6}$alkenyl, $C_{3-6}$cycloalkyl-$C_{1-6}$alkyl, $C_{5-6}$cycloalkenyl-$C_{1-6}$alkyl, OH, $NHR_{13}$, wherein $R^{13}$ is H, $C_{1-6}$alkyl, Ar-$C_{1-6}$alkyl, Het-$C_{1-6}$alkyl, $C_{2-6}$alkenyl, Ar-$C_{2-6}$alkenyl, Het-$C_{2-6}$alkenyl, $C_{3-6}$cycloakyl-$C_{1-6}$alkyl, or $C_{3-6}$cycloalkyl, or $C_{5-6}$cycloalkenyl-$C_{1-6}$alkyl; or an α-amino acid or an α-amino alcohol bonded at the nitrogen.

"Cycloalkyl" refers to a saturated ring group of the indicated number of carbon atoms. "$C_{3-7}$cycl oalkyl" includes cyclopropyl, cyclobutyl, cyclopentyl, cyclohexyl and cycloheptyl. "Cycloalkenyl" refers to a saturated ring group of the indicated number of carbon atoms, having at least one endocyclic carbon-carbon double bond. "$C_{5-7}$ cycloalkenyl" includes cyclopentenyl, cyclohexenyl and cycloheptenyl.

"Aryl", abbreviated as Ar, refers to phenyl or naphthyl, optionally substituted with one to three halo, OH, $OR^{10}$, $C_{1-6}$alkyl, $C_{1-6}$alkoxy, $C_{1-6}$alkylthio, $C_{1-6}$alkylamino, $CF_3$, amino, $NO_2$, carboxy, $C_{1-4}$alkylcarbonyl, aminocarbonyl, $C_{1-6}$alkyl-Het, $C_{1-6}$alkoxy-Het, $C_{1-6}$alkyl-phenyl, $C_{1-6}$alkoxy-phenyl, $C_{1-6}$alkyl-, $C_{1-6}$alkoxy-, Het$C_{1-6}$alkyl-, Het$C_{1-6}$alkoxy-, phenyl$C_{1-6}$alkyl-, phenyl$C_{1-6}$alkoxy- or phenyloxy.

As used herein except where noted, the term "heterocycle", abbreviated as "Het", represents a stable 5- to 7-membered monocyclic or a stable 7- to 10-membered bicyclic heterocyclic ring, which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one to three halo, OH, alkyl, alkoxy, alkyl-Het, alkoxy-Het, alkyl-phenyl, alkoxy-phenyl. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, thiamorpholinyl sulfoxide, thiamorpholinyl sulfone, and oxadiazolyl. Heteroaryl refers to a heterocycle which has aromatic character (eg., characterized by delocalized electron resonance and the ability to sustain a ring current). Pyridine, imidazole, thiazole, furan and oxazole are examples of heteroaryl rings.

"Amino acid" means the D- or L-isomer of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or trifluoroalanine. In general, the amino acid abbreviations follow the IUPAC-IUB Joint Commission on Biochemical Nomenclature as described in *Eur. J. Biochem.*, 158, 9 (1984). Usually lipophilic amino acids are preferred for the moiety B, for instance, Val, Ala, Leu and Ile. It will be understood that a linkage B-O refers to an oxygen atom bonded to the carboxyl group of an amino acid, and that a B-N linkage indicates a nitrogen atom bonded to the carboxyl group of an amino acid, as in an amide bond. "Amino alcohol" refers to an amino acid in which the carboxyl group has been reduced to a methylene hydroxy group.

Certain chemical names are abbreviated herein for the sake of convenience. Boc refers to the t-butoxycarbonyl radical. Cbz refers to the carbobenzyloxy radical. Bzl refers to the benyzl radical. Ac refers to acetyl. Ph refers to phenyl. BOP refers to benzotriazol-1-yloxy-tris(dimethylamino) phosphonium hexafluorophosphate. DCC refers to dicyclohexylcarbodiimide. DMAP refers to dimethylaminopyridine. DMSO refers to dimethylsulfoxide. HOBT refers to 1-hydroxybenzotriazole. NMM is N-methylmorpholine. DTT is dithiothreitoi. EDTA is ethylenediamine tetraacetic acid. DIEA is diisopropyl ethylamine. DBU is 1.8 diazobicyclo[5.4.0]undec-7-ene. DMSO is dimethylsulfoxide. DMF is dimethyl formamide; Lawesson's reagent is 2,4-bis(4-methoxyphenyl)-1,3-dithia-2,4-diphosphetane-2,4-disulfide and THF is tetrahydrofuran. HF refers to hydrofluoric acid and TFA refers to trifluoroacetic acid.

The compounds of formula (I):

wherein $R^4$ is CO—NR'CHR$^6$R$^7$, $R^5$ is $R^{10}R^{11}$N—, and $R^1$, $R^2$, $R^3$ and $R^6$ are as defined in formula (I), are prepared by:

1) (a) coupling a compound of the formula (II):

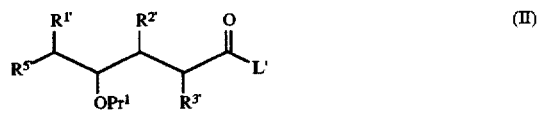

with a compound of formula (III):

where $R^{1'}$, $R^{2'}$, $R^{3'}$, $R^{5'}$, $R^{6'}$ and $R^{7'}$ are as defined for formula (I) with any reactive groups protected, $Pr^1$ is H or a hydroxyl protecting group, and L' is OH or a leaving group; or (b) coupling a compound of the formula (IV):

with a compound of the formula (V):

wherein A' and B' are as defined in formula (I) with any reactive groups protected; or (c) coupling a compound of the formula (VI):

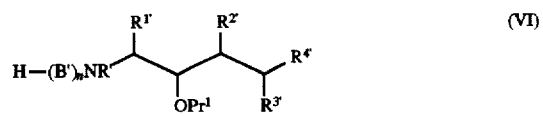

with a compound of the formula (VII):

and, 2) if appropriate, a coupling agent; and 3) removing any protecting groups and 4) forming a pharmaceutically acceptable salt thereof.

The coupling reactions may be accomplished by activating the substrate with a reactive functional group in situ or prior to the coupling reaction, such that it is reactive with an amino group. For instance, acids may be converted to acid chlorides, bromides, activated esters or anhydrides, or by adding a coupling reagent. Coupling agents are well known in the art for activating a functional group in situ., Exemplary of such agents are DCC and other carbodiimides, DMAPEC, used with othehese coupling agents may optionally be used with other reagents, such a HOBT, NMM and DMAP, which may facilitate the reaction.

Suitable leaving groups, L', are those which are displaceable by an amino group, such as bromo, chloro, a substituted acyl (eg. trifluoroacetyl, bromobenzoyl, nitrobenzoyl) or a substituted phenol (eg. 4-nitrophenol) and the like. If L' is OH, so that A-OH is an acid, it will be appropriate to use a coupling agent as hereinbefore described.

For instance:

When A is a substituted alkyl group, such as $R^{17}$ $(R^{18}R^{19}C)_m$, L' may be a bromo, chloro, iodo or an alkyl or aryl sulonate.

When A is $R^{17}(R^{18}R^{19}C)_m$-W, Ar-W or Het-W, and W is C=O, A-L' may be a carboxylic acid halide, activated ester or anhydride, or a carboxyl ic acid in the presence of a coupling agent. Methods for preparing such compounds are well known.

When W is OC=O, A-L' may be a chloro- or bromoformate, or an activated carbonate. Haloformates may be prepared by reacting the appropriate alcohol with phosgene or carbonyldibromide. Activated carbonates may be prepared by reacting the appropriate alcohol with a suitable carbonate such as bis(4-nitrophenyl)carbonate.

When W is $SO_2$, A-L' may be a sulfonyl halide which may be prepared from the corresponding sulfonic acid.

When W is SC=O, A-L' may be a halothioformate, which may be prepared from a carbonyldihalide and an appropriate mercaptan.

When W is $PO(OR^{22})$, A-L' may be a phosphonyl halide, which may be prepared from the corresponding phosphonic acid.

Compounds wherein A is $R^{17}(R^{18}R^{19}C)_m$-W, Ar-W or Het-W, and W is NR'C=O are ureas, and may be prepared by reacting a compound of formula (VII) with an isocyanate of the formula $R^{17}(R^{18}R^{19}C)_m$—NCO, Ar-NCO or Het-NCO, in a suitable solvent such as methylene chloride, optionally with heating.

Compounds of formula (III), wherein X is nitrogen, are imidazoles and may be prepared according to Scheme 1, wherein $Pr^2$ is a removeable amino protecting group, and $R^{7'}$, $R^{8'}$ and $R^{9'}$ correspond to $R^7$, $R^8$ and $R^9$ as defined for formula (I), or a group which may be converted into $R^7$, $R^8$ or $R^9$, with any reactive groups protected.

Scheme 1

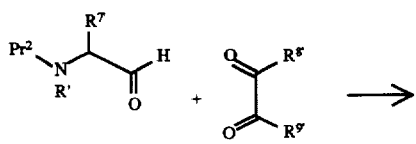

-continued
Scheme 1

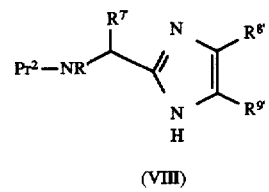

(VIII)

The amino aldehydes are generally known or are prepared by methods well known in the art, for instance, by reduction of a suitable α-amino acid ester with diisobutylaluminum hydride. Further reaction of the aldehyde with a gem dial dehyde, or diketone, and ammonia yields the desired imidazole. Alkylation and further modification of the substituent groups of the imidazole are within the skill of the art. Such a method and other methods for preparing imidazoles are disclosed, for instance, by Baldwin et al., *J. Med. Chem.*, 29, 1065 (1986), *Angew. Chem. Int.*, 22, 560 (1983), and Hughey et al., *Synthesis*, 489 (1980). Alternately, acyl imidazoles may be prepared by coupling an α-amino acid to a substituted 4-amino-isoxazole, and subsequent reduction and base catalyzed rearrangement as disclosed generally by Reiter, L. A., *J. Org. Chem.*, 52, 2714 (1987). Intermediate compounds of formula (VIII) are a part of this invention. Preferably, $R^{7'}$ is $C_{1-6}$alkyl and more preferably $C_{3-6}$alkyl. Suitably, $R^{8'}$ and $R^{9'}$ are H, $NO_2$, Br, $COR^{12}$, $CF_3$, Ar, $C_{1-6}$alkyl or $C_{1-6}$alkyl-$R^{15}$, wherein $R^{12}$ is H, $C_{1-6}$alkyl, Ar, $OC_{1-6}$alkyl, $NH_2$, and $R^{15}$ is OH or a protected hydroxyl group. Preferably $R^{9'}$ is H or $COR^{12}$.

Compounds of formula (III), wherein X is sulfur, are thiazoles and may be prepared according to Scheme 2, wherein L" is a suitable displaceable group.

Scheme 2

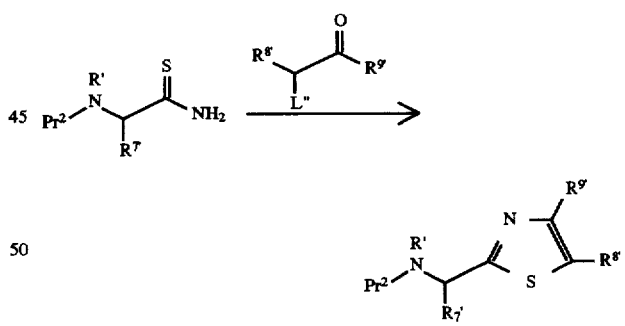

Accordingly, a thioamide is reacted with a ketone or aldehyde. Thioamides are commonly prepared from carboxamides by reacting the corresponding carboxamides with a reagent such as Lawessons reagent, as disclosed, for instance, by Hamada et al., *Tet. Lett.*, 931 (1991). Suitable displaceable groups are those which are displaced by a sulfur nucleophile, such as chloride, bromide, iodide, mesylate, p-tolunesufonate groups, and the like.

Compounds of formula (III), wherein X is oxygen, are oxazoles and may be prepared according to Scheme 3 from common amino acids.

Scheme 3

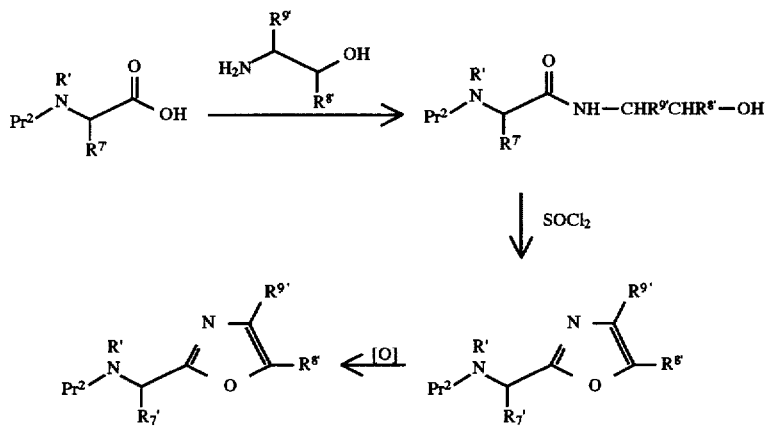

Typically the acid may be coupled to an appropriately substituted amino alcohol by common techniques, as described above, and cyclized by treatment with thionyl chloride to yield an oxazoline, as described by Meyers et al., *J. Org. Chem.*, 43, 1372 (1978). Oxidation of the oxazoline, such as described by Evans et al., *J. Org. Chem.*, 44, 497 (1979), yields an oxazole.

The compounds of formula (II), (IV) and (VI), wherein $R^2$ is H, are prepared, for instance, according to Scheme 4.

4828 (1986), Halladay et al., Tett. Lett., 24, 4401 (1983), Wuts et al., J. Org. Chem., 53, 4503 (1988), DeCamp et al., Tett. Lett., 32, 1867 (1991), and Szelke et al., WO 84/03044, all of which are incorporated herein by reference.

The compounds of formula (II), (IV) and (VI), wherein $R^2$ is OH, are also prepared by methods common in the art such as those disclosed in U.S. Pat. No. 4,864,017, and Thaisrivongs et al., *J. Med. Chem.*, 30, 976 (1987).

Scheme 4

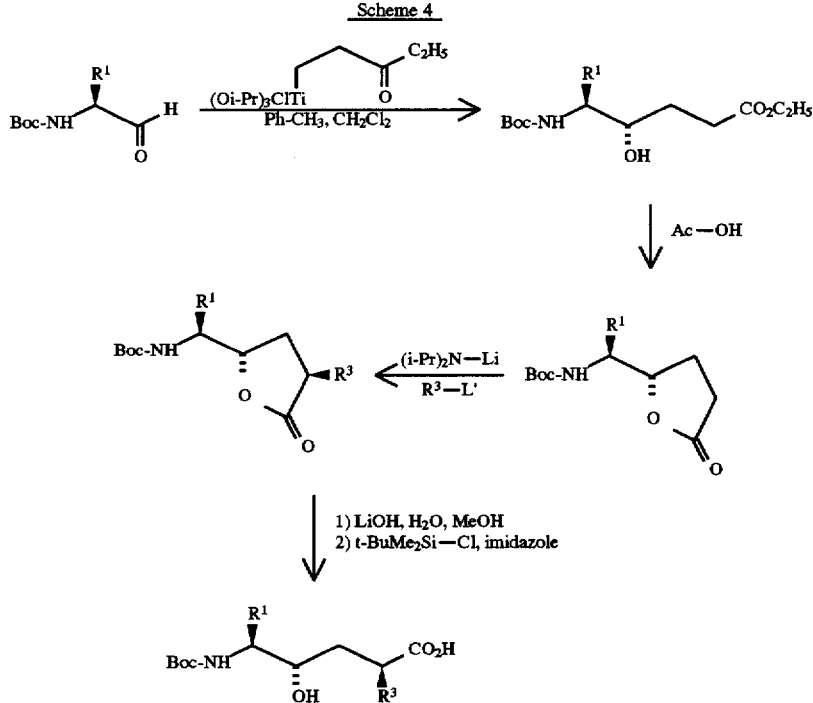

Other methods for preparing protected 5-amino-4-hydroxy-2,5-disubstituted-pentanoate esters and acids, and the corresponding γ-lactones, are well known and are disclosed, for instance, in Szelke et al., U.S. Pat. No. 4,713,455, Boger et al., U.S. Pat. No. 4,661,473, EP-A 0 352 000, Evans et al., J. Org. Chem., 50, 4615 (1985), Kempf, J. Org. Chem., 51, 3921 (1986), Fray et al., J. Org. Chem., 51, Compounds of formula (I), wherein $R^5$ is $R^6$—$NR^{11}$, are prepared according to Scheme 5, Scheme 6 or Scheme 7:

Scheme 5

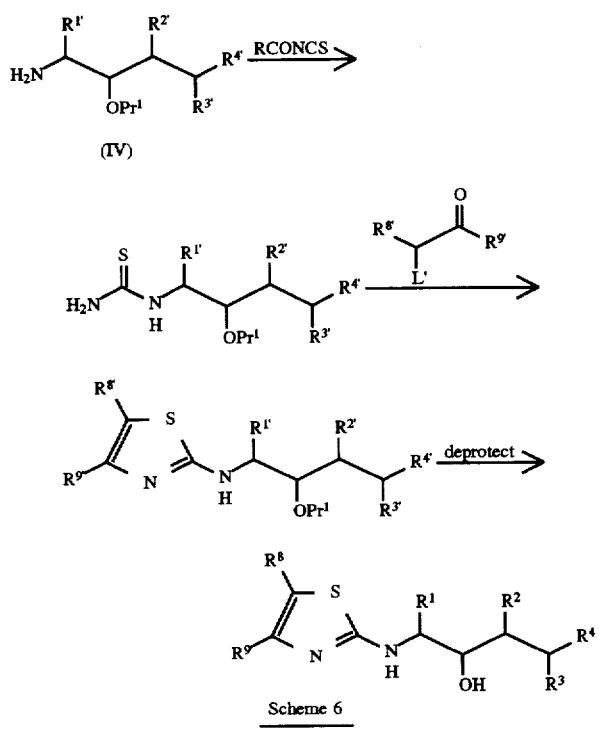

Scheme 6

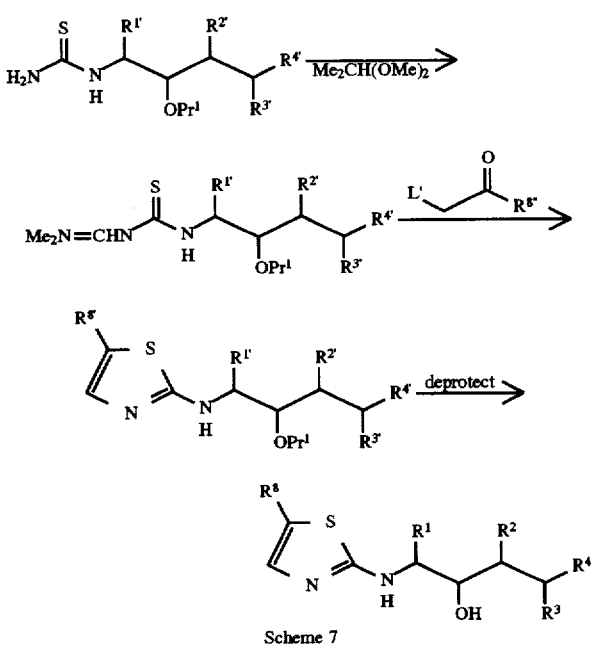

Scheme 7

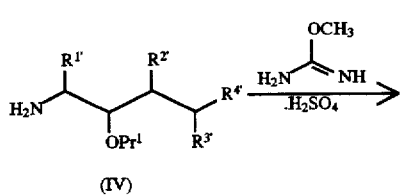

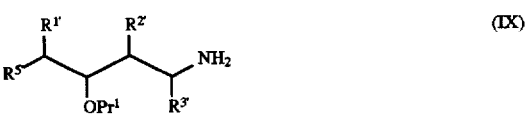

wherein $R^{1'}$-$R^{4'}$, $R^{7'}$ and $R^{8'}$ are as defined in formula (I) with any reactive groups protected, L' is a leaving group, such as halogen, and $Pr^1$ is a hydroxy-protecting group Compounds wherein $R^4$ is $R^6NR^{11}$— are prepared in an analogous manner from a compound of formula (IX):

(IX)

Suitable protecting groups for the amino, hydroxyl, carboxylic acid, mercaptan group, and reagents for deprotecting these functional groups are disclosed in Greene et al., PROTECTIVE GROUPS IN ORGANIC SYNTHESIS, Second Edition, John Wiley and Sons, New York, 1991. Deprotection indicates the removal of the protecting group and replacement with an hydrogen atom. In particular, suitably substituted acetyl, benzyl and silyl groups are useful for protecting the hydroxyl group. The acetyl group is commonly removed by reacting the compound with a base, such as an alkali metal hydroxide, in a mixture of an alcohol and water. The silyl group, such as trimethyl silyl, dimethyl-t-butyl silyl, and t-butyl-diphenyl silyl may be removed by a fluoride reagent, such as a tetra-alkyl ammonium fluoride, or by acid hydrolysis. The benzyl group may be removed by catalytic hydrogenation.

Suitable protecting groups for the amino group are those disclosed by Greene et al., as indicated previously. The benzyloxycarbonyl and t-butoxycarbonyl groups are especially useful amino protecting groups.

The present invention includes pharmaceutically acceptable acid addition salts. Acid addition salts of the present compounds are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. If the final compound contains an acidic group, cationic salts may be prepared. Typically the parent compound is treated with an excess of an alkaline reagent, such as a hydroxide, carbonate or alkoxide, containing the appropriate cation. Cations such as $Na^+$, $K^+$, $Ca^{++}$ and $NH_4^+$ are examples of cations present in pharmaceutically acceptable salts. Certain of the compounds form inner salts or zwitterions which may also be acceptable.

The compounds of the present invention selectively bind to retroviral proteases in the same manner as the virally coded natural substrates of the proteases and compete with these substrates for protease, thereby serving to inhibit viral replication by blocking the formation of crucial viral proteins from polyprotein precursors by the protease, and hence, to inhibit disease progression in vivo. The present compounds achieve such beneficial therapeutic effect because they contain unique structural features which impart desirable pharmacokinetic properties to the compounds. One such property is long duration of action. We have found that substitution of a heterocycle, especially imidazole, in the putative P2' position of the present compounds affords compounds which retain good enzyme binding affinity, good antiviral activity, a favorable duration of action and water solubility for good drug delivery.

When a compound of the present invention is administered to an animal infected or potentially infected with a retrovirus, viral replication is inhibited and hence disease progression is retarded. Inasmuch as the amino acid sequences of the protease binding and peptide bond cleavage sites of various retroviruses appear to be highly conserved, an inhibitor is likely to be broadly active against more than one retrovirus. Also, DNA viruses which are dependant upon virally encoded proteases, such as the hepatitis virus, may also be susceptible to such treatment.

The compounds of formula (I) are used to inhibit retroviral replication, and are useful in treating mammals, particularly human patients, who are infected with susceptible retroviruses and require such treatment. The method of treating a retroviral disease in a mammal, particularly a human, comprises internally administering (e.g. orally, parenterally, buccally, trans-dermally, rectally or by insufflation) to said mammal an effective amount of a compound of formula (I), preferably dispersed in a pharmaceutical carrier. Dosage units of the active ingredient may be selected by procedures routine to one skilled in the art, and are generally in the range of 0.01–50 mg/kg. These dosage units may be administered one to ten times daily for acute or chronic infection. Preferably the compound is administered at a level of 1–10 mg/kg, two to four times daily. No unacceptable toxicological effects are indicated when compounds of this invention are administered in the above noted dosage range.

The present invention also provides a method of treating disease states associated with HIV infection or Acquired Immune Deficiency Syndrome (AIDS), comprising administering an effective amount of a compound of formula (I), preferably dispersed in a pharmaceutical carrier.

Beneficial effects may be realized by co-administering, individually or in combination, other anti-viral agents with the protease inhibiting compounds of the present invention. Examples of anti-viral agents include nucleoside analogues, phosphonoformate, rifabutin, ribaviran, phosphonothioate oligodeoxynucleotides, castanospermine, dextran sulfate, alpha interferon and ampligen. Nucleoside analogues, which include 2',3'-dideoxycytidine(ddC), 2',3'-dideoxyadenine (ddA) and 3'-azido-2',3'-dideoxythymide (AZT), are especially useful. AZT is a preferred agent. Suitably, pharmaceutical compositions comprise an anti-viral agent, a protease inhibiting compound of the present invention, and a pharmaceutically acceptable carrier.

This invention is also a pharmaceutical formulation which comprises a compound of formula (I) and a pharmaceutically acceptable carrier. Pharmaceutical acceptable carrier are well known in the art and are disclosed, for instance, in SPROWL'S AMERICAN PHARMACY, Dittert, L. (ed.), J. B. Lippincott Co., Philadelphia, 1974, and REMINGTON'S PHARMACEUTICAL SCIENCES, Gennaro, A. (ed.), Mack Publishing Co., Easton, Pa., 1985.

Pharmaceutical compositions of the compounds of the present invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, soy bean oil, peanut oil, olive oil, glycerin, saline, ethanol, and water. Solubilizing agents, such as dimethylsulfoxide, ethanol or formamide, may also be added. Carriers, such as oils, optionally with solubilizing excipients, are especially suitable. Oils include any natural or synthetic non-ionic water-immiscible liquid, or low melting solid, which is capable of dissolving lipophilic compounds. Natural oils, such as triglycerides are representative. In fact, another aspect of this invention is a pharmaceutical composition comprising a compound of formula (I) and an oil.

Solid carriers include starch, lactose, calcium sulfate dihydrate, terra alba, magnesium stearate or stearic acid, talc, pectin, acacia, agar or gelatin. Solubilizing agents, such as dimethylsulfoxide or formamide, may also be added. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

A suitable dosage form for oral administration has been prepared by dissolving the peptide of Example 1 (312.5 mg) in dimethyl sulfoxide (1 mL) and diluting to a concentration of 12.5 mg/mL with soybean oil. A suitable dosage form for intravenous administration has been prepared by dissolving the compound of Example 1 (0.02 g) in dimethyl sulfoxide (1 mL) and diluting to 20 mL with a 70% propylene glycol/30% ethanol solution.

For rectal administration, a pulverized powder of the compounds of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

The pharmacological activity of the compounds of this invention may be demonstrated by enzyme assays to determine the inhibitory activity of the retroviral protease, by in vitro cellular-based assays to determine the ability of the compounds to penetrate cells and inhibit viral replication, and by pharmacokinetic assays to determine oral bioavailability, drug half-life and clearance. These assays are well known in the art.

ENZYME ACTIVITY

The ability of the compounds of this invention to inhibit the HIV-1 protease enzyme may be demonstrated by using the assay disclosed by Dreyer et al., *Proc. Natl. Aca. Sci., U.S.A.*, 86, 9752 (1989), Grant et al., *Biochemistry*, 30 8441 (1992), and EP-A 352 000. The $K_i$ for the compounds of this invention are in the range of 1 nM to 5 µM. Preferred compounds have $K_i$'s of less than 100 nM.

INFECTIVITY

The ability of the compounds of this invention to gain entry to cells infected with the human immunodeficiency virus, and to inhibit vital replication in vitro may be demonstrated using the assay described by Meek et al., *Nature*, 343, 90 (1990), and Petteway et al., *Trends Pharmacol. Sci*, 12, 28 (1991). The IC50 for the compounds of this invention are in the range of 0.1 to 10 µM.

CYTOTOXICITY

Cytoitoxicity is assessed by both direct microscopic examination of trypan blue stained cells (T-lymphocytes) and by the treated culture's ability to metabolize the tetrazolium salt XTT (2,3-bis[2-methoxy-4-nitro-5-sulfophenyl]-2H-tetrazolium-5-carboxanilide sodium salt), to its formazan dye. The XTT assay allows determination of the 50% toxic concentration of compounds for the cell/virus system used.

PHARMACOKINETICS

Dual jugular cannulated Sprague Dawley rats weighing 200 to 250 g were utilized in all studies. All dosing and sample collection was done from conscious rats. Before dosing, a time 0 blood sample, 300 µL, was drawn using one of the catheters. Utilizing the second catheter the rats were dosed intravenously. At 1, 10, 30, 60, 90, 120, 150, 180 and 210 min after dosing, 300 µL blood samples were drawn. The rats dosed orally were administered the compound by utilizing a 22 gauge gastric gavage needle and samples were drawn at 30, 60, 90, 120, 240, 360, 480, 600, 720 and 1440 min. The blood samples were placed in precooled tubes containing 30 mL of sodium citrate and centrifuged in a microfuge. The plasma was transferred then snap frozen on dry ice, and stored at −70° C. until analyzed.

Standard stock solutions (1 mg/mL) of inhibitor was prepared in 100% DMSO. A dilution series of the stock solutions were prepared in a total volume of 0.1 mL (pooled normal rat plasma/DMSO) to yield final concentrations of 0 and 0.5–120X the $K_i$ of the inhibitor. All dilutions were performed in triplicate. These spiked plasma solutions were extracted with 0.5 mL acetonitrile by vigorous vortexing, followed by centrifugation for 10 min. An aliquot (0.4 mL) of the supernatant was removed and dried in Eppendorf tubes using a Speed-vac. The resulting residue was redissolved in DMSO. The inhibition of the HIV-1 protease activity was assayed as follows. An aliquot of the extracted sample was added to a 50 µL mixture containing 1X MENDT buffer, 1 mM substrate and incubated at 37° C.<10 min. The reaction was then initiated by the addition of HIV-1 protease and continued at 37° C. for an additional 15 min, then quenched by the addition of TFA (0.5% final concentration). Initial rates were determined for each standard curve as the fraction of remaining enzymatic activity $(v_i/v_0)$ at each inhibitor concentration, in which $v_0$ is the velocity of the I (inhibitor concentration)=0 sample. Assuming that all of the original inhibitor in the spiked samples was extracted, the values of $v_i/v_0$ were plotted versus inhibitor concentration of the original extracted sample and fitted to the equation:

$$v_i/v_0=[AE_t-I_t-K_i+(K_i-AE_t-I_t)^{0.5}]/(2AE_t)$$

in which $E_t$ is the total enzyme concentration at time zero, $K_i$ is the apparent inhibition constant and A is the fraction of active enzyme.

Ex vivo animal plasma samples containing unknown levels of protease inhibitor were prepared and analyzed as described for the standard curve described above. The concentration of inhibitor in these samples was then determined using the $K_i$ and A parameters from the fitted standard curve according to the following equation:

$$I_t=AE_t[1-(v_i/v_0)]+K_i(v_0/v_i).$$

The data was plotted as the natural log (ln) of the plasma concentration versus time on semilogarithmic paper to generate the plasma concentration-vs-time curves. Using the IV data, the apparent terminal rate constant was determined from the linear regression analysis of the plasma concentration-vs-time curve. The elimination half-life $(t_{1/2})$ was derived by dividing ln 0.5 (=0.693) by the terminal rate constant. The area under the plasma concentration-vs-time curve (AUC) was determined by using the ln/log trapezoidal rule. $C_{max}$ represents the maximal plasma concentration and $t_{max}$, the time following drug administration at which $C_{max}$ was observed. Both values were estimated by inspection of the plasma concentration-vs-time curve. Total plasma clearance (CL) was calculated by dividing the dose by the AUC. The fraction of the oral dose available to the systemic circulation (the bioavailable fraction, F) was determined by the equation:

$$F=[AUC_{po}/DOSE_{po}]\times[DOSE_{iv}/AUC_{iv}].$$

The Examples which follow serve to illustrate this invention. The Examples are not intended to limit the scope of this invention, but are provided to show how to make and use the compounds of this invention.

In the Examples, all temperatures are in degrees Centigrade. Mass spectra were performed using fast atom bombardment (FAB) or electro-spray (ES) ionization. Melting points were taken on a Thomas-Hoover capillary melting point apparatus and are uncorrected.

NMR were recorded at 250 MHz using a Bruker AM 250 spectrometer, unless otherwise indicated. Chemical shifts are reported in ppm (δ) downfield from tetramethylsilane. Multiplicities for NMR spectra are indicated as: s=singlet, d=doublet, t=triplet, q=quartet, m=multiplet, dd=doublet of doublets, dt=doublet of triplets etc. and br indicates a broad signal. J indicates the NMR coupling constant in Hertz.

Celite® is filter aid composed of acid washed diatomaceous silica manufactured by Mansville Corp., Denver, Colo. Florisil® is an activated magnesium silicate chromatographic support and is a registered trademark of Floridon Co., Pittsburgh, Pa. Sat. indicates a saturated solution, eq indicates the proportion of a molar equivalent of reagent relative to the principal reactant.

EXAMPLE 1

Preparation of (2R,4S,5S,1'S)-2-phenylmethyl-4-hydroxy-5-(t-butoxycarbonyl)amino-6-phenyl-N-(1'-isopropyl-1'-(imidazo-2-yl))methyl-hexanamide hydrochloride a) (1'S)-1'-carbobenzyloxyamino-1'-isopropyl-1'-(imidazo-2-yl)methane Cbz-valinal (4.6 g, 1 eq) and glyoxal trimeric dihydrate (1.33 g, 1eq) were stirred in MeOH at −10° C. Ammonia was bubbled through the solution for several min and the mixture was allowed to stir for 4 h at −10° C. The mixture was allowed to warm to room temperature over 14 h, then was poured into 250 mL water. The suspension was filtered and the filter cake washed twice with water to give the title compound as a white solid (1.9 g, 36%). NMR(CD$_3$OD) δ 7.28 (5H, m), 6.89 (2H, s), 5.04 (2H, dd), 4.46 (1H, d), 2.10 (1H, m), 0.91 (3H, d), 0.70 (3H, d); MS(CI/CH$_4$) m/e 274.2 [M+H]$^+$, 230.1, 166.1, 123.1, 91.1.

b) (1'S)-1'-amino-1'-isopropyl-1'-(imidazo-2-yl)methane (1'S)-1'-carbobenzyloxyamino-1'-isopropyl-1'-(imidazo-2-yl)methane (1.9 g) was stirred in methanol over 10% Pd/C (200 mg). Hydrogen was bubbled through the solution for 1 h and the solution was maintained under a positive hydrogen atmosphere overnight. The mixture was filtered through Celite® and was evaporated to a tacky solid (720 mg, 75%). NMR(CDCl$_3$) δ 6.87 (2H, s), 3.88 (1H, d), 2.04 (1H, m), 0.81 (6H, dd); MS(DCI/NH$_3$) m/e 190.2 [M+H]$^+$.

c) (2R,4S,5S,1'S)-2-phenylmethyl-4-(t-butyldimethyl)siloxy-5-(t-butoxycarbonyl)amino-6-phenyl-N-[1'-isopropyl-1'-(imidazo-2-yl)]methyl-hexanamide To a solution of (2R,4S,5S)-2-phenylmethyl-4-(t-butylmethyl)siloxy-5-(t-butoxycarbonyl)amino-6-phenyl-hexanoic acid (200 mg, 0.38 mmol) in dichloromethane, (1'S)-1'-amino-1'-isopropyl-1'-(imidazo-2-yl)methane (48 mg, 0.35 mmol), BOP reagent (168 mg, 0.38 mmol), and triethylamine (0.053 mL, 0.38 mmol) were added. The mixture was stirred under argon overnight, and washed successively with water, 5% aqueous sodium bicarbonate, and saturated aqueous sodium chloride. The solution was dried over MgSO$_4$, filtered, and evaporated to a white solid. The solid was chromatographed (silica, 4% methanol/dichloromethane) to afford the title compound as a white solid (0.154 g, 68%). NMR(CDCl$_3$) δ 7.18 (10H, m), 6.91 (2H, d), 6.32 (1H, d), 4.69 (1H, d), 4.40 (1H, t), 3.92 (1H, q), 3.63 (1H, m), 2.84–2.31 (6H, m), 1.67 (4H, m), 1.24 (9H, s), 0.89 (9H, s), 0.74 (6H, dd), 0.05 (6H, d); MS(DCI/NH$_3$) m/e 649.6 [M+H]$^+$.

d) (2R,4S,5S,1'S)-2-phenylmethyl-4-hydroxy-5-(t-butoxycarbonyl)amino-6-phenyl-N-[1'-isopropyl-1'-(imidazo-2-yl)]methyl-hexanamide hydrochloride The compound of Example 1(c) (0.140 g) was stirred in THF at room temperature under an argon atmosphere. Tetrabutyl ammonium fluoride (0.38 mL, 6 eq) was added and the solution was stirred overnight. The mixture was diluted with water and extracted with dichloromethane (3X). The combined organic extracts were washed with water and evaporated. The residue was treated with 1 eq of methanolic HCl, concentrated, and triturated with diethyl ether and ethyl acetate to give the title compound as a white solid (95 mg, 83%). NMR(DMSO-d$_6$) δ 7.78 (1H, d), 7.16 (10H, m), 6.71 (2H, s), 6.39 (1H, d), 4.68 (1H, m), 4.52 (1H, d), 2.71 (3H, m), 2.48 (3H, m), 1.97 (1H, m), 1.61 (1H, m), 1.30 (9H, s), 0.78 (3H, d), 0.61 (3H, d); MS(DCI/NH$_3$) m/e 535.4 [M+H]$^+$.

EXAMPLE 2

Preparation of (2R,4S,5S,1'S)-2-phenylmethyl-4-hydroxy-5-(t-butoxycarbonyl)amino-6-phenyl-N-[1'-isopropyl-1'-(4-aminocarbonyl-thiazo-2-yl)]methyl-hexanamide a) Boc-valineamide To a solution of di-t-butyl-dicarbonate (7.15 g, 1 eq) in dry dichloromethane was added valinamide hydrochloride (5.0 g, 1 eq) and triethylamine (9.14 mL, 2 eq). The mixture was heated to reflux for 4 h, and cooled to room temperature. The organic layer was washed twice with water and evaporated to give the title compound (6.03 g, 85%). NMR (CDCl$_3$) δ 6.00 (1H, br), 5.54 (1H, br), 5.01 (1H, br), 3.93 (1H, dd), 2.12 (1H, m), 1.44 (9H, s), 0.92 (6H, dd).

b) Boc-valinethioamide

Boc-valineamide (0.5 g) was stirred in dry THF at room temperature under argon. Lawesson's reagent (1.56 g, 0.6 eq) was added and the mixture was stirred overnight. The solvent was evaporated and the residue chromatographed (silica, 2.5% methanol/dichloromethane) to give the title compound as a white solid (0.373 g, 70%). NMR(CDCl$_3$) δ 8.59 (1H, br s), 8.09 (1H, br s), 5.41 (1H, d (br)), 4.20 (1H, dd), 1.99 (1H, m), 1.39 (9H, s), 0.90 (6H, m).

c) (1'S)-1'-(t-butoxycarbonyl)amino-1'-isopropyl-1'-(4-carboethoxythiazo-2-yl)methane Boc-valinethioamide (0.265 g) was stirred in dry acetone under argon at −10° C. Ethylbromopyruvate (0.16 mL, 1.1 eq) was added and stirred for 1 h at −10° C. The solution was poured into a well-stirred mixture of chloroform and water and then saturated with sodium bicarbonate. The organic phase was separated and the aqueous layer extracted with chloroform. The combined organic extracts were dried over MgSO$_4$, filtered, and evaporated to an oil. The oily residue was treated with trifluoroacetic anhydride (0.16 g) and pyridine (0.2 g) in dichloromethane for 1 h at −20° C. Excess solvent was removed in vacuo and the residue dissolved in dichloromethane. The solution was washed with sat. aqueous sodium bicarbonate and 1.0N KHSO$_4$ until pH 7. The solution was dried over sodium sulfate, filtered, and evaporated to an oil which was chromatographed (silica, 4% methanol/dichloromethane) to give the title compound as a tan solid. NMR(CDCl$_3$) δ 8.04 (1H, s), 5.26 (1H, br d), 4.85 (1H, m), 4.37 (2H, q), 2.40 (1H, m), 1.41 (9H, s), 1.34 (3H, t), 0.93 (3H, d), 0.84 (3H, d).

d) (1'S)-1'-(t-butoxycarbonyl)amino-1'-isopropyl-1'-(4-carboxythiazo-2-yl)methane The compound of Example 2(c) (50 mg) was stirred in THF at 0° C. Excess 1.0N NaOH was added and the mixture was stirred for 12 h at 0° C. The mixture was diluted with 1.0N citric acid and extracted with dichloromethane (3X). The combined organic extracts were evaporated and dried in vacuo to give the title compound (0.045 g, 98%). NMR (CDCl$_3$) δ 8.08 (1H, s), 5.19 (1H, m), 4.80 (1H, m), 2.31 (1H, m), 1.38 (9H, s), 0.86 (6H, dd).

e) (1'S)-1'-(t-butoxycarbonyl)amino-1'-isopropyl-1'-(4-aminocarbonylthiazo-2-yl)methane (1'S)-1'-(t-butoxycarbonyl)amino-1'-isopropyl-1'-(4-carboxythiazo-2-yl)methane (0.078 g, 0.26 mmol) was stirred under argon in dry THF at −40° C. NMM (0.06 mL; 0.55 mM) and isobutyl chloroformate (0.034 mL; 0.26 mmol) were added. After stirring 15 min, ammonia was bubbled through the mixture for several min. The solution was warmed to room termperature and the THF evaporated. The residue was diluted with ethyl acetate and washed successively with 1.0N citric acid, 5% aqueous sodium bicarbonate, and sat. aqueous sodium chloride. The organic layer was dried over MgSO$_4$, filtered, and evaporated to a solid which was chromatographed (silica, 3% methanol/ dichloromethane) to give the title compound as a white solid (0.052 g, 67%). NMR(CDCl$_3$) δ 8.02 (1H, s), 7.14 (1H, s (br)), 6.28 (1H, s (br)), 5.24 (1H, d(br)), 4.82 (1H, m), 2.30 (1H, m), 1.39 (9H, s), 0.92 (6H, dd).

f) (2R,4S,5S,1'S)-2-phenylmethyl-4-(t-butyldimethylsiloxy) -5-(t-butoxy carbonyl)amino-6-phenyl-N-[1'-isopropyl-1'- (4-aminocarbonyl-thiazo-2-yl)]methyl-hexanamide The compound of Example 2(e) (52 mg) was stirred in neat trifluoroacetic acid for 10 min and evaporated. The residue was diluted with methanol and treated with 2 eq of conc. HCl. The solvents were evaporated and dried in vacuo to give a white solid. This solid (40 mg) was added to a solution of (2R,4S,5S)-2-phenylmethyl-4-(t-butyldimethyl) siloxy-5-(t-butoxycarbonyl)amino-6-phenyl-hexanoic acid (97 mg, 1.1 eq), DCC (38 mg, 1.1 eq), and HOBT (0.05 g, 2.2 eq) in DMF at room temperature under argon. N-methylmorpholine (0.04 mL; 2.2 eq) was added and the mixture was stirred overnight. The mixture was filtered through Celite®, evaporated, and diluted with ethyl acetate. The solution was washed successively with 1.0N citric acid, 5% aqueous sodium bicarbonate, and sat. aqueous sodium chloride. The organic layer was chromatographed (silica, 2.5% methanol/dichloromethane) to yield the title compound (60 mg, 55%). NMR(CDCl$_3$) δ 7.89 (1H, s), 7.60 (1H, d), 7.24 (10H, m), 6.82 (1H, m), 5.12 (1H, m), 4.89 (1H, m), 3.92 (1H, q), 3.81 (1H, dd), 2.73 (4H, m), 2.21 (1H, m), 1.73 (2H, m), 1.40 (9H, s), 1.23 (1H, m), 0.93 (9H, s), 0.84 (6H, dd), 0.11 (6H, d).

g) (2R,4S,5S,1'S)-2-phenylmethyl-4-hydroxy-5-(t-butoxycarbonyl)amino-6-phenyl-N-[1'-isopropyl-1'-(4-aminocarbonyl(thiazo-2-yl)]methyl-hexanamide The compound of Example 2(f) (60 mg) was stirred in dry THF under argon and tetrabutylammonium fluoride (0.50 mL, 6 eq) was added. The solution was stirred at room temperature overnight. After diluting with water, the aqueous layer was extracted with dichloromethane (3X). The combined organic extracts were washed with water, evaporated, and triturated with diethyl ether and ethyl acetate to give a tan solid. The solid was chromatographed (silica gel, 4% methanol/dichloromethane) to give the title compound as a white solid (0.022 g). NMR(CDCl$_3$) δ 5 7.90 (1H, s), 7.15 (10H, m), 6.39 (1H, d), 5.93 (1H, br s), 5.06 (1H, dd), 4.91 (1H, d), 3.90 (1H, d), 3.67 (2H, m), 2.91 (4H, m), 2.64 (1H, d), 2.13(1H, m), 1.87 (3H, m), 1.36 (9H, s), 0.83 (6H, dd); MS(DCI/NH$_3$) m/e 612 [M+NH$_4$]$^+$, 595 [M+H]$^+$, 495, 413.1, 391, 374, 356, 239.1, 202, 185.

EXAMPLE 3

Preparation of (2R,4S,5S,1'S)-2-phenylmethyl-4-hydroxy-5-(t-butoxycarbonyl)amino-6-phenyl-N-[1'-isopropyl-1'-(thiazo-2-yl)]methyl-hexanamide a) (1'S)-1'-(t-butoxycarbonyl)amino-1'-isopropyl-1'-(thiazo-2-yl)methane The compound of Example 2(c) was stirred in neat quinoline. Cu powder (0.50 g) was added and the suspension was heated to 160° C. for 2 h. After cooling to room temperature, the solution was diluted with ethyl acetate and washed with 2.0N citric acid (4X). The organic layers were combined and dried over MgSO$_4$, filtered, and evaporated to a dark oil. The oil was chromatographed (silica, 4% methanol/dichloromethane) to give the title compound as an orange oil. NMR(CDCl$_3$) δ 7.68 (1H, d), 7.19 (1H, d), 5.26 (1H, d), 4.88 (1H, m), 2.31 (1H, m), 1.43 (9H, s), 0.92 (3H, d), 0.84 (3H, d).

b) (2R,4S,5S,1'S)-2-phenylmethyl-4-hydroxy-5-(t-butoxycarbonyl)amino-6-phenyl-N-[1'-isopropyl-1'-(thiazo-2-yl)]methyl-hexanamide Following the procedure of Example 2(f)–2(g), except using the compound of Example 3(a) in place of (1'S)-1'- (t-butoxycarbonyl)amino-1'-isopropyl-1'-(4-aminocarbonylthiazo-2-yl)methane, the title compound was prepared (88%). NMR(DMSO-d$_6$) δ 8.31 (1H, d), 7.62 (1H, d), 7.49 (1H, d), 7.16 (10H, m), 2.61 (6H, m), 1.28 (9H, s), 0.89 (3H, dd); MS(DCI/NH$_3$) m/e 552.3 [M+H]$^+$, 413.2, 331.1, 183.1, 157.1, 142.0, 120.1.

EXAMPLE 4

Preparation of (2R,4S,5S,1'S)-2-phenylmethyl-4-hydroxy-5-(t-butoxycarbonyl)amino-6-phenyl-N-[1'-isopropyl-1-benzimidazo-2-yl)]methyl-hexanamide a) (1'S)-1'-carbobenzyloxyamino-1'-isopropyl-1'-(benzimidazo-2-yl)methane Cbz-valine (2.0 g, 1 eq) was stirred at −10° C. in dry THF under argon. Triethylamine (1.11 mL, 1.0 eq) was added, followed by isobutyl chloroformate (1.03 mL, 1 eq). The reaction mixture was stirred for 10 min. Phenylene diamine (0.944 g, 1.1 eq) was added slowly in 10 mL dry THF. The mixture was warmed to room temperature and stirred for 1 h. The solvents were evaporated and the residue partitioned between water and ethyl acetate. The ethyl acetate layer was washed with 5% aqueous sodium bicarbonate and brine. The organic layer was dried over MgSO$_4$, filtered, and evaporated. The residue was dissolved in glacial acetic acid and heated to 65° C. for 16 h. The solvents were evaporated and the residue diluted with water. After neutralizing with saturated aqueous sodium bicarbonate, the solid was filtered and the filter cake was washed with hexane. The solid was recrystallized from ethyl acetate and hexane. NMR(CD$_3$OD) δ 7.48–7.11 (9H, m), 5.06 (2H, q), 4.62 (1H, m), 2.27 (1H, m), 1.23 (1H, m), 1.02 (3H, d), 0.84 (3H, d).

b) (1'S)-1'-amino-1'-isopropyl-1'-(benzimidazo-2-yl)methane

The compound of Example 4(a) (2.76 g) was stirred in methanol. 10% palladium on activated carbon (Pd/C) (250 mg) was added and hydrogen gas was bubbled through the solution for 1 h. The reaction was maintained under an hydrogen atmosphere overnight. The mixture was filtered through Celite® and the solvents evaporated to give the title compound as a white solid (1.58 g, 98%). NMR(CDCl$_3$) δ 7.48–7.10 (4H, m), 4.02 (1H, d), 2.24 (1H, m), 0.96 (3H, d), 0.83 (3H, d); MS(DCI/NH$_3$) m/e 190.2 [M+H]$^+$.

c) (2R,4S,5S,1'S)-2-phenylmethyl-4-(t-butyldimethyl) siloxy-5-(t-butoxycarbonyl)amino-6-phenyl-N-[1'-isopropyl-1'-benzimidazo-2-yl]methyl-hexanamide To a solution of (2R,4S,5S)-2-phenylmethyl-4-(t-butyldimethyl)siloxy-5-(t-butoxycarbonyl)amino-6-phenyl-hexanoic acid (75 mg, 1.1 eq) in dimethyl formamide under argon, the compound of Example 4(b) (25 mg, 1.0 eq), DCC (30 mg, 1.1 eq) and HOBT (44 mg, 2.2 eq) were added. The mixture was stirred overnight, then filtered through Celite®. The solvents were evaporated and the residue was chromatographed (silica gel, 4% methanol/dichloromethane) to give the title compound (0.070 g, 78%). NMR(CDCl$_3$) δ 7.88 (1H, d), 7.30 (14H, m), 6.80 (1H, d), 4.93 (2H, m), 4.26 (1H, q), 4.00 (1H, m), 2.92 (7H, m), 2.01 (2H, m), 1.53 (9H, s), 1.20 (9H, s), 1.14 (6H, d), 0.41 (6H, d); MS(DCI/NH$_3$) m/e 699.6 [M+H]$^+$.

d) (2R,4S,5S,1'S)-2-phenylmethyl-4-hydroxy-5-(t-butoxycarbonyl)amino-6-phenyl-N-[1'-isopropyl-1'-benzimidazo-2-yl]methyl-hexanamide The compound of Example 4(c) was stirred in dry THF and tetrabutyl ammonium flouride (0.6 mL, 6 eq) was added.

The mixture was stirred under argon overnight at room temperature. The solution was diluted with water and extracted with dichloromethane (3X). The combined organic layers were washed with water and evaporated to a residue which was chromatographed (silica, 2% methanol/CH$_2$CL$_2$) to give the title compound (0.029 g, 50%). NMR(CDCl$_3$) δ 7.54 (1H, m), 7.11 (11H, m), 6.69 (4H, s), 4.98 (1H, d), 4.69 (2H, m), 3.66 (2H, m), 2.74 (5H, m), 2.31 (1H, m), 1.73 (2H, m), 1.32 (9H, s), 0.70 (6H, d); MS (DCI/NH$_3$) m/e 585.4 [M+H]$^+$, 413.3, 364.3, 296.2, 190.2, 173.1, 120.1.

EXAMPLE 5

Preparation of (2R,4S,5S,1'S)-2-phenylmethyl-4-hydroxy-5-(t-butoxycarbonyl)amino-6-phenyl-N-(1'-imidazo-2-yl)methyl-hexanamide hydrochloride a) 2-(carbobenzyloxyamino)methyl-imidazole Following the procedure of Example 1(a), except substituting Cbz-glycinal for Cbz-valinal, the title compound was prepared. NMR(CDCl$_3$) δ 0.33 (5H, s), 6.95 (2H, s), 5.95 (1H, s(br)), 5.12 (2H, s), 4.42 (2H, d); MS(DCI/NH$_3$) m/e 232.2[M+H]$^+$, 188 171.

b) (2R,4S,5S,1'S)-2-phenylmethyl-4-hydroxy-5-(t-butoxycarbonyl)amino-6-phenyl-N-(1'-imidazo-2-yl) methyl-hexanamide hydrochloride Following the procedure of Example 1(b)–1(d), except substituting the compound of Example 5(a) for (1'S)-1'-carbobenzyloxyamino-1'-isopropyl-1'-(imidazo-2-yl) methane, the title compound was prepared. NMR(CD$_3$OD) δ 7.20 (10H,m), 6.94 (2H,s), 6.11 (1H,d), 4.24 (2H,dd), 3.61 (1H,m), 3.52 (1H,m), 2.69 (4H,m), 1.66 (2H,m), 1.28 (9H, s); MS (DCI/NH$_3$) m/e 493.7 [M+H]$^+$, 475.7, 120.2, 98.2, 83.1, 69.1.

EXAMPLE 6

Preparation of (2R,4S,5S,1'S)-2-phenylmethyl-4-hydroxy-5-(t-butoxycarbonyl)amino-6-phenyl-N-[1'-methyl-1'-(imidazo-2-yl)]methyl-hexanamide hydrochloride a) (1'S)-1'-carbobenzyloxyamino-1'-methyl-1'-(imidazo-2-yl)methane Following the procedure of Example 1(a), except substituting Cbz-alanal for Cbz-valinal, the title compound was prepared. NMR(CDCl$_3$) δ 0.35 (5H,s), 6.92 (2H,s), 5.52(1H, d), 5.12 (2H,q), 4.90 (1H,q); MS(DCI/NH$_3$) m/e 246 [M+H]$^+$, 202 185.

b) (2R,4S,5S,1'S)-2-phenylmethyl-4-hydroxy-5-(t-butoxycarbonyl)amino-6-phenyl-N-[1'-methyl-1'-(imidazo-2-yl)]methyl-hexanamide hydrochloride Following the procedure of Example 1(b)–1(d), except substituting the compound of Example 6(a) for (1'S)-1'-carbobenzyloxyamino-1'-isopropyl-1'-(imidazo-2-yl) methane, the title compound was prepared. NMR(CD$_3$OD) δ 7.11 (10H, m), 6.86 (2H, s), 4.69 (1H, d), 3.62 (1H, d), 3.51 (1H, m), 2.68 (6H, m), 1.59 (2H, m), 1.30 (9H, s), 1.14 (3H, d); MS(DCI/NH$_3$) m/e 507.5 [M+H]$^+$, 489.4, 112.1.

EXAMPLE 7

Preparation of (2R,4S,5S,1'S)-2-phenylmethyl-4-hydroxy-5-(t-butoxycarbonyl)amino-6-phenyt-N-[1'-benzyl-1'-(imidazo-2-yl)]methyl-hexanamide hydrochloride a) (1'S)-1'-carbobenzyloxyamino-1'-benzyl-1'-(imidazo-2-yl)methane Following the procedure of Example 1(a), except substituting Cbz-phenylalaninal for Cbz-valinal, the title compound was prepared. NMR(CDCl$_3$) δ 7.37–7.05 (10H,m), 6.95 (2H, s br), 5.52 (1H, d), 5.05 (2M, s), 4.95 (1H, q), 3.32 (2H, d); MS(DCI/NH$_3$) m/e 322, 261, 171.

b) (2R,4S,5S,1'S)-2-phenylmethyl-4-hydroxy-5-(t-butoxycarbonyl)amino-6-phenyl-N-(1'-benzyl-1'-(imidazo-2-yl)) methyl-hexanamide hydrochloride Following the procedure of Example 1(a)–1(d), except substituting the compound of Example 7(a) for (1'S)-1'-carbobenzyloxyamino-1'-isopropyl-1'-(imidazo-2-yl) methane, the title compound was prepared. NMR(CD$_3$OD) δ 7.15 (15H, m), 6.79 (2H, s), 5.78 (1H, d), 5.04 (1H, d), 3.58 (1H, m), 3.47 (1H, m), 2.68 (8H, m), 1.59 (2H, m), 1.31 (9H, s).

EXAMPLE 8

Preparation of (2R,4S,5S,1'S)-5-(carbobenzyloxy) amino-4-hydroxy-N-(1'-isopropyl-1'-imidazol-2-yl) methyl-6-phenyl-2-phenylmethyl-hexanamide A solution of (2R,4S,5S,1'S)-5-(t-butoxycarbonyl)amino-4-hydroxy-N-(1'-isopropyl-1'-imidazol-2-yl)methyl-6-phenyl-2-phenylmethyl-hexanamide (0.086 g) in trifluoroacetic acid was stirred for 10 min, then was evaporated in vacuo. To the residue were added dimethylformamtde, benzylchloroformate (1 eq) and triethylamine (5 eq), and the resulting mixture was stirred at room temperature for 16 h. The reaction mixture was poured into H$_2$O and extracted with dichloromethane. The combined organic extracts were evaporated, and the residue was triturated with diethyl ether to afford the title compound as a white solid. NMR(CD$_3$OD) δ 7.36–6.94 (15H, m), 6.84 (2H, s), 4.99 (2H, s), 4.54 (2H, d), 3.76 (1H, m), 3.52 (1H, dd), 2.77 (5H, m), 2.04 (1H, m), 1.76 (1H, m), 1.58 (1H, m), 0.82 (3H, d), 0.66 (3H, d).

EXAMPLE 9

Preparation of (2R,4S,5S,1'S)-5-(t-butoxycarbonyl) amino-4-hydroxy-N-[1'-isopropyl-1'-(4,5-deimethyl) imidazol-2-yl]methyl-6-phenyl-2-phenylmethyl-hexanamide a) (1S)-1-carbobenzyloxyamino-1-isopropyl-1-(4,5-dimethylimidazol-2-yl)methane Cbz-Valinal (4.14 g) was stirred in methanol with 2,3-butanedione (1.54 mL, 1.0 eq). Ammonia was bubbled through the solution at –25° C. for 5 min. The cooling bath was removed and the mixture allowed to warm to 20° C. The solution was stirred for 16 h under Ar. The solvents were removed by rotary evaporation, and the residue was diluted with dichloromethane and extracted with dilute aqueous HCl. The organic layer was concentrated to afford unreacted Cbz-valinal (4.02 g). The acidic aqueous layer was basified with 1N NaOH and extracted with dichloromethane, the organic extract was concentrated and the residue purified by flash chromatography (4% methanol in dichloromethane) to provide the title compound as a white solid (50 mg). NMR(CD$_3$OD) δ 7.29 (5H, m), 5.04 (2H, dd), 4.38 (1H, d), 2.06 (6H, s), 2.01 (1H, m), 0.93 (3H, d), 0.77 (3H, d).

b) (1S)-1-(4,5-dimethylimidazol-2-yl)-2-methylpropylamine

The benzyloxycarbonyl group was cleaved by hydrogenolysis using the same procedure as described previously in Example 1(b), except using the product of 1(a) (50 mg), to afford the title compound as a white solid (24 mg, 87%). NMR(CDCl$_3$) δ 4.11 (2H, s(br)), 3.71 (1H, d), 2.06 (6H, s), 2.00 (1H, m), 0.71 (6H, dd).

c) (2R,4S,5S,1'S)-5-(t-butoxycarbonyl)amino-4-t-butyldimethylsiloxy-N-[1'-isopropyl-1'-(4,5-dimethyl) imidazol-2-yl]methyl-6-phenyl-2-phenylmethyl-hexanamide Using the procedure of Example 1(c), except substituting (2R,4 S,5S)-5-(t-butoxycarbonyl)amino-4-t- butyldimethylsiloxy-6-phenyl-2-phenylmethylhexanoic acid and (1S)-1-(4,5-dimethylimidazol-2-yl)-2-methylpropylamine (24 mg), the title compound was prepared (55 mg, 57%). NMR(CDCl$_3$) δ 7.26–6.80 (10H, m), 4.65 (1H, d), 4.24 (1H, dd), 3.87 (1H, q), 3.61 (1H, m), 2.77–2.39 (5H, m), 2.22 (1H, m), 1.98 (6H, s), 1.79 (1H, m), 1.58 (1H, m), 1.24 (9H, s), 0.85 (9H, s), 0.69 (6H, d), 0.06 (6H, d).

d) (2R,4S,5S,1'S)-5-(t-butoxycarbonyl)amino-4-hydroxy-N-[1'-isopropyl-1'-(4,5-dimethyl)imidazol-2-yl]methyl-6-phenyl-2-phenylmethyl-hexanamide By following the deprotection procedure described in Example 1(d), except using (2R,4S,5S,1'S)-5-(t-butoxycarbonyl)amino-4-t-butyldimethylsiloxy-N-[1'-isopropyl-1'-(4,5-dimethyl)imidazol-2-yl]methyl-6-phenyl-2-phenylmethyl-hexanamide (55 mg) and omitting the final treatment with methanolic HCl, the title compound was prepared (25 mg, 62%). NMR(CDCl$_3$) δ 7.29–6.88 (10H, m), 4.98 (1H, br d), 4.47 (1H, m), 4.29 (1H, m), 3.58 (2H, m), 2.84–2.51 (5H, m), 2.20 (1H, m), 2.04 (6H, s), 1.71 (2H, m), 1.38 (9H, s), 0.69 (6H, dd).

EXAMPLE 10

Preparation of (2R,4S,5S,1'S)-5-(t-butoxycarbonyl)amino-4-hydroxy-N-[1'-isopropyl-1'-(4,5-dimethyl)imidazol-2-yl]methyl-6-phenyl-2-phenylmethyl-hexanamide a) (1S)-1-carbobenzyloxyamino-1-isopropyl-1-(4-phenylimidazol-2-yl)methane Using the procedure of Example 1(a), except using Cbz-(L)-valine (2.19 g) and α-ketophenylacetaldehyde instead of glyoxal, the title compound was prepared (1.54 g, 48%). NMR(CDCl$_3$) δ 7.62 (1H, (br)), 7.24 (10H, m), 5.79 (1H, d), 5.04 (2H, dd), 4.32 (1H, dd), 2.31 (1H, m), 0.96 (3H, d), 0.79 (3H, d); MS m/e 350.4 [M+H]$^+$, 199.0.

b) (2R,4S,5S,1'S)-5-(t-butoxycarbonyl)amino-4-t-butyldimethylsiloxy-N-[1'-isopropyl-1'-(4-phenyl)imidazol-2-yl]methyl-6-phenyl-2-phenylmethyl-hexanamide Using the procedure of Example 1(b)–1(c), except using the compound of 10(a) (72 mg), the title compound was prepared (67 mg, 44%). NMR(CDCl$_3$) δ 7.70 (1H, d), 7.40–6.71 (16H, m), 4.73 (1H, d), 4.54 (1H, dd), 3.96 (1H, q), 3.69 (1H, m), 2.88–2.36 (5H, m), 1.73 (2H, m), 1.33 (9H, s), 0.91 (9H, s), 0.84 (6H, dd), 0.11 (6H, d); MS m/e 725.4 [M+H]$^+$.

c) (2R,4S,5S,1'S)-5-(t-butoxycarbonyl)amino-4-hydroxy-N-[1'-isopropyl-1'-(4-phenyl)imidazol-2-yl]methyl-6-phenyl-2-phenylmethyl-hexanamide Using the procedure of Example 9(d), except starting from (2R,4S,5S,1'S)-5-(t-butoxycarbonyl)amino-4-t-butyldimethylsiloxy-N-[1'-isopropyl-1'-(4-phenyl)imidazol-2-yl]methyl-6-phenyl-2-phenylmethyl-hexanamide (67 mg), the title compound was prepared (30 mg, 54%). NMR (CDCl$_3$) δ 8 7.52–6.67 (16H, m), 5.48 (1H, d), 3.60 (1H, q), 3.44 (1H, d), 2.60 (4H, m), 1.96 (1H, m), 1.62 (2H, m), 1.23 (9H, s), 0.73 (3H, d), 0.62 (3H, d); MS m/e 611.4 [M+H]$^+$, 242.2, 195.0, 150.2.

EXAMPLE 11

Preparation of (2R,4S,5S,1'S)-5-(t-butoxycarbonyl)amino-4-hydroxy-N-[1'-isopropyl-1'-(N'-methyl)imidazol-2-yl]methyl-6-phenyl-2-phenylmethyl-hexanamide a) (1S)-carbobenzyloxyamino-1-isopropyl-1-(N'-methylimidazol-2-yl)methane The product of Example 1(a) (273 mg, 1 mmol) was heated at 40° C. for 2 h in methyl iodide (5 mL). The reaction mixture was evaporated, and the residue was suspended in aqueous Na$_2$CO$_3$. The mixture was extracted with dichloromethane, dried (Na$_2$CO$_3$) and concentrated. The crude product was purified by flash chromatography (silica, 2% methanol/dichloromethane) to yield the title compound (200 mg, 70%). NMR(CDCl$_3$) δ 7.29 (5H, s), 6.92 (1H, s), 6.69 (1H, s), 5.94 (1H, d), 5.03 (2H, q), 4.55 (1H, dd), 3.64 (3H, s), 2.20 (1H, m), 1.01 (3H, d), 0.82 (3H, d).

b) (2R,4S,5S,1'S)-5-(t-butoxycarbonyl)amino-4-t-butyldimethylsiloxy-N-[1'-isopropyl-1'-(N'-methyl)imidazol-2-yl]methyl-6-phenyl-2-phenylmethyl-hexanamide Following the procedure of Example 1(b)–1 (c), except using the compound of 11(a) (90 mg), the title compound was prepared (104 mg; 50%). NMR(CDCl$_3$) δ 7.32–6.89 (10H, m), 6.81 (1H, s), 6.59 (1H, s), 6.08 (1H, d), 4.71 (2H, m), 3.94 (1H, q), 3.70 (1H, m), 3.25 (3H, s), 2.80–2.36 (5H, m), 2.21 (1H, m), 1.73 (2H, m), 1.31 (9H, s), 0.94 (9H, s), 0.85 (6H, dd), 0.11 (6H, s).

c) (2R,4S,5S,1'S)-5-(t-butoxycarbonyl)amino-4-hydroxy-N-[1'-isopropyl-1'-(N'-methyl)imidazol-2-yl]methyl-6-phenyl-2-phenylmethyl-hexanamide Following the procedure of Example 9(d), except using (2R,4S 5S,1'S)-5-(t-butoxycarbonyl)amino-4-t-butyldimethylsiloxy-N-[1'-isopropyl-1'-(N'-methyl)imidazol-2-yl]methyl-6-phenyl-2-phenylmethyl-hexanamide (100 mg), the title compound was prepared (74 mg, 89%). NMR(CDCl$_3$) δ 7.21–6.74 (11H, m), 6.70 (1H, s), 6.59 (1H, s), 4.95 (1H, d), 4.61 (1H, dd), 3.60 (3H, m), 3.48 (3H, s), 2.71 (5H, m), 2.06 (1H, m), 1.64 (2H, m), 1.32 (9H, s), 0.82 (3H, d), 0.63 (3H, d); MS m/e 549.3 [M+H]$^+$.

EXAMPLE 12

Preparation of (2R,4S,5S,1'S)-5-(t-butoxycarbonyl)amino-4-hydroxy-N-(1'-isopropyl-1'-imidazol-2-yl)methy-6-phenyl-2-(3-phenylpropargyl)hexanamide a) (3R,5S,1'S)-(1'-t-butoxycarbonylamino-2'-phenyl)ethyl-3-(3-phenylpropargyl)-tetrahydrofuran-2-one To a solution of lithium diisopropylamide (3.61 mL, 2.0M in THF, 2.2 eq) in THF at −78° C. under an argon atmosphere, (5S,1'S)-(1'-t-butoxycarbonylamino-2'-phenyl)ethyl-tetrahydrofuran-2-one (1.0 g, 1.0 eq) was added. After stirring at −78° C. for 15 min, hexamethylphosphoramide (1.14 mL, 2 eq) was added, and stirring was continued an additional 10 min. Phenylpropargyl bromide (1.28 g, 2.0 eq), was added and the resulting mixture was stirred at −78° C. for 2 h, then poured into dilute aqueous HCl and extracted with dichloromethane. The combined organic extracts were evaporated under reduced pressure to an oil, which was chromatographed (silica, 20% ethyl acetate/hexanes) to afford the title compound as a white solid (0.455 g, 33%). NMR(CDCl$_3$) δ 7.18 (10H, m), 4.50 (2H, m), 3.93 (1H, q), 2.79 (5H, m), 2.23 (2H, m), 1.24 (9H, s).

b) (2R,4S,5S)-5-(t-butoxycarbonyl)amino-4-t-butyldimethyl-siloxy-6-phenyl-2-(3-phenylpropargyl)hexanoic acid The title compound (496 mg, 84%) was prepared by the procedure of Evans et al., *J. Org. Chem.* 50, 4615 (1985) from the product of 12(a) (450 mg). NMR(CDCl$_3$) δ 7.49–7.10 (10H, m), 4.71 (1H, d), 3.94 (3H, m), 2.69 (4H, m), 1.90 (2H, m), 1.31 (9H, s), 0.89 (9H, s), 0.11 (6H, d).

c) (2R,4S,5S,1'S)-5-(t-butoxycarbonyl)amino-4-t-butyldimethylsiloxy-N-(1'-isopropyl-1'-imidazol-2-yl)methyl-6-phenyl-2-(3-phenylpropargyl)hexanamide Following the procedure of Example 1(c), except using (2R,4S,5S)-5-(t-butoxycarbonyl)amino-4-t- butyldimethylsiloxy-6-phenyl-2-(3-phenylpropargyl) hexanoic acid (240 mg) and (1S)-1-imidazol-2-yl-2-methylpropylamine, the title compound was prepared (244 mg, 84%). NMR(CDCl$_3$) δ 7.14 (12H, m), 6.72 (1H, d), 4.58 (1H, d), 4.49 (1H, dd), 3.92 (1H, q), 3.80 (1H, m), 2.54 (5H, m), 1.65 (2H, m), 1.20 (9H, s), 0.81 (9H, s), 0.80 (6H, dd), 0.05 (6H, d).

d) (2R,4S,5S,1'S)-5-(t-butoxycarbonyl)amino-4-hydroxy-N-(1'-isopropyl-1'-imidazol-2-yl)methyl-6-phenyl-2-(3-phenylpropargyl)hexanamide Following the procedure of Example 9(d), except using (2R,4S,5S,1'S)-5-(t-butoxycarbonyl)amino-4-t-butyldimethylsiloxy-N-(1'-isopropyl-1'-imidazol-2-yl)methyl-6-phenyl-2-(3-phenylpropargyl)hexanamide, the title compound was prepared (161 mg, 79%). NMR(CDCl$_3$) δ 7.24–6.98 (10H, m), 6.68 (2H, s), 5.20 (1H, m), 4.52 (1H, d), 3.49 (2H, m), 3.06 (1H, m), 2.56 (5H, m), 2.04 (1H, m), 1.61 (2H, m), 1.26 (9H, s), 0.68 (6H, dd); MS m/e 581.2 (M+Na)$^+$, 559.2 [M+H]$^+$, 541.4, 503.2, 485.2, 459.2, 441.2.

EXAMPLE 13

Preparation of (2R,4S,5S,1'S)-5-(isopropoxycarbonyl)amino-4-hydroxy-N-(1'-isopropyl-1'-imidazol-2-yl)methyl-6-phenyl-2-phenylmethyl-hexanamide a) (2R,4S,5S,1'S)-5-amino-4-t-butyldimethylsiloxy-N-(1'-isopropyl-1'-imidazol-2-yl)methyl-6-phenyl-2-phenylmethyl-hexanamide The product of Example 1(c) (0.20 g, 0.31 mmol) was dissolved in trifluoroacetic acid and stirred at room temperature for 5 min, adichloromethane and en dichloromethane and saturated aqueous Na$_2$CO$_3$. The organic extract was dried over Na$_2$CO$_3$, filtered and evaporated to afford the title compound (0.17 g, 100%) which was used without further purification.

b) (2R,4S,5S,1'S)-5-(isopropoxycarbonyl)amino-4-t-butyldimethylsiloxy-N-[1'-isopropyl-1'-(N'-isopropoxycarbonyl)imidazol-2-yl]methyl-6-phenyl-2-phenylmethyl-hexanamide A mixture containing the compound of 13(a) (0.17 g, 0.31 mmol), isopropyl chloroformate (0.62 mL, 1M in dichloromethane, 2 eq) and 4-dimethylaminopyridine (0.75 g, 2 eq) in dichloromethane (40 mL) was allowed to stir at room temperature overnight under an argon atmosphere. The mixture was then partitioned between dichloromethane and saturated aqueous Na$_2$CO$_3$, and the organic extract was dried over Na$_2$CO$_3$. The solvent was removed in vacuo, and the residue was purified by flash chromatography (silica, 4% methanol/dichloromethane) to afford the title compound (0.214 g, 96%). NMR(CDCl$_3$) δ 7.35–6.78 (12H, m), 6.57 (1H, d), 5.61 (1H, dd), 5.19 (1H, m), 4.86 (1H, m), 4.77 (1H, d), 3.97 (1H, q), 3.63 (1H, t), 2.88 (1H, dd), 2.70–2.48 (4H, m), 2.06 (1H, m), 2.00–1.85 (1H, m), 1.79–1.64 (1H, m), 1.45 (6H, dd), 0.94 (9H, s), 0.85 (6H, d), 0.12 (6H, d).

c) (2R,4S,5S,1'S)-5-(isopropoxycarbonyl)amino-4-hydroxy-N-(1'-isopropyl-1'-imidazol-2-yl)methyl-6-phenyl-2-phenylmethyl-hexanamide To a solution of the compound of 13(b) (0.214 g) in methanol, excess aqueous HCl (~5 eq) was added. The resulting solution was allowed to stir at room temperature overnight, and was concentrated under reduced pressure. The residue was diluted with H$_2$O, and basified with aqueous Na$_2$CO$_3$. The mixture was extracted with dichloromethane, and the combined organic extracts were dried over Na$_2$CO$_3$. The solvent was removed in vacuo, and the residue was purified by flash chromatography (silica, 4% methanol/dichloromethane) to afford the title compound (0.150 g, 97%). NMR(CDCl$_3$) δ 7.32–6.96 (13H, m), 5.48 (1H, d), 5.08 (1H, m), 5.00 (1H, s(br)), 4.87 (1H, m), 3.78 (1H, m), 3.62 (1H, m), 3.25 (1H, m), 2.96–2.67 (4H, m), 2.29 (1H, m), 1.95–1.65 (2H, m), 1.25–1.12 (6H, dd), 0.80–0.60 (6H, dd); MS m/e 521 [M+H]$^+$, 519 (M–H)$^-$.

d) (2R,4S,5S,1'S)-5-(isopropoxycarbonyl)amino-4-hydroxy-N-(1'-isopropyl-1'-imidazol-2-yl)methyl-6-phenyl-2-phenylmethyl-hexanamide hydrochloride The product of 13(c) (100 mg, 0.192 mmol) was dissolved in methanol (10 mL) and a 1M solution of HCl in ether (0.192 mL) was added. The solution was concentrated by rotary evaporation without heating, and the residue was triturated with ether and dried under vacuum to afford the title compound (104 mg, 98%). NMR(CD$_3$OD) δ 7.30 (2H, s), 7.21–6.88 (10H, m), 4.61 (1H, m), 3.65 (1H, m), 3.48 (1H, d), 2.99 (1H, m), 2.87 (1H, m), 2.74–2.56 (2H, m), 2.12 (1H, m), 1.75–1.50 (2H, m), 1.17–1.00 (6H, dd), 0.90 (3H, d), 0.64(3H, d).

EXAMPLE 14

Preparation of (2R,4S,5S,1'S)-5-(benzyloxyethoxycarbonyl) amino-4-hydroxy-N-(1'-isopropyl-1'-imidazol-2-yl)methyl-6-phenyl-2-phenylmethyl-hexanamide a) benzyloxyethyl-(4-nitro)phenylcarbonate To a solution of 2-benzyloxyethanol (2.5 g, 16.4 mmol) and bis(4-nitrophenyl)carbonate (5.0 g, 1 eq) in dichloromethane (200 mL), N-methylmorpholine (1.81 mL, 1 eq) was added. The resulting mixture was allowed to stir at room temperature for 3 d. The reaction mixture was washed successively with H$_2$O and saturated aqueous NaCl and dried over Na$_2$SO$_4$. The solvent was removed in vacuo, and the residue was purified by flash chromatography (silica, 20% ethyl acetate/hexanes) to afford the title compound (4.38 g, 84%). NMR(CDCl$_3$) δ 8.26 (2H, m), 7.34 (7H, m), 4.62 (2H, s), 4.49 (2H, t), 3.70 (2H, t).

b) (2R,4S,5S,1'S)-5-(benzyloxyethoxycarbonyl)amino-4-t-butyldimethylsiloxy-N-[1'-isopropyl-1'-(N'-benzyloxyethoxy-carbonyl)imidazol-2-yl]methyl-6-phenyl-2-phenylmethyl-hexanamide To a solution of the compound of Example 14(a) (134.5 mg, 0.24 mmol) in dichloromethane (40 mL) under an argon atmosphere, benzyloxyethyl 4-nitrophenyl carbonate (160 mg, 2 eq) and 4-dimethylaminopyridine (60 mg, 2 eq) were added. The resulting mixture was allowed to stir at room temperature overnight, and was diluted with dichloromethane. The organic extract was washed successively with aqueous Na$_2$CO$_3$, H$_2$O, aqueous Na$_2$CO$_3$ and H$_2$O, and dried over Na$_2$CO$_3$. The solvent was removed in vacuo, and the residue was purified by flash chromatography (silica, 4% methanol/dichloromethane) to afford the title compound (180 mg, 82%). NMR(CDCl$_3$) δ 7.45–6.80 (22H, m), 6.62 (1H, d), 5.60 (1H, t), 5.06 (1H, d), 4.60 (2H, s), 4.52 (2H, s), 4.50 (2H, m), 4.31 (1H, m), 4.07 (2H, m), 3.80 (2H, t), 3.68 (1H, q), 3.57 (1H, q), 2.85 (1H, m), 2.77–2.41 (4H, m), 2.09 (1H, m), 1.90 (1H, m), 1.73 (1H, m), 0.95 (9H, s), 0.81 (6H, dd), 0.11 (6H, d).

c) (2R,4S,5S,1'S)-5-(benzyloxyethoxycarbonyl)amino-4-hydroxy-N-(1'-isopropyl-1'-imidazol-2-yl)methyl-6-phenyl-2-phenylmethyl-hexanamide Following the procedure of Example 13(c), except using the compound of Example 14(b) (160 mg), the title compound was prepared (100 mg, 81%). NMR(CDCl$_3$, CD$_3$OD) δ 7.40–6.79 (17H, m), 4.55 (2H, s), 4.45 (1H, d), 4.20 (2H, m), 3.80–3.45 (5H, m), 2.95–2.66 (4H, m), 2.59 (1H, dd), 2.07 (1H, m), 1.71 (2H, m), 0.80 (3H, d), 0.68 (3H, d).

EXAMPLE 15

Preparation of (2R,4S,5S,1'S)-5-(methoxycarbonyl)amino-4-hydroxy-N-(1'-isopropyl-1'-imidazol-2-yl)methyl-6-phenyl-2-phenylmethyl-hexanamide a) (2R,4S,5S,1'S)-5-(methoxycarbonyl)amino-4-t-butyldimethylsiloxy-N-[1'-isopropyl-1'-(N'- methoxycarbonyl)imidazol-2-yl]methyl-6-phenyl-2-phenylmethyl-hexanamide

Following the procedure of Example 13(b), except using (2R,4S,5S,1'S)-5-amino-4-t-butyldimethylsiloxy-N-(1'-isopropyl-1'-imidazol-2-yl)methyl-6-phenyl-2-phenylmethyl-hexanamide, the title compound was prepared (89%). NMR(CDCl$_3$) δ 7.40–6.79 (12H, m), 6.52 (1H, d), 5.58 (1H, dd), 4.91 (1H, d), 3.96 (3H, s), 3.95 (1H, d), 3.66 (1H, t), 3.60 (3H, s), 2.85 (1H, m), 2.73–2.40 (4H, m), 2.08 (1H, m), 1.90 (1H, m), 1.69 (1H, m), 0.95 (9H, s), 0.85 (6H, dd), 0.14 (6H, d).

b) (2R,4S,5S,1'S)-5-(methoxycarbonyl)amino-4-hydroxy-N-(1'-isopropyl-1'-imidazol-2-yl)methyl-6-phenyl-2-phenylmethyl-hexanamide Following the procedure of Example 13(c), except using the compound of Example 15(a), the title compound was prepared (70%). NMR(CDCl$_3$, CD$_3$OD) δ 7.23–6.60 (12H, m), 4.38 (1H, d), 3.65 (1H, t), 3.54 (3H, s), 3.33 (1H, m), 2.95 (1H, m), 2.82–2.40 (4H, m), 1.95 (1H, m), 1.64 (2H, m), 0.69 (6H, dd).

EXAMPLE 16

Preparation of (2R,4S,5S,1'S)-5-(ethoxycarbonyl) amino-4-hydroxy-N-(1'-isopropyl-1'-imidazol-2-yl) methyl-6-phenyl-2-phenylmethyl-hexanamide a) (2R,4S,5S,1'S)-5-(ethoxycarbonyl)amino-4-t-butyldimethylsiloxy-N-[1'-isopropyl-1'-(N'-ethoxycarbonyl)imidazol-2-yl]methyl-6-phenyl-2-phenylmethyl-hexanamide Following the procedure of Example 13(b), except using (2R,4S,5S,1'S)-5-amino-4-t-butyldimethylsiloxy-N-(1'-isopropyl-1'-imidazol-2-yl)methyl-6-phenyl-2-phenylmethyl-hexanamide and ethylchloroformate, the title compound was prepared (90%). NMR(CDCl$_3$) δ 7.35–6.77 (12H, m), 6.55 (1H, d), 5.60 (1H, dd), 4.86 (1H, d), 4.41 (2H, m), 4.15–3.90 (3H, m), 3.66 (1H, t), 2.87 (1H, m), 2.75–2.45 (4H, m), 2.08 (1H, m), 1.92 (1H, m), 1.70 (1H, m), 1.45 (3H, t), 1.18 (3H, t), 0.98 (9H, s), 0.85 (6H, dd), 0.13 (6H, d).

b) (2R,4S,5S,1'S)-5-(ethoxycarbonyl)amino-4-hydroxy-N-(1'-isopropyl-1'-imidazol-2-yl)methyl-6-phenyl-2-phenylmethyl-hexanamide Following the procedure of Example 13(c), except using the compound of Example 16(a), the title compound was prepared (95%). NMR(CDCl$_3$, CD$_3$OD) δ 7.25–6.75 (12H, m), 4.43 (1H, d), 3.95 (2H, q), 3.61 (1H, q), 3.40 (1H, m), 2.85 (1H, m), 2.80–2.40 (4H, m), 2.05 (1H, m), 1.61 (2H, t), 1.11 (3H, t), 0.72 (3H, d), 0.55 (3H, t).

EXAMPLE 17

Preparation of (2R,4S,5S,1'S)-5-(t-butoxycarbonyl) amino-4-hydroxy-N-(1'-isopropyl-1'-imidazol-2-yl) methyl-6-phenyl-2-(3phenyl-2-propenyl)hexanamide a) (3R,5S,1'S)-(1'-t-butoxycarbonylamino-2'-phenyl)ethyl-3-(3-phenylprop-2-enyl)-tetrahydrofuran-2-one Following the procedure of Example 12(a), except using cinnamyl bromide (0.485 mL) as the alkylating agent, the title compound was prepared (0.51 g, 75%). NMR(CDCl$_3$) δ 7.35–7.10 (10H, m), 6.43 (1H, d), 6.09 (1H, m), 4.60 (1H, m), 4.48 (1H, q), 4.00 (1H, t (br)), 2.96–2.55 (4H, m), 2.53–2.21 (2H, m), 2.05 (1H, m), 1.35 (9H, s).

b) (2R,4S,5S)-5-(t-butoxycarbonyl)amino-4-t-butyldimethyl-siloxy-6-phenyl-2-(3-phenyl-2-propenyl) hexanoic acid Following the procedure of Example 12(b), except using the compound of Example 17(a), the title compound was prepared (77%). NMR(CDCl$_3$) δ 7.40–7.05 (10H, m), 6.48–6.00 (4H, m), 4.78 (1H, d), 3.94 (1H, q), 3.80 (1H, m), 2.89 (1H, m), 2.83–2.26 (4H, m), 1.90 (1H, m), 1.59 (1H, m), 1.28 (9H, s), 0.90 (9H, s), 0.08 (6H, d).

c) (2R,4S,5S,1'S)-5-(t-butoxycarbonyl)amino-4-t-butyldimethylsiloxy-N-(1'-isopropyl-1'-imidazol-2-yl) methyl-6-phenyl-2-(3-phenyl-2-propenyl)hexanamide Following the procedure of Example 1(c), except using the compound of 17(b), the title compound was prepared (82%). NMR(CDCl$_3$) δ 7.35–7.15 (10H, m), 7.14–6.85 (2H, m), 6.73 (1H, s), 6.20 (1H, d), 6.10–5.88 (1H, m), 4.78 (1H, d), 4.65 (1H, t), 3.97 (1H, q), 3.76 (1H, m), 2.77 (2H, d), 2.50–2.25 (2H, m), 2.12 (1H, m), 1.70 (1H, m), 1.63 (1H, m), 1.36 (9H, s), 0.92 (9H, s), 0.81 (6H, d), 0.09 (6H, d).

d) (2R,4S,5S,1'S)-5-(t-butoxycarbonyl)amino-4-hydroxy-N-(1'-isopropyl-1'-imidazol-2-yl)methyl-6-phenyl-2-(3-phenyl-2-propenyl)hexanamide Following the procedure of Example 9(d), except using the compound of 17 (c), the title compound was prepared (90%). NMR(CDCl$_3$, CD$_3$OD) δ 7.30–7.00 (10H, m), 6.71 (2H, s), 6.26 (1H, d), 6.41 (1H, m), 3.66 (1H, d), 3.50 (1H, d), 2.88–2.45 (4H, m), 2.36 (1H, m), 2.23 (1H, m), 2.06 (1H, m), 1.70 (2H, m), 1.34 (9H, s), 0.88 (3H, d), 0.74 (3H, d). MS m/e 561 [M+H]$^+$.

EXAMPLE 18

Preparation of (2R,4S,5S,1'S)-5-(t-butoxycarbonyl) amino-4-hydroxy-N-[1'-isopropyl-1'-(4-nitroimidazol-2-yl)]methyl-6-phenyl-2-phenylmethyl-hexanamide a) (1S)-N-(1-(imidazol-2-yl)-2-methyl)propylacetamide To a solution of the compound of Example 1(b) (175 mg) in dichloromethane (10 mL) at 0° C. was added diisopropylethylamine (355 mg, 2.75 mmol) followed by acetyl chloride (215 mg, 2.75 mmol). The resulting mixture was stirred overnight, washed with saturated aqueous Na$_2$CO$_3$, and concentrated. The residue was treated with methanol, stirred overnight and concentrated under reduced pressure to afford the title compound (181 mg, 78%) as a white solid. NMR(CD$_3$OD) δ 6.95 (2H, s), 4.72 (1H, d, J=6 Hz), 2.35–2.10 (1H, m), 1.98 (3H, s), 0.98 (3H, d, J=5, 3 Hz), 0.82 (3H, d, J=5 Hz).

b) (1S)-N-(1-(4-nitroimidazol-2-yl)-2-methyl) propylacetamide

The compound of Example 18(a) (290 mg, 1.60 mmol) was dissolved in cold concentrated H$_2$SO$_4$ (2 mL), and after stirring for 15 min, 90% HNO$_3$ (0.4 mL) was added dropwise. The resulting mixture was slowly warmed to 40° C. and stirred for 2 h. The mixture was then poured onto ice, and the pH was adjusted to 4 by the addition of solid NaHCO$_3$. The mixture was extracted with ethyl acetate (6x), and the combined organic extracts were dried over MgSO$_4$ and concentrated under reduced pressure to afford the title compound (153 mg, 42%). NMR(CD$_3$OD) δ 7.98 (1H, s), 4.70 (1H, d, J=6 Hz), 2.35–2.15 (1H, m), 1.98 (3H, s), 0.95 (3H, d, J=5 Hz), 0.85 (3H, d, J=5 Hz); MS m/e 475.2 (2M+Na)+, 249.2 (M+Na)+, 227.2 [M+H]$^+$, 185.2, 168.0.

c) (1S)-1-(4-nitroimidazol-2-yl)-2-methylpropylamine, dihydrochloride salt

A mixture of the compound of Example 18(b) (153 mg, 0.68 mmol) in 6N HCl (2 mL) was heated at 90° C. for 12 h, cooled and concentrated under reduced pressure. The title compound was obtained (138 mg, 80%) and used without further purification. NMR(CD$_3$OD) δ 8.12 (1H, s), 4.30 (1H, d, J=4 Hz), 2.45–2.30 (1H, m), 1.12 (3H, d, J=4 Hz), 0.90 (3H, d, J=4 Hz).

d) (2R,4S,5S,1'S)-5-(t-butoxycarbonyl)amino-4-t-butyldimethylsiloxy-N-[1'-isopropyl-1'-(4-nitroimidazol-2-yl)]methyl-6-phenyl-2-phenylmethyl-hexanamide Following the procedure of Example 1(c), except using (2R,4S,5S)-5-(t-butoxycarbonyl)amino-4-t-butyl dimethylsiloxy-6-phenyl-2-phenylmethylhexanoic acid and (1S)-1-(4-nitroimidazol-2-yl)-2-methylpropylamine, the title compound was prepared. NMR(CDCl$_3$) δ 7.30–6.90 (10H, m), 6.60 (1H, d, J=4 Hz), 4.70 (1H, d, J=5 Hz), 4.40 (1H, t, J=4 Hz), 3.90 (1H, q, J=4 Hz), 3.75 (1H, dd, J=8, 3 Hz), 2.75–2.30 (6H, m), 1.80–1.50 (2H, m), 1.25 (9H, s), 0.85 (9H, s), 0.70 (6H, m), 0.05 (6H, d, J=4 Hz).

e) (2R,4S,5S,1'S)-5-(t-butoxycarbonyl)amino-4-hydroxy-N-[1'-isopropyl-1'-(4-nitroimidazol-2-yl]methyl-6-phenyl-2-phenylmethyl-hexanamide Following the deprotection procedure of Example 1(d), except using the compound of Example 18(d), the title compound was prepared. NMR(CD$_3$OD) δ 7.90 (1H, s), 7.40–6.90 (10H, m), 4.53 (1H, d, J=6 Hz), 3.70 (1H, m), 3.50 (1H, m), 2.90–2.60 (5H, m), 2.00 (1H, m), 1.90–1.55 (2H, m), 1.49 (9H, s), 0.85 (3H, d, J=4 Hz), 0.70 (d, 3H, J=4 Hz); MS m/e 602.4 (M+Na)+, 580.4 [M+H]$^+$, 524.4, 480.4

EXAMPLE 19

Preparation of (2R,4S,5S,1'S)-5-(t-butoxycarbonyl) amino-4-hydroxy-N-(1'-ethyl-1'-imidazol-2-yl) methyl-6-phenyl-2-phenylmethyl-hexanamide a) (1S)-1-carbobenzyloxyamino-1-ethyl-1-(imidazol-2-yl) methane Following the procedure of Example 1(a), except using Cbz-(L)-α-ethylglycinal in place of valinal, the title compound was prepared. NMR (CDCl$_3$) δ 7.45–7.10 (5H, m), 6.90 (2H, s), 5.65 (1H, d, J=6 Hz), 5.10–4.95 (2H, m), 4.40 (1H, q, J=5 Hz), 2.00–1.70 (2H, m), 1.00–0.80 (3H, m).

b) (1S)-(1-imidazol-2-yl)propylamine

Following the procedure of Example 1(b), except using the compound of Example 19(a), the title compound was prepared. NMR(CDCl$_3$) δ 6.90 (2H, s), 5.00–4.50 (2H, br s), 4.00 (1H, t, J=5 Hz), 2.00–1.70 (2H, m), 1.00–0.80 (3H, m).

c) (2R,4S,5S,1'S)-5-(t-butoxycarbonyl)amino-4-t-butyldimethylsiloxy-N-[1'-ethyl-1'-imidazol-2-yl]methyl-6-phenyl-2-phenylmethyl-hexanamide Following the procedure of Example 1 (c), except using (2R,4S,5S)-5-(t-butoxycarbonyl)amino-4-t-butyldimethylsiloxy-6-phenyl-2-phenylmethylhexanoic acid and the compound of Example 19(c), the title compound was prepared. NMR(CDCl$_3$) δ 7.35–6.90 (10H, m), 6.78 (2H, s), 6.20 (d, J=5 Hz), 4.80–4.65 (2H, m), 4.05 (1H, q, J=5 Hz), 3.72 (1H, dd, J=10, 3 Hz), 2.90–2.50 (5H, m), 2.10–2.05 (1H, m), 1.90–1.65 (3H, m), 1.40 (9H, s), 0.95 (9H, s), 0.90–0.85 (3H, m), 0.50 (6H, s).

d) (2R,4S,5S,1'S)-5-(t-butoxycarbonyl)amino-4-hydroxy-N-[1'-ethyl-1'-imidazol-2-yl]methyl-6-phenyl-2-phenylmethyl-hexanamide Following the procedure of Example 9(d), except using the compound of Example 19(c), the title compound was prepared. NMR(CD$_3$OD) δ 7.40–7.00 (10H, m), 6.85 (2H, s), 3.60–3.50 (2H, m), 2.95–2.60 (5H, m), 1.95–1.52 (4H, m), 1.48–1.26 (9H, m), 0.8–0.9 (3H, m). MS m/e 521.2 [M+H]$^+$; 503.4, 447.4.

EXAMPLE 20

Preparation of (2R,4S,5S,1'S)-5-(t-butoxycarbonyl) amino-4-hydroxy-N-(1'-propyl-1'-imidazol-2-yl) methyl-6-phenyl-2-phenylmethyl-hexanamide Following the procedure of Example 19(a)–19(d), except substituting Cbz-(L)-α-propylglycinal for Cbz-(L)-α-ethylglycinal, the title compound was prepared. Data for the intermediates of this synthesis were:

a) (1S)-1-carbobenzyloxyamino-1-propyl-1-(imidazol-2-yl) methane. NMR(CDCl$_3$) δ 7.40–7.10 (10H, m), 6.65 (2H, s), 5.55 (1H, d, J=6 Hz), 5.10–4.90 (2H, m), 4.65 (1H, q, J=5 Hz), 2.05–1.93 (1H, m), 1.90–1.75 (1H, m), 1.45–1.20 (4H, m), 0.95–0.85 (3H, m).

b) (1S)-1-(imidazol-2-yl)butylamine. NMR(CDCl$_3$) δ 6.90 (2H, s), 5.10–4.40 (2H, s(br)), 4.05 (1H, t, J=5 Hz), 1.90–1.55 (2H, m), 1.45–1.20 (4H, m), 0.95–0.80 (3H, m).

c) (2R,4S,5S,1'S)-5-(t-butoxycarbonyl)amino-4-t-butyldimethylsiloxy-N-[1'-propyl-1'-imidazol-2-yl]methyl-6-phenyl-2-phenylmethyl-hexanamide. NMR(CDCl$_3$) δ 7.35–7.00 (10H, m), 6.78 (2H, s), 6.22 (1H, d, J=5 Hz), 4.85–4.68 (2H, m), 4.00 (1H, q, J=3 Hz), 3.75 (1H, dd, J=10, 3 Hz), 2.80–2.50 (5H, m), 2.12–1.95 (1H, m), 1.90–1.60 (3H, m), 1.40–1.20 (13H, m), 0.90 (9H, s), 0.87–0.80 (3H, m), 0.07 (6H, s).

d) (2R,4S,5S,1'S)-5-(t-butoxycarbonyl)amino-4-hydroxy-N-[1'-propyl-1'-imidazol-2-yl]methyl-6-phenyl-2-phenylmethyl-hexanamide. NMR(CD$_3$OD) δ 7.40–7.00 (10H, m), 6.90 (2H, s), 3.78–3.50 (2H, m), 2.90–2.60 (5H, m), 1.90–1.55 (4H, m), 1.45–1.20 (13H, m); MS m/e 535.4 [M+H]$^+$.

EXAMPLE 21

Preparation of (2R,4S,5S,1'S)-5-(t-butoxycarbonyl) amino-4-hydroxy-N-[1'-isopropyl-1'-(4-bromoimidazol-2-yl)]methyl-6-phenyl-2-phenylmethyl-hexanamide a) (1S)-N-1-(4bromoimidazol-2-yl)-2methylpropylacetamide and (1S)-N-1-(4,5-dibromoimidazol-2-yl)-2-methylpropylacetamide To a solution of (1S)-N-1-imidazol-2-yl-2-methylpropylacetamide (1.58 g, 8.73 mmol) in 95% ethanol (30 mL), 2,4,4,6-tetrabromocyclohexadienone (3.93 g, 9.60 mmol) was added. The resulting mixture was stirred at room temperature for 30 min, and was concentrated in vacuo. The residue was dissolved in dichloromethane, washed with aqueous NaHCO$_3$ and dried over Na$_2$SO$_4$. The solvent was removed in vacuo, and the residue was purified by flash chromatography to afford the title compound (650 mg, 29%). NMR(CDCl$_3$) δ 7.70 (1H, d, J=7 Hz), 6.85 (1H, s), 4.67 (1H, t, J=7 Hz), 2.35–2.25 (1H, m), 1.95 (3H, s), 1.05 (3H, d, J=5 Hz), 0.80 (3H, d, J=5 Hz).

Also isolated was (1S)-N-1-(4,5-dibromoimidazol-2-yl)-2-methylpropylacetamide (50 mg, 8%): NMR(CDCl$_3$) δ 4.68 (1H, t, J=7 Hz), 2.38–2.25 (1H, m), 2.05 (3H, s), 1.05 (3H, d, J=5 Hz) 0.85 (3H, d, J=5 Hz); MS m/e 340.0 [M+H]$^+$, 280.8.

b) (1S)-1-(4-bromoimidazol-2-yl)-2-methylpropylamine, dihydrochloride

Following the procedure of Example 18(c), except using (1S)-N-1-(4-bromoimidazol-2-yl)-2-methylpropylacetamide, the title compound was prepared. NMR(CD$_3$OD) δ 7.60 (1H, s), 4.35 (1H, d, J=7 Hz), 2.50–2.38 (1H, m), 1.10 (3H, d, J=5 Hz), 0.82 (3H, d, J=5 Hz).

c) (2R,4S,5S,1'S)-5-(t-butoxycarbonyl)amino-4-t-butyldimethylsiloxy-N-[1'-isopropyl-1'-(4-bromoimidazol-2-yl)]methyl-6-phenyl-2-phenylmethyl-hexanamide Following the procedure of Example 1(c), except using (2R,4S,5S)-5-(t-butoxycarbonyl)amino-4-t-butyldimethylsiloxy-6-phenyl-2-phenylmethylhexanoic acid and (1S)-1-(4-bromoimidazol-2-yl)-2-methylpropylamine dihydrochloride, the title compound was prepared. NMR(CDCl$_3$) δ 7.40–7.00 (10H, m), 6.70 (1H, s), 6.45 (1H, d, J=5 Hz), 4.80 (1H, d, j=6 Hz), 4.40 (1H, t, J=5 Hz), 4.02 (1H, q, J=4 Hz), 3.78 (1H, dd, J=7, 2 Hz), 2.90–2.30 (9H, m), 1.85–1.60 (2H, m), 1.45 (9H, s), 1.00 (9H, s), 0.85 (6H, t, J=4 Hz), 0.10 (6H, d, J=6 Hz).

d) (2R,4S,5S,1'S)-5-(t-butoxycarbonyl)amino-4-hydroxy-N-[1'-isopropyl-1'-(4-bromoimidazol-2-yl)]methyl-6-phenyl-2-phenylmethyl-hexanamide Following the procedure of Example 9(d), except using (2R,4S,5S,1'S)-5-(t-butoxycarbonyl)amino-4-t-butyldimethyl-siloxy-N-[1'-isopropyl-1'-(4-bromoimidazol-2-yl)]methyl-6-phenyl-2-phenylmethyl-hexanamide, the title compound was prepared. NMR(CDCl$_3$) δ 7.40–7.00 (10H, m), 6.70 (1H, s), 6.55 (1H, m), 4.90 (1H, d, J=5 Hz), 4.50 (1H, t, J=5 Hz), 3.75–3.55 (2H, m), 2.95–2.65 (5H, m), 2.40–2.25 (1H, m), 1.90–1.60 (2H, m), 1.48 (9H, s), 0.80 (6H, t, J=6 Hz). MS m/e 613.2 [M+H]$^+$; 535.2.

EXAMPLE 22

Preparation of (2R,4S,5S,1'S)-5-(t-butoxycarbonyl) amino-4-hydroxy-N-[1'-isopropyl-1'-(4-dibromoimidazol-2-yl)]methyl-6-phenyl-2-phenylmethyl-hexanamide Following the procedures of Examples 18(c)–18(d) and 9(d), except substituting (1S)-N-1-(4,5-dibromoimidazol-2-yl)-2-methylpropylacetamide for (1S)-N-(1-4-nitroimidazol-2-yl)-2methyl)propylacetamide, the title compound was prepared. Analytical data for the intermediates of this synthesis were:

a) (1S)-1-(4,5-dibromoimidazol-2-yl)-2-methylpropylamine, dihydrochloride. NMR(CD$_3$OD) δ 4.10–3.90 (1H, br s), 2.30–2.10 (1H, s(br)), 1.10 (3H, d, J=5 Hz), 0.85 (3H, d, j=5 Hz).

b) (2R,4S,5S,1'S)-5-(t-butoxycarbonyl)amino-4-t-butyldimethylsiloxy-N-[1'-isopropyl-1'-(4,5-dibromoimidazol-2-yl)]methyl-6-phenyl-2-phenylmethyl-hexanamide. NMR (CDCl$_3$) δ 7.40–6.90 (10H, m), 6.38 (1H, d, J=5 Hz), 4.80–4.50 (3H, m), 4.00 (1H, q, J=5 Hz), 3.72 (1H, dd, J=7, 2 Hz), 2.85–2.50 (5H, m), 2.30 (1H, br s), 2.20–2.05 (1H, m), 1.85–1.65 (2H, m), 1.38 (9H, s), 0.90 (9H, s), 0.80–0.60 (6H, m), 0.10 (6H, d, J=3 Hz).

c) (2R,4S,5S,1'S)-5-(t-butoxycarbonyl)amino-4-hydroxy-N-[1'-isopropyl-1'-(4,5-dibromoimidazol-2-yl)]methyl-6-phenyl-2-phenylmethyl-hexanamide. NMR(CDCl$_3$) δ 7.35–6.85 (10H, m), 6.65 (1H, br s), 4.92 (1H, d, J=4 Hz), 4.50 (1H, m), 3.72–3.50 (2H, m), 2.98–2.63 (5H, m), 2.15–2.02 (1H, m), 1.90–1.70 (2H, m), 1.40 (9H, s); MS m/e 693.0 [M+H]$^+$; 637, 619, 593, 575, 291.

EXAMPLE 23

Preparation of (2R,4S,5S,1'S)-5-(t-butoxycarbonyl) amino-4-hydroxy-N-[1'-isopropyl-1'-(4-methylimidazol-2-yl)]methyl-6-phenyl-2-phenylmethyl-hexanamide a) (1S)-1-carbobenzyloxyamino-1-isopropyl-1-(4-methylimidazol-2-yl)methane.

Cbz-(L)-valinal (1.0 g, 3.9 mmol) and pyruvaldehyde (4.3 mmol, 40% in H$_2$O) were dissolved in methanol (10 mL) and chilled in an ice bath. Concentrated aqueous ammonia (2 mL) was added and the reaction mixture was stirred at 20° C. overnight. The solvent was removed in vacuo and the residue dissolved in 5% HCl (50 mL) and extracted with ethyl acetate (3×20 mL). The aqueous layer was basified to pH 10 with solid Na$_2$CO$_3$. A tan solid (463 mg) precipitated. The solid was purified by flash chromatography (silica, 2%–3% methanol/dichloromethane) to yield the title compound as a white solid (180 mg, 16%). mp 163°–164° C.; NMR (CDCl$_3$) δ 7.45–7.35 (5H, m), 6.60 (1H, s), 6.00 (1H, d, J=4 Hz), 5.05 (2H, q, J=4 Hz), 4.40 (1H, t, J=4 Hz), 2.45–2.30 (1H, m), 2.20 (3H, s), 0.95 (3H, d, J=4 Hz), 0.80 (3H, d, J=4 Hz); MS m/e 575.4 (2M+H)$^+$, 288.0 [M+H]$^+$.

b) (2R,4S,5S,1'S)-5-(t-butoxycarbonyl)amino-4-t-butyldimethylsiloxy-N-[1'-isopropyl-1'-(4-methylimidazol-2-yl)]methyl-6-phenyl-2-phenylmethyl-hexanamide Following the procedure of Example 1(b)–1 (c), except using (2R,4S,5S)-5-(t-butoxycarbonyl)amino-4-t-butyldimethylsiloxy-6-phenyl-2-phenylmethylhexanoic acid and the compound of Example 23(a), the title compound was prepared. NMR(CDCl$_3$) δ 7.37–6.90 (10H, m), 6.45 (1H, s), 6.38 (1H, d, J=3 Hz), 4.75 (1H, d, J=5 Hz), 4.40 (1H, t, J=5 Hz), 3.95 (1H, q, J=4 Hz), 3.72–3.68 (1H, m), 2.90–2.70 (4H, m), 2.60–2.48 (1H, m), 2.45–2.30 (1H, m), 2.17 (3H, s), 1.90–1.80 (1H, m), 1.75–1.62 (1H, m), 1.40 (9H, s), 0.95 (9H, s), 0.75 (6H, t, J=3 Hz), 0.10 (6H, d, J=2 Hz).

c) (2R,4S,5S,1'S)-5-(t-butoxycarbonyl)amino-4-hydroxy-N-[1'-isopropyl-1'-(4-methylimidazol-2-yl)]methyl-6-phenyl-2-phenylmethyl-hexanamide Following the procedure of Example 9(d), except using the compound of Example 23(b), the title compound was prepared. NMR(CDCl$_3$) δ 7.38–7.00 (10H, m), 6.52 (1H, s), 4.92 (1H, d, J=5 Hz), 4.42 (1H, t, J=4 Hz), 3.72–3.55 (2H, m), 2.95–2.65 (5H, m), 2.35–2.20 (1H, m), 2.18 (3H, s), 1.75 (2H, br s), 1.42 (9H, s), 0.75 (6H, d, J=3 Hz); MS m/e 549.2 [M+H]$^+$.

EXAMPLE 24

Preparation of (2R,4S,5S,1'S)-5-(t-butoxycarbonyl) amino-4-hydroxy-N-[1'-isopropyl-1'-(4-trifluoromethylimidazol-2-yl)]methyl-6-phenyl-2-phenylmethyl-hexanamide a) (1S)-1-carbobenzyloxyamino-1-isopropyl-1-(4-trifluoromethylimidazol-2-yl)methane.

Sodium acetate trihydrate (5.35 g, 2.2 eq) was dissolved in water (16 mL) and 1,1 dibromotrifluoroacetone (5.31 g, 1.1 eq) was added. The solution was stirred for 30 min at 90° C. The solution was cooled to 0° C. and poured into a 0° C. solution of Cbz-Valinal (4.22 g, 1.0 eq) in anhydrous methanol (80 mL). Concentrated ammonium hydroxide (22 mL) was added and the mixture stirred overnight at room temperature. The solvents were evaporated to give a white precipitate which was covered with 150 mL of water. The suspension was filtered and the solid washed twice with water. The white solid was dissolved in ethyl acetate, dried over sodium sulfate, filtered, and evaporated to a white solid (5.24 g, 86%). $^1$HNMR(CD$_3$OD) δ 7.45 (1H, s), 7.40–7.20 (5H, m), 5.05 (2H, q, J=4 Hz), 4.50 (1H, d, J=4 Hz), 2.38–2.10 (1H, m), 1.00 (3H, d, J=4 Hz), 0.80 (3H, d, J=4 Hz), $^{13}$CNMR(CD$_3$OD, $^1$H-decoupled) δ 18.9, 19.4, 67, 117(q, J=3 Hz), 123.2(q, J=266 Hz), 128.7, 129.3, 133(q, J=39 Hz), 138.0, 151.7; MS m/e 342.0 [M+H]$^+$.

b) (2R,4S,5S,1'S)-5-(t-butoxycarbonyl)amino-4-t-butyl-dimethylsiloxy-N-[1'-isopropyl-1'-(4-trifluoromethylimidazol-2-yl)]methyl-6-phenyl-2-phenylmethyl-hexanamide Following the procedure of Example 1(b)–1(c), except using the compound of Example 24(a) and (2R,4S,5S)-5-(t-butoxycarbonyl)amino-4-t-butyldimethylsiloxy-6-phenyl-2-phenylmethylhexanoic acid, the title compound was prepared. NMR(CDCl$_3$) δ 7.35–6.95 (11 H, m), 6.50 (1H, d, J=4 Hz), 4.75 (1H, d, J=6 Hz), 4.25 (1H, t, J=4 Hz), 3.95 (1H, q, J=4 Hz), 3.80–3.68 (1H, m), 2.90–2.40 (5H, m), 1.80–1.60 (2H, m), 1.35 (9H, s), 0.90 (9H, s), 0.80 (3H, d, J=3 Hz), 0.70 (3H, d, J=3 Hz), 0.05 (6H, d, J=2 Hz).

c) (2R,4S,5S,1'S)-5-(t-butoxycarbonyl)amino-4-hydroxy-N-[1'-isopropyl-1'-(4-trifluoromethylimidazol-2-yl)] methyl-6-phenyl-2-phenylmethyl-hexanamide Following the procedure of Example 9(d), except using the compound of Example 24(b), the title compound was prepared. NMR(CDCl₃) δ 7.35 (1H, s), 7.25–6.90 (10H, m), 4.53 (1H, d, J=5 Hz), 3.68 (1H, t, J=4 Hz), 3.52 (1H, d, J=6 Hz), 2.90–2.55 (5H, m), 2.10–1.95 (1H, m), 1.85–1.70 (1H, m), 1.65–1.50 (1H, m), 1.40–1.25 (9H, m), 0.90 (3H, d, J=4 Hz), 0.65 (3H, d, J=4 Hz); MS m/e 603.2 [M+H]⁺, 529.2, 503.2.

EXAMPLE 25

Preparation of (2R,4S,5S,1'S)-5-(t-butoxycarbonyl) amino-4-hydroxy-N-methyl-N-(1'-isopropyl-1'-imidazol-2-yl)methyl-6-phenyl-2-phenylmethyl-hexanamide a) (1S)-1-carbobenzyloxyamino-1-isopropyl -1-(imidazol-2-yl)methane Following the procedure of Example 1(a), except substituting N-methyl-Cbz-(L)-valinal for Cbz-(L)-valinal, the title compound was prepared. NMR(CDCl₃) δ 7.45–7.30 (5H, m), 6.90 (2H, s), 5.12 (2H, s), 4.60 (1H, d, J=6 Hz), 2.95 (3H, s), 2.70–2.53 (1H, m), 1.02 (3H, d, J=3 Hz), 0.85 (3H, d, J=3 Hz).

b) (1S)-1-methylamino-1-isopropyl-1-(imidazol-2-yl)methane

Following the procedure of Example 1(b), except using the compound of Example 25(a), the title compound was prepared. NMR(CDCl₃) δ 6.95 (2H, s), 3.52 (1H, d, J=3 Hz), 2.30 (3H, s), 2.10–1.90 (1H, m), 0.98 (3H, d, J=3 Hz), 0.82 (3H, d, J=3 Hz).

c) (2R,4S,5S,1'S)-5-(t-butoxycarbonyl)amino-4-t-butyldimethylsiloxy-N-methyl-N-(1'-isopropyl-1'-imidazol-2-yl)methyl-6-phenyl-2-phenylmethyl-hexanamide Following the procedure of Example 1(c), except using the compound of Example 25(b), the title compound was prepared. NMR(CDCl₃) δ 7.40–6.72 (12H, m), 4.82 (1H, d, J=5 Hz), 3.95 (1H, q, j=4 Hz), 3.82–3.75 (1H, m), 2.95–2.70 (5H, m), 2.51 (2H, s), 2.50–2.38 (1H, m), 2.08 (1H, s), 1.87–1.68 (2H, m), 1.38 (9H, s), 0.95 (9H, s), 0.88 (3H, d, J=3 Hz), 0.75 (3H, d, J=3 Hz), 0.05 (6H, d, J=7 Hz).

d) (2R,4S,5S,1'S)-5-(t-butoxycarbonyl)amino-4-hydroxy-N-methyl-N-(1'-isopropyl-1'-imidazol-2-yl)methyl-6-phenyl-2-phenylmethyl-hexanamide Following the procedure of Example 9(d), except using the compound of Example 28(c), the title compound was prepared. NMR(CDCl₃) δ 7.35–6.82 (12H, m), 4.90–4.72 (1H, m), 3.70–3.00 (2H, m), 2.92–2.50 (8H, m), 1.90–1.60 (2H, m), 1.40–1.30 (9H, m), 0.95–0.70 (6H, m). MS m/e 549.2 [M+H]⁺.

EXAMPLE 26

Preparation of (2R,4S,5S1'S)-5-(t-butoxycarbonyl) amino-4-hydroxy-N-[1'-isopropyl-1'-(4-carbomethoxyimidazol-2-yl)]methyl-6-phenyl-2-phenylmethyl-hexanamide a) (1S)-1-carbobenzyloxyamino-1-isopropyl-1-(4-trimethoxymethylimidazol-2-yl)methane.

Sodium methoxide (8 mL, 25% in methanol, 37.5 mmol) was added to a solution of the compound of Example 27(a) (640 mg, 1.88 mmol) in anhydrous methanol (10 mL). The resulting mixture was heated at 55° C. overnight, cooled, and concentrated under reduced pressure. The residue was partitioned between ethyl acetate and H₂O, and the organic extract was dried over Na₂CO₃. The solvent was removed in vacuo, and the residue was purified by flash chromatography (silica, 2% methanol/dichloromethane) to afford the title compound (545 mg, 77%). NMR(CDCl₃) δ 7.40–7.20 (5H, m), 6.98 (1H, br s), 5.90 (1H, br s), 5.08 (2H, s), 4.50 (1H, br s), 3.15 (9H, s), 2.00 (1H, m (br)), 1.00–0.80 (6H, m); MS m/e 378 2 [M+H]⁺, 346, 332, 271, 195.

b) (1S)-1-carbobenzyloxyamino-1-isopropyl-1-(4-carbomethoxyimidazol-2-yl)methane A solution of the compound of Example 26(a) (540 mg) in 1:1 methanol/aqueous HCl (10 mL) was stirred at room temperature for 2 h, and concentrated under reduced pressure. The residue was partitioned between aqueous Na₂CO₃ and dichloromethane, and the organic extract was dried over Na₂CO₃ and concentrated in vacuo to afford the title compound (470 mg, 75%). NMR(CDCl₃) δ 7.55 (1H, br s), 7.35 (5H, s), 5.90–5.65 (1H, m), 5.10 (2H, t, J=4 Hz), 4.60–4.42 (1H, m), 3.88 (3H, s), 2.40 (1H, br s), 1.00–0.80 (6H, m); MS m/e 332.2 [M+H]⁺.

c) (1S)-1-amino-1-isopropyl-1-(4-carbomethoxyimidazol-2-yl)methane

Following the procedure of Example 1(b), except using the compound of Example 26(b), the title compound was prepared. NMR(CDCl₃) δ 7.62 (1H, s), 3.97 (1H, d, j=4 Hz), 3.82 (3H, s), 2.27–2.05 (1H, m), 0.95–0.75 (6H, m).

d) (2R,4S,5S,1'S)-5-(t-butoxycarbonyl)amino-4-t-butyldimethylsiloxy-N-[1'-isopropyl-1'-(4-carbomethoxyimidazol-2-yl)]methyl-6-phenyl-2-phenylmethyl-hexanamide Following the procedure of Example 1(c), except using the compound of Example 26(c), the title compound was prepared. NMR(CDCl₃) δ 7.45–6.90 (12H, m), 6.48 (1H, d, J=4 Hz), 4.72 (1H, d, J=6 Hz), 4.35 (1H, s br), 4.02–3.87 (1H, m), 3.85 (3H, s), 3.75–3.60 (1H, m), 2.90–2.40 (5H, m), 1.90–1.60 (2H, m), 1.42 (9H, s), 0.90 (9H, s), 0.72 (6H, d, J=4 Hz), 0.10 (6H, d, j=3 Hz).

e) (2R, 4S, 5S, 1'S)-5-(t-butoxycarbonyl)amino-4-hydroxy-N-[1'-isopropyl-1'-(4-carbomethoxyimidazol-2-yl)]methyl-6-phenyl-2-phenylmethyl-hexanamide Following the procedure of Example 9(d), except using the compound of Example 26(d), the title compound was prepared. NMR(CDCl₃) δ 7.40–6.80 (12H, m), 4.90 (1H, d, J=5 Hz), 4.50 (1H, br s), 3.90 (3H, s), 3.80–3.60 (2H, m), 2.95–2.68 (5H, m), 2.45–2.30 (1H, m), 1.80–1.60 (2H, m), 1.40 (9H, s), 0.72 (6H, d, j=4 Hz); MS m/e 593.2 [M+H]⁺, 537.2, 519.2, 493.2, 475.2.

EXAMPLE 27

Preparation of (2R,4S,5S,1'S)-5-(t-butoxycarbonyl) amino-4-hydroxy-N-[1'-isopropyl-1'-(4-methylcarbonylimidazol-2-yl)]methyl-6-phenyl-2-phenylmethyl-hexanamide a) (1S)-1-carbobenzyloxyamino-1-isopropyl-1-(4-hydroxymethylimidazol-2-yl)methane.

The compound of Example 26(b) (0.314 g, 1.0 eq) was stirred in anhydrous toluene at −78° C. under an argon atmosphere. Diisobutylaluminum hydride (3.8 mL, 1.0M in hexanes, 4.0 eq) was added and the solution stirred at −78° C. for 1 h. The reaction was quenched with methanol (0.2 mL, 1.0 eq). The solution was then diluted with Rochelles salt solution (sat.) and stirred for 1 h. The solution was extracted with dichloromethane twice and the combined organic extracts were washed successively with saturated aqueous Rochelles salt and brine. The organic layer was dried over magnesium sulfate, filtered, and evaporated to give the title compound as a white solid. (0.27 g, 94%). NMR(CDCl₃) δ 7.25 (5H, s), 6.69 (1H, s), 6.14 (1H, d), 5.01 (2H, dd), 4.52 (2H, s), 4.37 (1H, t), 2.19 (1H, m), 0.92 (3H, d), 0.73 (3H, d); MS m/e 304.0 [M+H]⁺.

b) (1S)-1-carbobenzyloxyamino-1-isopropyl-1-(4-formylimidazol-2-yl)methane.

The compound of Example 27(a) (0.11 g, 1.0 eq) was stirred in anhydrous dichloromethane at room temperature under an inert argon atmosphere. Manganese dioxide (0.126 g. 4.0 eq) was added and the mixture was stirred at room temperature overnight. After 16 h and additional 2.0 eq of manganese dioxide was added. The reaction was complete by TLC after 2 h. The mixture was filtered through a pad of Celite® and the filter cake was washed with dichloromethane. The organic solvent was removed in vacuo to give the title compound as a white solid (0.075 g , 69%). NMR(CDCl$_3$) δ 9.57 (1H, s), 7.54 (1H, s), 7.12 (5H, s), 6.43 (1H, d), 4.96 (2H , dd), 4.43 (1H, t), 2.08 (1H , m), 0.91 (3H, d), 0.62 (3H, t); MS m/e 302.0 [M+H]$^+$.

c) (1S,1'RS)-1-carbobenzyloxyamino-1-isopropyl-1-(4-(1'-hydroxyethyl)imidazol-2-yl)methane.

The compound of Example 27(b) (0.1 g, 1.0 eq) was stirred in a 3:1 ether/THF mixture at 0° C. under an argon atmosphere. Methyl magnesium bromide (0.47 mL, 3.0M in THF, 4.0 eq) was added and allowed to stir at 0° C. for 1.5 h. The solution was diluted with 5% aqueous HCl and made basic with solid sodium carbonate. The solution was extracted with ethyl acetate three times and the combined organic extracts were dried over sodium carbonate, filtered, and evaporated to a white solid (0.1 g, 95%). NMR(CDCl$_3$) δ 7.19 (5H, s), 6.59 (1H, s), 6.42 (1H, d), 4.92 (2H, dd), 4.73 (1H, m), 2.09 (1H, m), 1.37 (3H, d), 0.82 (3H, d), 0.66 (3H, d).

d) (1S,1'RS)-1-amino-1-isopropyl-1-(4-(1'-hydroxyethyl)imidazol-2-yl)methane.

The compound of Example 27(c) (0.1 g, 1.0 eq) was stirred in anhydrous methanol with 10% Pd on activated carbon (0.020 g). Hydrogen gas was bubbled through the solution via balloon for 1 h and the reaction was maintained under a hydrogen atmosphere for 3 h. The mixture was filtered through a pad of Celite® and the filter cake washed with methanol. The methanol was evaporated to give the title compound as a white solid (0.05 g, 87%). NMR(CDCl$_3$) δ 6.63 (1H, s), 4.72 (1H, dd), 3.61 (1H, d), 1.92 (1H, m), 1.49 (3H, d), 0.84 (3H, d), 0.67 (3H, d).

e) (2R,4S,5S,1'S,1"RS)-5-(t-butoxycarbonyl)amino-4-t-butyldimethylsiloxy-N-[1'-isopropyl-1'-(4-(1"-hydroxyethyl)imidazol-2-yl)]methyl-6-phenyl-2-phenylmethyl-hexanamide To a solution of (2R,4S,5S)-5-(t-butoxycarbonyl)amino-4-t-butyldimethylsiloxy-6-phenyl-2-phenylmethylhexanoic acid (0.131 g, 1.0 eq) in anhydrous dimethylformamide, the compound of Example 27(d) (50 mg, 1.1 eq), BOP reagent (0.11 g, 1.0 eq), and triethylamine (0.04 mL, 1.0 eq) were added. The solution was stirred at room temperature for 16 h. The solution was diluted with water and extracted three times with dichloromethane. The combined organic extracts were washed with water, then brine. The solution was dried over magnesium sulfate, filtered, and evaporated to give a white foam. The foam was chromatographed (silica, 4% methanol/dichloromethane) to afford the title compound as a white foam (0.11 g, 65%). NMR(CDCl$_3$) δ 7.31–6.54 (12H, m), 4.72 (1H, d), 4.48 (2H, d), 3.82 (1H, q), 3.61 (1H, m), 2.81–2.3 (6H, m), 1.65 (3H, m), 1.48 (3H, d), 1.22 (9H, s), 0.89 (9H, s), 0.70 (3H, d), 0.61 (3H, d), 0.06 (6H, s); MS m/e 693.4 [M+H]$^+$.

f) (2R,4S,5S,1'S)-5-(t-butoxycarbonyl)amino-4-t-butyldimethylsiloxy-N-[1'-isopropyl-1'-(4-methylcarbonylimidazol-2-yl)]methyl-6-phenyl-2-phenylmethyl-hexanamide The compound of Example 27(e) (45 mg, 1.0 eq) was stirred in dry dichloromethane under an inert argon atmosphere. Manganese dioxide (23 mg, 4.0 eq) was added and the mixture was stirred at room temperature for 16 h. An additional 2.0 eq of manganese dioxide was added and the reaction was complete by TLC after 2.5 h. The mixture was filtered through a pad of Celite® and the filter cake was washed with dichloromethane. The organic solvent was evaporated to give the title compound as a white solid (0.038 g, 85%). NMR(CDCl$_3$) δ 7.49–6.76 (11H, m), 6.30 (1H, br d), 4.71 (2H, m), 3.86 (1H, q), 3.61 (1H, dd), 2.77–2.41 (5H, m), 2.31 (3H, s), 1.58 (2H, m), 1.20 (9H, s), 0.83 (9H, s), 0.69 (6H, dd), 0.04 (6H, d); MS m/e 691.4 [M+H]$^+$.

g) (2R,4S,5S,1'S)-5-(t-butoxycarbonyl)amino-4-hydroxy-N-[1'-isopropyl-1'-(4-methylcarbonylimidazol-2-yl)]methyl-6-phenyl-2-phenylmethyl-hexanamide The compound of Example 27(f) (38 mg, 1.0 eq) was stirred in anhydrous THF under an argon atmosphere at room temperature. Tetrabutyl ammonium fluoride (0.33 mL, 1.0M in THF, 6.0 eq) was added and the solution stirred for 16 h. The solution was diluted with water and extracted three times with dichloromethane. The combined organic extracts were washed with water and evaporated to a white solid. The solid was covered with diethyl ether, decanted twice, and dried to give the title compound as a white solid (25 mg, 79%). NMR(CDCl$_3$) δ 7.14 (5H, m), 6.86 (5H, m), 5.14 (1H, d), 4.42 (1H, d), 3.58 (1H, q), 3.45 (1H, d), 2.80–2.50 (5H, m), 1.91 (1H, m), 1.63 (2H, m), 1.26 (9H, s) (rotamer observed), 0.70 (3H, d), 0.57 (3H, d); MS m/e 577.2 [M+H]$^+$.

EXAMPLE 28

Preparation of (2R,4S,5S,1'S)-5-(t-butoxycarbonyl)amino-4-hydroxy-N-[1'-isopropyl-1'-(4-isopropylcarbonylimidazol-2-yl)]methyl-6-phenyl-2-phenylmethyl-hexanamide a) (1S,1'RS)-1-carbobenzyloxyamino-1-isopropyl-1-(4-(1'-hydroxy-2'-methyl)propylimidazol-2-yl)methane.

Following the procedure of Example 27(c), except using isopropyl magnesium bromide (1.024 mL, 2.0M solution, 4.0 eq) in place of methyl magnesium bromide, to yield a crude product. The crude product was chromatographed (silica, 4% methanol/dichloromethane) to yield the title compound as a white solid (0.155 g , 88%). NMR(CDCl$_3$) δ 7.19 (5H, m), 6.58 (1H, s), 4.91 (2H, m), 4.38 (1H, q), 4.20 (1H, dd), 2.11 (1H, m), 1.83 (1H, m), 0.72 (12H, m); MS m/e 346.2 [M+H]$^+$; 328.2, 279.0, 254.0, 205.0, 177.0, 149.0, 118.0.

b) (1S,1'RS)-1-amino-1-isopropyl-1-(4-(1'-hydroxy-2'-methyl)propylimidazol-2-yl)methane Following the procedure of Example 27(d), using the compound of Example 31(a), the title compound was prepared as a white foam (96 mg, 100%). NMR(CDCl$_3$) δ 6.65 (1H, s), 4.21 (1H, d), 3.90 (1H, s), 2.22 (1H, m), 1.94 (1H, m), 0.93 (6H, m), 0.64 (6H, m); MS m/e 302.0 [M+H]$^+$.

c) (2R,4S,5S,1'S,1"RS)-5-(t-butoxycarbonyl)amino-4-t-butyldimethylsiloxy-N-[1'-isopropyl-1'-(4-(1"-hydroxy-2"-methyl)propylimidazol-2-yl)]methyl-6-phenyl-2-phenylmethyl-hexanamide Following the procedure of Example 27(e), except using the compound of Example 31(b) (96 mg, 1.1 eq), substituting dimethyl formamide as the solvent instead of dichloromethane, and purifying the product by chromatography, the title compound was prepared (168 g, 57%). NMR(CDCl$_3$) δ 7.22–6.81 (11H, m), 6.62 (1H, d), 4.71 (1H, dd), 4.53 (1H, t), 4:19 (1H, d), 3.82 (1H, q), 3.58 (1H, dd), 2.71–2.30 (5H, m), 2.03 (1H, m), 1.70 (1H, m), 1.57 (1H, m), 1.14 (9H, s), 0.91 (3H, d) 0.88 (9H, s), 0.78 (3H, d), 0.67 (3H, d), 0.59 (3H, d), 0.03 (6H, d); MS m/e 721.4 [M+H]$^+$.

d) (2R,4S,5S,1'S)-5-(t-butoxycarbonyl)amino-4-t-butyldimethylsiloxy-N-[1'-isopropyl-1'-(4-isopropylcarbonylimidazol-2-yl)]methyl-6-phenyl-2-phenylmethyl-hexanamide Following the procedure of Example 27(f), except using the compound of 31(c) (168 mg, 1.0 eq) and chromatographing the crude product (silica, 3% methanol/dichloromethane) the title compound was prepared as a white solid (132 mg, 79%). NMR(CDCl₃) δ 7.20–6.76 (11H, m), 5.05 (1H, br m), 3.88 (1H, q), 3.61, m), 3.19 (1H, m), 2.80–2.46 (5H, m), 2.22 (1H, m), 2.07 (1H, m ), 1.63 (1H, m), 1.15 (16H, m), 0.89 (9H, s), 0.74 (6H, m), 0.08 (6H, d); MS m/e 719.4 [M+H]⁺.

e) (2R,4S,5S,1'S)-5-(t-butoxycarbonyl)amino-4-hydroxy-N-[1'-isopropyl-1'-(4-isopropylcarbonylimidazol-2-yl)]methyl-6-phenyl-2-phenylmethyl-hexanamide Following the procedure of Example 27(g), except using the compound of Example 31(d) (132 mg), the title compound was prepared as a white foam (90 mg, 81%). NMR (CDCl₃) δ 7.48 (1H, s), 7.11 (5H, m), 6.82 (5H, m), 5.29 (1H, d), 4.46 (1H, m), 3.54 (1H, q), 3.48 (1H, m), 3.14 (1H, m), 2.74–2.44 (5H, m), 1.90 (1H, m), 1.61 (2H, m), 1.28 (9H, s) (rotamers observed), 1.13 (6H, m), 0.69 (3H, d), 0.48 (3H, d); MS m/e 605.2 [M+H]⁺.

EXAMPLE 29

Preparation of (2R,4S,5S,1'S)-5-(t-butoxycarbonyl) amino-4-hydroxy-N-[1'-isopropyl-1'-(4-phenylcarbonyl-imidazol-2-yl)]methyl-6-phenyl-2-phenylmethyl-hexanamide a) (1S,1'RS)-1-carbobenzyloxyamino-1-isopropyl-1-(4-(1'-hydroxy)benzylimidazol-2-yl)methane Following the procedure of Example 27(c), except substituting phenylmagnesium bromide (0.45 mL, 3.0M solution, 4.0 eq) for methyl magnesium bromide, and chromatographing the crude product (silica, 3% methanol/dichloromethane) the title compound was prepared as a white solid (175 mg, 96%). NMR(CDCl₃) δ 7.26 (1H, d), 7.11 (10H, m), 6.39 (1H, dd), 6.08 (1H, d), 5.63 (1H, d), 4.82 (2H, m), 4.29 (1H, m), 2.01 (1H, m), 0.76 (3H, m), 0.59 (3H, d).

b) (1S,1'RS)-1-amino-1-isopropyl-1-(4-(1'-hydroxy)benzylimidazol-2-yl)methane

Following the procedure of Example 27(d), except using the compound of Example 29(a) (98 mg) the title compound was prepared as a tacky white foam (65 mg, 98%).

c) (2R,4S,5S,1'S,1''RS)-5-(t-butoxycarbonyl)amino-4-t-butyldimethylsiloxy-N-[1'-isopropyl-1'-(4-(1''-hydroxy)benzylimidazol-2-yl)]methyl-6-phenyl-2-phenylmethyl-hexanamide Following the procedure of Example 27(e), except using the compound of Example 29(b) (0.065 g, 1.1 eq), and chromatographing the crude product (2% methanol/dichloromethane) the title compound was prepared as a white solid (109 mg, 55%). NMR(CDCl₃) δ 7.48–6.79 (16H, m), 4.77 (1H, m), 3.88 (1H, m), 3.61 (1H, m), 2.65 (4H, m), 2.39 (1H, m), 2.15 (1H, m), 1.94 (1H, m), 1.75 (1H, m), 1.56 (1H, m), 1.21 (9H, s) (rotamers observed), 0.86 (9H, s), 0.68 (6H, dd), 0.07 (6H, s); MS m/e 755.4 [M+H]⁺.

d) (2R,4S,5S,1'S)-5-(t-butoxycarbonyl)amino-4-t-butyldimethylsiloxy-N-[1'-isopropyl-1'-(4-phenylcarbonylimidazol-2-yl)]methyl-6-phenyl-2-phenylmethyl-hexanamide Following the procedure Example 27 (f), except using the compound of Example 29(c) (109 mg, 1.0 eq), the title compound was prepared as a white solid (80 mg, 74%). NMR(CDCl₃) δ 7.49–6.84 (17H, m), 3.88 (1H, q), 3.63 (1H, t), 2.87–2.49 (6H, m), 2.11 (2H, m), 1.64 (1H, m), 1.11 (9H, s), 0.82 (9H, s), 0.71 (6H, dd), 0.06 (6H, d); MS m/e 753.4 [M+H]⁺.

e) (2R,4S,5S,1'S)-5-(t-butoxycarbonyl)amino-4-hydroxy-N-[1'-isopropyl-1'-(4-phenylcarbonylimidazol-2-yl)]methyl-6-phenyl-2-phenylmethyl-hexanamide Following the procedure of Example 27 (g), except using the compound of Example 29(d) (80 mg, 1.0 eq), the title compound was prepared as a white solid (45 mg, 74%). NMR(CDCl₃) δ 7.84–6.77 (16H, m), 4.48 (1H, d), 3.59 (1H, m), 3.42 (1H, m), 2.80–2.54 (5H, m), 1.99 (1H, m), 1.63 (2H, m), 1.26 (9H, s) (rotamers observed), 0.73 (3H, d), 0.59 (3H, d); MS m/e 639.2 [M+H]⁺.

EXAMPLE 30

Preparation of (2R,4S,5S,1'S)-5-(t-butoxycarbonyl) amino-4-hydroxy-N-[1'-isopropyl-1'-(4-formylimidazol-2-yl)]methyl-6-phenyl-2-phenylmethyl-hexanamide a) (1S,1'RS)-1-amino-1-isopropyl-1-(4-(hydroxy)methyl-imidazol-2-yl)methane.

Following the procedure of Example 27 (d), except using the compound of Example 27(a) (90 mg), the titled compound was prepared (50 mg, 100%). NMR(CDCl₃) δ 6.85 (1H, s), 4.62 (2H, s), 3.85 (1H, d, J=4 Hz), 2.20–2.05 (1H, m), 0.88 (6H, d, J=5 Hz).

b) (2R,4S,5S,1'S)-5-(t-butoxycarbonyl)amino-4-t-butyldimethylsiloxy-N-[1'-isopropyl-1'-(4-(hydroxy)methyl-imidazol-2-yl)]methyl-6-phenyl-2-phenylmethyl-hexanamide Following the procedure of Example 27 (e), except using the compound of Example 30 (a) (50 mg), and chromatographing the crude product (silica, 2% methanol/dichloromethane) the title compound was prepared (130 mg, 65%). NMR(CDCl₃) δ 7.30–6.95 (11H, m), 4.82 (1H, d), 4.50–4.60 (1H, m), 4.40 (1H, d), 3.90–4.00 (1H, m), 3.60–3.68 (1H, m), 2.45–2.80 (5H, m), 2.20–2.30 (1H, m), 1.75–1.85 (1H, m), 1.60–1.70 (1H, m), 1.30 (9H, s), 0.95 (9H, s), 0.75 (3H, d), 0.62 (3H, d), 0.05 (6H, d).

c) (2R,4S,5S,1'S)-5-(t-butoxycarbonyl)amino-4-t-butyldimethylsiloxy-N-[1'-isopropyl-1'-(4-formylimidazol-2-yl)]methyl-6-phenyl-2-phenylmethyl-hexanamide Following the procedure of Example 27 (f), except using the compound of Example 30 (b) (50 mg), the title compound was prepared (20 mg, 40%). NMR(CDCl₃) δ 9.80 (0.5H, s), 9.64 (0.5H, s), 7.50–6.90 (11H, m), 6.52–6.42 (1H, m), 4.88–4.70 (2H, m), 4.42–4.32 (1H, m), 4.02–3.93 (1H, m), 3.78–3.71 (1H, m), 2.90–2.40 (5H, m), 2.30–2.19 (1H, m), 1.87–1.62 (2H, m), 1.45 (9H, s), 0.95 (9H, s), 0.87–0.72 (6H, m), 0.05 (6H, m) (rotamers).

d) (2R,4S,5S,1'S)-5-(t-butoxycarbonyl)amino-4-hydroxy-N-[1'-isopropyl-1'-(4-formylimidazol-2-yl)]methyl-6-phenyl-2-phenylmethyl-hexanamide Following the procedure of Example 27 (g), except using the compound of Example 30(c) (20 mg), the title compound was prepared (12 mg, 71%). NMR(CD₃OD) δ 9.60 (1H, s), 7.65 (1H, s), 7.20–6.90 (10H, m), 4.52 (1H, d), 3.60 (1H, m), 3.45 (1H, d), 2.80–2.45 (5H, m), 2.00–1.88 (1H, m), 1.75–1.65 (1H, m), 1.62–1.45 (1H, m), 1.27 (9H, s), 0.82 (3H, d), 0.62 (3H, d); MS m/e 563.4, 242.2, 204.8.

EXAMPLE 31

Preparation of (2R,4S,5S,1'S)-5-(t-butoxycarbonyl) amino-4-hydroxy-N-[1'-isopropyl-1'-(4-(hydroxymethyl)-imidazol-2-yl)]methyl-6-phenyl-2-phenylmethyl-hexanamide Following the procedure of Example 27 (g), except using the compound of Example 30 (b) (40 mg), the title compound was prepared (20 mg). NMR(CD₃OD) δ 7.27–6.92 (10H, s), 6.72 (1H, s), 4.52 (1H, d), 3.64–3.60(1H, m), 3.48(1H, d), 2.82–2.50 (5H, m), 2.03–1.92 (1H, m), 1.78–1.67 (1H, m), 1.63–1.49 (1H, m), 1.28 (9H, s), 0.80 (3H, d), 0.65 (3H, d); MS m/e 565.4.

EXAMPLE 32

Preparation of (2R,4S,5S,1'S)-5-(t-butoxycarbonyl)amino-4-oxycarbonyl)amino-4-hydroxy-N-(1'-isopropyl-1'-imidazol-2-yl)methyl-6-phenyl-2-phenylmethyl-hexanamide Following the procedures of Example 14(a)–14 (c), except using 4-hydroxytetrahydrothiopyran in place of 2-benzyloxyethanol, the title compound was prepared. Analytical data for the intermediates of this synthesis were:

a) (tetrahydrothiopyran-4-yl)-(4-nitro)phenylcarbonate. NMR(CDCl$_3$) δ 8.26 (1H, s), 8.22 (1H, s), 7.38 (1H, s), 7.33 (1H, s), 4.79 (1H, m), 2.90–2.75 (2H, m), 2.70–2.52 (2H, m), 2.31–2.16 (2H, m), 2.10–1.90 (2H, m).

b) (2R,4S,5S,1'S)-5-((tetrahydrothiopyran-4-yl)oxycarbonyl)-amino-4-hydroxy-N-(1'-isopropyl-1'-imidazol-2-yl)methyl-6-phenyl-2-phenylmethyl-hexanamide. NMR(CD$_3$OD) δ 7.12–6.65 (10H, m), 6.64 (2H, s), 5.60 (1H, d), 4.36 (2H, m), 3.58 (1H, q), 3.49 (1H, d), 2.68–2.48 (6H, m), 2.44–2.30 (3H, m), 1.93–1.74 (3H, m), 1.70–1.40 (4H, m), 0.61 (3H, d), 0.50 (3H, d).

EXAMPLE 33

Preparation of (2R,4S,5S,1'S)-5-((tetrahydro-4H-pyran-4-yl)oxycarbonyl)amino-4-hydroxy-N-(1'-isopropyl-1'-imidazol-2-yl)methyl-6-phenyl-2-phenylmethyl-hexanamide Following the procedures of Example 14(a)–14(c), except using 4-hydroxytetrahydro-4H-pyran in place of 2-benzyloxyethanol, the title compound was prepared. Analytical data for the intermediates of this synthesis were:

a) (tetrahydro-4H-pyran-4-yl)-(4-nitro)phenylcarbonate. NMR(CDCl$_3$) δ 8.32 (1H, s), 8.28 (1H, s), 7.41 (1H, s), 7.38 (1H, s), 5.00 (1H, m), 4.05–2.90 (2H, m), 3.68–3.49 (2H, m), 2.17–2.00 (2H, m), 1.95–1.75 (2H, m).

b) (2R,4S,5S,1'S)-5-((tetrahydro-4H-pyran-4-yl)oxycarbonyl)-amino-4-hydroxy-N-(1'-isopropyl-1'-imidazol-2-yl)methyl-6-phenyl-2-phenylmethyl-hexanamide. NMR(CD$_3$OD) δ 7.16–6.89 (10H, m), 6.79 (2H, s), 4.54 (2H, m), 3.82–3.70 (2H, m), 3.69–3.62 (1H, m), 3.50–3.46 (1H, m), 3.45–3.35 (2H, m), 2.79–2.65 (4H, m), 2.64–2.45 (3H, m), 2.00 (1H, m), 1.82–1.62 (3H, m), 1.55–1.45 (2H, m), 1.37 (1H, m), 0.79 (3H, d), 0.63 (3H, d).

EXAMPLE 34

Preparation of (2R,4S,5S,1'S)-5-(4-picolinyloxy)amino-4-hydroxy-N-(1'-isopropyl-1'-imidazol-2-yl)methyl-6-phenyl-2-phenylmethyl-hexanamide The compound of Example 1(d) was dissolved in neat TFA. After 10 min the solution was concentrated to provide the amine salt. (2R,4S,5S,1'S)-5-amino-4-hydroxy-N-(1'-isopropyl-1'-imidazol-2-yl)methyl-6-phenyl-2-phenylmethyl-hexanamide trifluoroacetate. This amine salt (25 mg, 1 eq) was dissolved in DMF, and 4-picolinium-(p-nitro)phenyl carbonate p-nitrophenylate (23 mg, 1 eq) and triethylamine (0.04 mL, 5 eq) were added. The mixture was stirred under Ar for 17 h. Water was added and the mixture was extracted with dichloromethane. The organic extracts were concentrated and the residue was triturated with ether to yield the title compound (20 mg, 61%). NMR(CD$_3$OD) δ 8.52 (2H, d), 7.10 (14H, m), 6.87 (2H, s), 5.07 (2H, dd), 4.61 (1H, d), 3.80 (1H, m), 3.59 (1H, m), 2.77 (5H, m), 2.05 (1H, m), 1.83 (1H, m), 1.60 (1H, m), 0.84 (3H, d), 0.59 (3H, d). MS m/e570.5 [M+H]$^+$.

EXAMPLE 35

Preparation of (2R,4S,5S,1'S)-5-(t-butoxycarbonyl)amino-4-hydroxy-N-(1'-isopropyl-1'-imidazol-2-yl)methyl-6-phenyl-2-(4,4,4-trifluorobut-1-yl)hexanamide a) (3R,5S,1'S)-(1'-t-butoxycarbonylamino-2'-phenyl)ethyl-3-(4,4,4-trifluorobut-1-yl)-tetrahydrofuran-2-one To a solution of lithium diisopropyl amide (1.8 mL of a 1.5M solution, 2.2 eq) in tetrahydrofuran (10 mL) was added (5S,1'S)-(1'-t-butoxycarbonylamino-2'-phenyl)ethyl-tetrahydrofuran-2-one (0.50 g; 1.0 eq) in anhydrous THF (2 mL) at −78° C. After stirring for 15 min at −78° C., hexamethylphosphoramide (0.57 mL, 2.0 eq) was added to the solution. The solution was stirred for several min and 1,1,1-trifluoro-4-iodobutane (0.78 g, 2.0 eq) was added. After 2 h at −78° C., the reaction mixture was quenched with a 10% aqueous HCl and extracted with dichloromethane. The organic extracts were combined and evaporated to a clear oil. The oil was chromatographed (silica, 2% methanol/dichloromethane) to give the title compound as a white foam (0.248 g, 37%). NMR: (CDCl$_3$) δ 7.18 (5H , m), 4.57 (1H; d), 4.41 (1H, dd), 3.95 (1H, q), 2.82 (2H, d), 2.55 (2H, m), 2.49–1.49 (7H, m), 1.32 (9H, s); MS m/e 438.0 (M+Na)$^+$.

b) (2R,4S,5S)-5-(t-butoxycarbonyl)amino-4-t-butyldimethyl-siloxy-6-phenyl-2-(4,4,4-trifluorobut-1-yl)hexanoic acid Following the procedure of Example 12(b), except using the compound of Example 35(a) (245 mg), the title compound was prepared (215 mg, 67%). NMR(CDCl$_3$) δ 7.18 (5H, m), 4.70 (1H, d), 3.88 (1H, q), 3.69 (2H, m), 2.73 (1H, m), 2.38 (1H, m), 1.91 (2H, m), 1.45 (6H, m), 1.31 (9H, s) (rotamers observed), 0.90 (9H, s), 0.08 (6H, d); MS m/e548.2 [M+H]$^+$.

c) (2R,4S,5S,1'S)-5-(t-butoxycarbonyl)amino-4-t-butyldimethylsiloxy-N-(1'-isopropyl-1'-imidazol-2-yl)methyl-6-phenyl-2-(4,4,4-trifluorobut-1-yl)hexanamide Following the procedure of Example 1 (c), except using the compound of Example 35(b) (100 mg) and (1S)-1-imidazol-2-yl-2-methylpropylamine, the title compound was prepared (83 mg, 68%). NMR(CDCl$_3$) δ 7.22 (5H, m), 7.03 (1H, d), 6.89 (2H, s), 4.72 (1H, d), 4.51 (1H, t), 3.91 (1H, q), 3.65 (1H, m), 2.78 (2H, d), 2.33 (2H, m), 1.82 (4H, m), 1.48 (4H, m), 1.36 (9H, two singlets; rotamers present), 0.99 (9H, s), 0.91 (3H, d), 0.79 (3H, d), 0.07 (6H, d); MS m/e669.4 [M+H]$^+$.

d) (2R,4S,5S,1'S)-5-(t-butoxycarbonyl)amino-4-hydroxy-N-(1'-isopropyl-1'-imidazol-2-yl)methyl-6-phenyl-2-(4,4,4-trifluorobut-1-yl)hexanamide Following the procedure of Example 9(d), except using the compound of Example 35(c) (83 mg), the title compound was prepared (40 mg, 58%). NMR(CD$_3$OD) δ 7.19 (5H, m), 6.92 (2H, s), 4.61 (1H, d), 3.64 (1H, q), 3.48 (1H, m), 2.79 (2H, m), 2.49 (1H, m), 2.13 (4H, m), 1.60 (5H, m), 1.36 (9H, s), 0.90 (3H, d), 0.71 (3H, d); MS m/e555.2 [M+H]$^+$.

EXAMPLE 36

Preparation of (2R,4S,5S,1'S)-2-phenylmethyl-4-hydroxy-5-(t-butoxycarbonyl)amino-6-phenyl-N-(1'-isobutyl-1'-(imidazo-2-yl)]methyl-hexanamide hydrochloride a) 2-(1'-carbobenzyloxyamino-1'-isobutyl)methyl-imidazole Following the procedure of Example 1(a), except substituting Cbz-isoleucinal (1.83 g) for Cbz-valinal, the title compound was prepared (0.658 g, 31%). NMR(CDCl$_3$) δ 6.96 (2H, s), 5.31 (1H, d), 4.48 (1H, dd), 2.15 (1H, m), 1.44

(9H, s), 1.17 (2H, m), 0.92 (3H, t), 0.82 (3H, d); MS (DCI/NH₃) m/e 254.2 [M+H]⁺.

b) (2R,4S,5S,1'S)-2-phenylmethyl-4-hydroxy-5-(t-butoxycarbonyl)amino-6-phenyl-N-(1'-isobutyl-1'-(imidazo-2-yl))methyl-hexanamide hydrochloride Following the procedure of Example 1(b)–1(d), except substituting the compound of Example 36(a) for (1'S)-1'-carbobenzyloxyamino-1'-isopropyl-1'-(imidazo-2-yl) methane, the title compound was prepared. NMR(DMSO-d₆) δ 7.90 (1H, d), 7.29–7.02 (10H, m), 6.89 (2H, s), 6.50 (1H,d), 4.81 (1H,m), 4.55 (1H, dd), 3.56 (1H,m), 2.69 (5H,m), 1.80 (1H,m), 1.59 (2H, m), 1.30 (9H,s), 1.17 (2H, m), 0.78 (3H, t), 0.63 (3H, d); MS (DCI/NH₃) m/e 549.7 [M+H]⁺.

EXAMPLE 37

Preparation of (2R,4S,5S,1'S)-5-(t-butoxycarbonyl) amino-4-hydroxy-N-[1'-isopropyl-1'-(4-(1RS)-1-hydroxyethyl)-imidazol-2-yl)]methyl-6-phenyl-2-phenylmethyl-hexanamide The t-butyldimethylsiloxy-protected alcohol from Example 30(e) (20 mg, 1.0 eq) was stirred in anhydrous THF under an argon atmosphere at room temperature. Tetrabutyl ammonium fluoride (0.33 mL of a 1.0M solution in THF, 6.0 eq) was added and the solution stirred for 16 h. The solution was diluted with water and extracted with dichloromeehane. The combined organic extracts were washed with water and evaporated to a white solid. The solid was covered with diethyl ether and decanted twice to give the title compound as a white solid. (0.012 g, 72%). NMR(CDCl₃) δ 7.22–6.84 (10H, m), 6.61 (1H, s), 5.42 (1H, d), 4.69 (1H, m), 4.41 (1H, d), 3.58 (1H, m), 3.45 (1H, m), 2.78–2.40 (5H, m), 1.91 (1H, m), 1.59 (2H, m), 1.41 (3H, d), 1.26 (9H, s) (rotamers observed), 0.71 (3H, d), 0.59 (3H, d); MS m/e 579.2 [M+H]⁺.

EXAMPLE 38

Preparation of (2R,4S,5S,1'S)-5-(1,1-dimethyl-2-hydroxyethoxycarbonyl)amino-4-hydroxy-N-(1'-isopropyl-1'-imidazol-2-yl)methyl-6-phenyl-2-phenylmethyl-hexanamide a) 2-t-butyldimethylsiloxy-1,1-dimethylethyl-(4-nitrophenyl)carbonate A mixture containing bis(4-nitrophenyl)carbonate (0.996 g, 3.28 mmol), 2-t-butyldimethylsiloxy-1,1-dimethylethanol (0.67 g, 1 eq) and 4-dimethylaminopyridine (0.4 g, 1 eq) in dichloromethane (50 mL) was stirred at room temperature for 5 d. The mixture was diluted With dichloromethane and washed successively with H₂O and saturated aqueous NaCl, and dried over Na₂CO₃. The solvent was removed in vacuo, and the residue was purified by flash chromatography (silica, 20% ethyl acetate/hexanes) to afford the title compound (35%). NMR(CDCl₃) δ 8.25 (2H, m), 7.35 (2H, m), 3.76 (2H, s), 1.53 (6H, s), 0.94 (9H, s), 0.09 (6H, s).

b) (2R,4S,5S,1'S)-5-(2-t-butyldimethylsiloxy-1,1-dimethylethoxycarbonyl)amino-4-t-butyldimethylsiloxy-N-(1'-isopropyl-1'-imidazol-2-yl)methyl-6-phenyl-2-phenylmethyl-hexanamide A solution of 2-t-butyldimethylsiloxy-1,1-dimethylethyl-4-nitrophenyl carbonate (137 mg, 0.372 mmol), (2R,4S,5S,1'S)-5-amino-4-t-butyldimethylsiloxy-N-(1'-isopropyl-1'-imidazol-2-yl)methyl-6-phenyl-2-phenylmethyl-hexanamide (102 mg, 0.186 mmol) and DMAP (45 mg, 0.372 mmol) in methylene choride was stirred at 20° C. under Ar for 24 h. The solution was washed with aqueous Na₂CO₃, dried over solid Na₂CO₃ and concentrated. Flash chromatography (4% methanol/dichloromethane) provided the intermediate (2R,4S,5S,1'S)-5-(2-t-butyldimethylsiloxy-1,1-dimethylethoxycarbonyl)amino-4-t-butyldimethylsiloxy-N-(1'-isopropyl-1'-(1-(2-t-butyldimethylsiloxy-1,1-dimethylethoxycarbonyl)imidazol-2-yl)methyl-6-phenyl-2-phenylmethyl-hexanamide, which was dissolved in ether, washed with 10% NaOH, dried over Na₂CO₃, and concentrated to provide the title compound (110 mg, 78% overall). NMR(CDCl₃) δ 7.37–6.70 (13H, m), 6.39 (1H, d), 4.84 (1H, d), 4.55 (1H, t), 3.96 (1H, q), 3.69 (2H, s), 3.60–3.42 (2H, m), 2.94 (1H, s(br)), 2.85–2.44 (4H, m), 2.39 (1H, q), 1.90–1.60 (2H, m), 1.31 (6H, d), 1.02–0.85 (18H, m), 0.83 (6H, t), 0.98 (12H, m).

c) (2R,4S,5S,1'S)-5-(1,1-dimethyl-2-hydroxyethoxy-carbonyl)amino-4-hydroxy-N-(1'-isopropyl-1'-imidazol-2-yl)methyl-6-phenyl-2-phenylmethyl-hexanamide A mixture containing the compound of Example 38(b) (110 mg) and tetra-n-butylammonium fluoride (6 eq of 1M solution in THF) under an argon atmosphere was allowed to stir at room temperature overnight. The solution was diluted with dichloromethane and washed with water, and the organic layer was concentrated. The residue was purified by flash chromatography (4% methanol/dichloromethane) to afford the title compound (0.05 g, 66%). NMR(CDCl₃, CD₃OD) δ 7.30–6.78 (12H, m), 4.42 (1H, d), 3.75–3.38 (4H, m), 2.97–2.50 (5H, m), 2.08 (1H, m), 1.70–1.56 (2H, m), 1.30 (6H, s), 0.90–0.55 (6H, dd).

EXAMPLE 39

Preparation of (2R,4S,5S,1'S)-5-(1,1-dimethyl-2-hydroxy-ethoxycarbonyl)amino-4-hydroxy-N-(1'-isopropyl-1'-imidazol-2-yl)methyl-6-phenyl-2-phenylmethyl-hexanamide hydrochloride A 1M solution of HCl in ether (63.5 mL) was added to a solution of the compound of Example 38(c) (35 mg, 0.064 mmol) in methanol (5 mL). The solvent was removed by rotary evaporation at 20° C., and the solid residue was triturated with ether and dried to afford the title compound as the hydrochloride salt (35 mg, 95%). NMR(CD₃OD) δ 7.37–6.85 (12H, m), 4.56 (1H, d), 3.59 (1H, m), 3.48–3.33 (3H, m), 2.85–2.48 (6H, m), 2.04 (1H, septet), 1.72–1.49 (2H, m), 1.22 (6H, d), 0.88(3H, d), 0.61 (3H, dd).

EXAMPLE 40

Preparation of (2R,4S,5S,1'S)-5-(2-hydroxyethoxycarbonyl)-amino-4-hydroxy-N-(1'-isopropyl-1'-imidazol-2-yl)methyl -6-phenyl-2-phenylmethyl hexanamide a) benzyloxyethyl-(4-nitro)phenylcarbonate To a solution of 2-benzyloxyethanol (2.5 g, 16.4 mmol) and bis(4-nitrophenyl)carbonate (5.0 g, 1 eq) in dichloromethane (200 mL), N-methylmorpholine (1.81 mL, 1 eq) was added. The resulting mixture was allowed to stir at room temperature for 3 d. The reaction mixture was washed successively with H₂O and saturated aqueous NaCl and dried over Na₂SO₄. The solvent was removed in vacuo, and the residue was purified by flash chromatography (silica, 20% ethyl acetate/hexanes) to afford the title compound (4.38 g, 84%). NMR(CDCl₃) δ 8.26 (2H, m), 7.34 (7H, m), 4.62 (2H, s), 4.49 (2H, t), 3.70 (2H, t).

b) (2R,4S,5S,1'S)-5-(2-benzyloxyethoxycarbonyl)amino-4-t-butyldimethylsiloxy-N-[1'-isopropyl-1'-(N'-(2-benzyloxyethoxy)carbonyl)imidazol-2-yl]methyl-6-phenyl-2-phenylmethyl-hexanamide To a solution of (2R,4S,5S,1'S)-5-amino-4-t-butyldimethylsiloxy-N-(1'-isopropyl-1'-imidazol-2-yl) methyl-6-phenyl-2-phenylmethyl-hexanamide (134.5 mg, 0.24 mmol) in dichloromethane (40 mL) under an argon atmosphere, benzyloxyethyl 4-nitrophenyl carbonate (160 mg, 2 eq) and 4-dimethylaminopyridine (60 mg, 2 eq) were added. The resulting mixture was allowed to stir at room temperature overnight, and was diluted with dichloromethane. The organic extract was washed successively with aqueous $Na_2CO_3$, $H_2O$, aqueous $Na_2CO_3$ and $H_2O$, and dried over $Na_2CO_3$. The solvent was removed in vacuo, and the residue was purified by flash chromatography (silica, 4% methanol/dichloromethane) to afford the title compound (180 mg, 82%). NMR(CDCl$_3$) δ 7.45–6.80 (22H, m), 6.62 (1H, d), 5.60 (1H, t), 5.06 (1H, d), 4.60 (2H, s), 4.52 (2H, s), 4.50 (2H, m), 4.31 (1H, m), 4.07 (2H, m), 3.80 (2H, t), 3.68 (1H, q), 3.57 (1H, q), 2.85 (1H, m), 2.77–2.41 (4H, m), 2.09 (1H, m), 1.90 (1H, m), 1.73 (1H, m), 0.95 (9H, s), 0.81 (6H, dd), 0.11 (6H, d).

c) (2R,4S,5S,1'S)-5-(2-hydroxyethoxycarbonyl)amino-4-t-butyl-dimethylsiloxy-N-[1'-isopropyl-1'-(N'-2-benzyloxyethoxy-carbonyl)imidazol-2-yl]methyl-6-phenyl-2-phenylmethyl-hexanamide The compound of Example 40(b) (68 mg, 0.44 mmol) was stirred as a solution in methanol (50 mL) with Pd(0) (10 mg) under 1 atm hydrogen for 12 h. The mixture was filtered, the solvent was removed in vacuo, and the residue was purified by flash chromatography (silica, 4% methanol/dichloromethane) to afford the title compound (44 mg, 74%). NMR(CDCl$_3$) δ 7.36–6.72 (12H, m), 5.03 (1H, d), 4.80 (1H, dd), 4.50–4.32 (2H, m), 4.07–3.52 (5H, m), 2.96–2.32 (6H, m), 1.98–1.85 (2H, m), 0.95 (9H, s), 0.90–0.75 (6H, dd), 0.05 (6H, d).

d) (2R,4S,5S,1'S)-5-(2-hydroxyethoxycarbonyl)amino-4-hydroxy-N-(1'-isopropyl-1'-imidazol-2-yl)methyl-6-phenyl-2-phenylmethyl-hexanamide To a solution of the compound of of Example 40(c) in methanol, excess aqueous HCl (approx. 5 equiv.) was added. The resulting solution was stirred at room temperature overnight, and concentrated under reduced pressure. The residue was diluted with $H_2O$, and made basic with aqueous $Na_2CO_3$. The mixture was extracted with dichloromethane, and the combined organic extracts were dried over $Na_2CO_3$. The solvent was removed in vacuo, and the residue was purified by flash chromatography to afford the title compound. NMR(CD$_3$OD) δ 7.28–6.85 (12H, m), 4.55 (1H, a), 3.95 (1H, m), 3.73–3.40 (4H, m), 2.86–2.47 (5H, m), 1.99 (1H, m), 1.71 (1H, m), 1.22 (1H, m), 0.84 (3H, d), 0.62 (3H, d).

EXAMPLE 41

Preparation of (2R,4S,5S,1'S)-5-(1RS)-1-methyl-2-hydroxyethoxycarbonyl)amino-4-hydroxy-N-(1'-isopropyl-1'-imidazol-2-yl)methyl-6-phenyl-2-phenylmethyl-hexanamide a) 2-t-butyldimethylsiloxy-1-methylethyl-(4-nitrophenyl)-carbonate A mixture containing bis(4-nitrophenyl)carbonate (3.20 g, 10.5 mmol), 2-t-butyldimethylsiloxy-1-methylethanol (2.0 g, 10.5 mmol) and 4-dimethylaminopyridine (1.30 g, 10.5 mmol) in dichloromethane (200 mL) was stirred at room temperature for 5 d. The mixture was then diluted with dichloromethane and washed successively with $H_2O$ and saturated aqueous NaCl and dried over $Na_2CO_3$. The solvent was removed in vacuo, and the residue was purified by flash chromatography (silica, 10% ethyl acetate/hexane) to afford the title compound (88%). NMR(CDCl$_3$) δ 8.28 (2H, m), 7.39 (2H, m), 4.98 (1H, m), 3.75 (2H, d), 1.38 (3H, s), 0.92 (9H, s), 0.11 (6H, s).

b) (2R,4S,5S,1'S)-5-(2-t-butyldimethylsiloxy-1-methylethoxycarbonyl)amino-4-t-butyldimethylsiloxy-N-(1'-isopropyl-1'-imidazol-2-yl)methyl-6-phenyl-2-phenylmethyl-hexanamide Following the procedure of Example 38 (b), except substituting the compound of Example 4 (a) for 2-t-butyldimethylsiloxy-1,1-dimethylethyl-4-nitrophenyl carbonate, the title compound was prepared. NMR(CDCl$_3$) δ 7.40–7.00 (10H, m), 6.90 (½H, s), 6.72 (½H, s), 6.45 (1H, dd), 4.92 (1H, dd), 4.84–4.61 (2H, m), 4.10 (1H, m), 3.76 (1H, m), 3.58 (1H, m), 2.92–2.73 (3H, m), 2.70–2.45 (3H, m), 1.78 (2H, m), 1.22–1.08 (3H, m), 1.04–0.81 (24H, m), 0.17–0.09 (12H, m).

c) (2R,4S,5S,1'S)-5-((1RS)-1-methyl-2-hydroxyethoxycarbonyl)-amino-4-hydroxy-N-(1'-isopropyl-1'-imidazol-2-yl)methyl-6-phenyl-2-phenylmethyl-hexanamide Following the procedure of Example 38 (c), except using the compound of Example 4 (b), the title compound is prepared. NMR(CD$_3$OD) δ 7.15–6.68 (12H, m), 5.72–5.60 (1H, dd), 4.58 (1H, m), 4.38 (1H, dd), 4.06 (1H, m), 3.62 (1H, m), 3.41 (1H, m), 2.79–2.55 (5H, m), 2.49 (1H, dd), 1.92 (1H, m), 1.67 (1H, m), 1.08–0.98 (3H, dd), 0.69 (3H, dd), 0.58 (3H, dd).

EXAMPLE 42

Preparation of (2R,4S,5S,1'S)-5-(2-hydroxy-1-cyclopentyloxycarbonyl)amino-4-hydroxy-N-(1'-isopropyl-1'-imidazol-2-yl)methyl-6-phenyl-2-phenylmethylhexanamide a) (trans)-2-(t-butyldimethysiloxy)-cyclopentanol To a mixture of t-butyldimethylsilyl chloride (5.08 g, 33.7 mmol) and imidazole (2.30 g, 33.7 mmol) in DMF (10 mL), a solution of trans-1,2-cyclopentanediol in DMF (4 mL) was added. The reaction mixture was stirred overnight at 25° C. The reaction mixture was diluted with ice water and extracted with ether. The ether extract was washed with water and brine, dried over magnesium sulfate, filtered and the solvent removed in vacuo. The residue was purified by flash chromatography (silica, 9:1 hexane:ethyl acetate) to the title compound as an oil (3.44 g, 49%).

b) ((trans)-2-(t-butyldimethysiloxy)-cyclopentyl)-(4-nitrophenyl)carbonate

To a solution of the compound of Example 42(a) (1.08 g, 5 mmol) and DMAP (0.611 g, 5 mmol) in dichloromethane (12 mL), bis(4-nitrophenyl)carbonate (1.52 g, 5 mmol) was added. The solution was stirred overnight at 25° C. The reaction mixture was diluted with dichloromethane (15 mL), and washed with water and brine. The organic extract was dried over magnesium sulfate, filtered, and the solvent was removed at reduced pressure. The residue was triturated with hexane:ethyl acetate (1:1) and filtered. The filtrate was evaporated to an oil and purified by flash chromatography (silica, 9:1 hexane:ethyl acetate) to yield the title compound as an oil (1.75 g, 92%).

c) 5-((trans)-2-t-butyldimethylsiloxy-cyclopentyloxy-carbonyl)amino-4-t-butyldimethysiloxy-N-[1'-isopropyl-1'-(1-(2-t-butyldimethysiloxy-cyclopentyloxycarbonyl))imidazol-2-yl]methyl-6-phenyl-2-phenylmethyl-hexanamide A solution of 5-amino-4-t-butyldimethylsiloxy-N-[1'-isopropyl-1'-imidazol-2-yl]methyl-6-phenyl-2-phenylmethyl-hexanamide (171 mg, 0.311 mmol), DMAP (76.1 mg, 0.623 mmol) and the compound of Example 42(b) (238 mg, 0.623 mmol) in dichloromethane (9 mL) was stirred overnight at 25° C. The reaction mixture was diluted with dichloromethane, washed with water and saturated sodium bicarbonate solution, and dried with magnesium sulfate. The organic extract was filtered and the solvent was removed in vacuo. The residue was purified by flash chromatography (silica, 4:1 hexane:ethyl acetate) to yield the title compound as an oil (150 mg, 47%).

d) 5-((trans)-2-hydroxy-cyclopentyloxycarbonyl)amino-4-hydroxy-N-[1'-isopropyl-1'-imidazol-2-yl]methyl-6-phenyl-2-phenylmethyl-hexanamide To a solution of the compound of Example 42(c) (150 mg, 0.145 mmol) in methanol (5 mL), 3N HCl (3 mL) was added. The solution was stirred overnight at 25° C. The methanol was evaporated in vacuo, and the residue was diluted with water and extracted with ether. The aqueous solution was neutralized with 5% sodium carbonate (~pH 7) and a solid precipitated. The solid was filtered, washed with water and dried in vacuo to yield the title compound (51.5 mg, 63%). NMR(CD$_3$OD, 400 MHz) δ 7.0–7.3 (m, 10H), 6.87 (s, 2H), 4.63 (m, 2H), 3.88 (m, 1H), 3.55 (d, 1H), 2.5–2.9 m, 5H), 1.4–2.1 (br, 9H), 0.88 (d, 3H), 0.71 (d, 3H); TLC R$_f$ 0.27 (silica, 8% methanol/chloroform).

EXAMPLE 43

Preparation of (2R,4S,5S,1'S)-5-(4-hydroxybutanoyl)amino-4-hydroxy-N-(1'-isopropyl-1'-imidazol-2-yl)methyl-6-phenyl-2-phenylmethylhexanamide a) t-butyldimethylsilyl 4-(t-butyldimethylsiloxy)-butanoate To a suspension of t-butyldimethylsilyl chloride (29.9 g, 198 mmol) in dry DMF (20 mL), 4-hydroxybutyric acid, sodium salt (5.0 g, 397 mmol) and imidazole (27.0 g, 0.397 mol) were added. The reaction mixture was stirred overnight at 25° C. The solvent was removed under reduced pressure and the residue was diluted with 10% aqueous citric acid (200 mL). The residue was extracted with ether. The ether solution was dried with magnesium sulfate, filtered and evaporated to yield the title compound as an oil.

b) 4-t-butyldimethylsiloxy-butanoic acid

A solution of the compound of Example 43(a) (5.0 g) was dissolved in acetic acid:tetrahydrofuran:water (2:2:1, 50 mL) solution and stirred for 2.5 h. The solution was diluted with water and extracted with ether. The ether solution was dried with magnesium sulfate, filtered and evaporated to an oil. The oil was purified by flash chromatography (silica, hexane-ethyl acetate, 9:1) to yield the title compound as an oil (180 mg).

c) (2R,4S,5S,1'S)-5-(4-t-butyldimethylsiloxy-butanoyl)amino-4-hydroxy-N-(1'-isopropyl-1'-imidazol-2-yl)methyl-6-phenyl-2-phenylmethylhexanamide A solution of (2R,4S,5S,1'S)-5-amino-4-t-butyldimethylsiloxy-N-(1'-isopropyl-1'-imidazol-2-yl)methyl-6-phenyl-2-phenylmethyl-hexanamide (175 mg, 0.319 mmol), 4-t-butyldimethylsiloxy-butanoic acid (84 mg, 0.41 mmol), BOP reagent (148, 0.335 mmol), triethylamine (46 μL, 0;335 mmol) and dichloromethane (4 mL) were stirred at 20° C. under Ar for 24 h. The reaction mixture was diluted with dichloromethane, washed with aqueous Na$_2$CO$_3$, water and brine, and dried over solid magnesium sulfate. The organic phase was filtered, and concentrated in vacuo. The residue was purified by chromatchromatography (silica, 2% methanol/chloroform) to provide the title compound.

d) (2R,4S,5S,1'S)-5-(4-hydroxybutanoyl)amino-4-hydroxy-N-(1'-isopropyl-1'-imidazol-2-yl)methyl-6-phenyl-2-phenylmethylhexanamide A solution of the compound of Example 43(c) (177 mg, 0.236 mmol) and tetra-n-butylammonium fluoride (2.84 mL, 2.84 mmol, 1M solution in THF) was stirred under an argon atmosphere at room temperature overnight. The solution was diluted with ethyl acetate, washed with saturated sodium bicarbonate solution, and water, and the organic layer was concentrated. The residue was precipitated from the ethyl acetate solution to afford the title compound. NMR δ (CD$_3$OD, 400 MHz) 7.0–7.3 (m, 10H), 6.86 (s, 2H), 4.62 (d, 1H), 4.05 (m, 1H), 3.43 (t, 2H), 2.55–2.90 (m, 4H), 2.60 (m, 1H), 2.17 (m, 2H), 2.05 (m, 1H), 1.76 (m, 1H), 1.67 (m, 2H), 1.55 (m, 1H), 0.88 (d, 3H), 0.72 (d, 3H); TLC R$_f$ 0.40 (silica, 10% methanol/chloroform).

EXAMPLE 44

Preparation of (2R,4S,5S,1'S)-2-phenylmethyl-4-hydroxy-5-(benzyloxycarbonyl)valylamino-6-phenyl-N-(1'-isobutyl-1'-imidazo-2-yl)methyl-hexanamide (a) (2R,4S,5S,1'S)-2-phenylmethyl-4-butyldimethylsiloxy-5-(benzyloxycarbonyl)valylamino-6-phenyl-N-(1'-isobutyl-1'-(imidazo-2-yl))methyl-hexanamide.

A solution of carbobenzyloxy-(L)-valine (50.4 mg, 0.20 mmol), the product of Example 13(a) (110 mg, 0.20 mmol), BOP reagent (88.7 mg, 0.20 mmol) and triethylamine (28 μl, 0.20 mmol) in methylene chloride (4 mL) was stirred at 25° C. for 4 d. The reaction mixture was diluted with methylene chloride, washed with saturated sodium bicarbonate and the organic layer was concentrated. The product was purified by flash chromatography (silica gel, 4% CH$_2$Cl$_2$/ MeOH) to give the title compound (104 mg, 67%).

(b) (2R,4S,5S,1'S)-2-phenylmethyl-4-hydroxy-5-(benzyloxycarbonyl-valyl)amino-6-phenyl-N-(1'-isobutyl-1'-imidazo-2-yl)methyl-hexanamide.

To a solution of the compound of Example 44(a) (104 mg, 0.133 mmol) in MeOH (8 mL), 3N HCl (2 mL) was added. The solution was stirred for 16 hrs at 25° C. The methanol was removed at reduced pressure and 10% sodium carbonate was added to pH ~7.5. Ether (10 mL) was added and the solid product was filtered and dried in vacuo to provide the title compound (58 mg, 65%). NMR(CDCl$_3$) δ 0.62 (d, 3H), 0.78 (d, 3H), 0.82 (d, 3H), 0.90 (d, 3H), 1.62 (m, 2H), 1.96 (m, 1H), 2.06 (m, 1H), 2.55 (m, 1H), 2.77 (m, 4H), 3.38 (s, 1H), 3.53 (m, 1H), 3.91 (M,1H), 3.99 (m, 1H), 4.47 (d, 1H), 5.11 (s, 2H), 5.78 (d, 1H), 6.85 (s, 2H), 6.92–7.34 (m, 15H); MS m/e 667 [M+H]$^+$.

EXAMPLE 45

Preparation of (2R,4S,5S,1'S)-2-phenylmethyl-4-hydroxy-5-(N-acetylvalyl)amino-6-phenyl-N-(1'-isobutyl-1'-imidazo-2-yl)methyl-hexanamide (a) (2R,4S,5S,1'S)-2-phenylmethyl-4-t-butyldimethylsil)oxy-5-(N-acetyl-valyl)amino-6-phenyl-N-(1'-isobutyl-1'-imidazo-2-yl)methyl-hexanamide To a solution of N-acetyl-(L)-valine (40.3 mg, 0.253 mmol) in dry THF (8 mL) at −40° C. was added n-methylmorpholine (55.7 μl, 0.506 mmol) followed by isobutyl chloroformate (33.5 μl, 0.253 mmol). The reaction mixture was stirred for 15 min, and the compound of Example 13(b) (139 mg, 0.253 mmol) in THF (3 mL) was added. The reaction mixture was allowed to warm to room temperature and stirred for 2 d. The reaction was diluted with ethyl acetate, and washed with water and brine. The organic solution was dried with sodium sulfate, filtered and the solvent removed under reduced pressure. The residue was purified by flash chromatography (silica, 4% methanol/chloroform) to give the product as an oil (47 mg, 27%).

(b) (2R,4S,5S,1'S)-2-phenylmethyl-4-hydroxy-5-(N-acetylvalyl)amino-6-phenyl-N-(1'-isobutyl-1'-imidazo-2-yl)methyl-hexanamide.

To a solution of the compound of Example 45(a) (47 mg, 0.0681 mmol) in methanol (3 mL), 3N HCl (0.5 mL) was added. The reaction was stirred for 16 h at 25° C. The methanol was removed under reduced pressure and the solution was diluted with water and neutralized with 5% sodium carbonate. The solid product was filtered, washed with water and ether, and dried in vacuo to yield the title compound (29.5 mg, (75%). NMR (CD$_3$OD) δ 0.70 (d, 3H), 0.88 (m, 9H), 1.57 (m, 1H), 1.70 (m, 1H), 1.92 (s, 3H), 2.05 (m, 1H), 2.55 (q, 1H), 2.77 (m, 4H), 3.57 (d, 1H), 4.03 (m, 2H), 4.60 (d, 1H), 6.87 (s, 2H), 6.95–6.20 (m, 10H); MS m/e 575 [M+H]$^+$.

EXAMPLE 46

Preparation of (2R,4S,5S,1'S)-5-[(imidazol-2-yl) methyloxycarbonyl]amino-4-hydroxy-N-(1'-isopropyl-1'-imidazol-2-yl)methyl-6-phenyl-2-phenylmethyl-hexanamide a) (1-(benzyloxymethyl)imidazol-2-yl)methyl-(4-nitrophenyl)carbonate A mixture of bis (4-nitrophenyl)carbonate, (1-benzyloxymethyl)imidazol-2-yl)methanol and 4-dimethylaminopyridine was reacted according to the procedure of Example 14 (a) to afford the title compound (58%). NMR(CDCl$_3$, 400 MHz) δ 8.18 (d, 2 H, J=8.38 Hz), 7.44–7.23 (m, 7H), 7.11 (s, 1H), 7.13 (s, 1H), 5.48 (s, 2H), 5.44 (s, 2H), 4.49 (s, 2H).

b) (2R,4S,5S,1'S)-5-((1-benzyloxymethyl)imidazol-2-yl) methyloxycarbonyl)amino-4-t-butyldimethylsiloxy-N-(1'-isopropyl-1'-imidazol-2-yl)methyl-6-phenyl-2-phenylmethyl-hexanamide.

A mixture of the compound of Example 46(a), (2R,4S,5S,1'S)-5-amino-4-hydroxy-N-(1'-isopropyl-1'-imidazol-2-yl)methyl-6-phenyl-2-phenylmethyl-hexanamide, and 4-dimethylaminopyridine was reacted according to the procedure of Example 14(b) to afford the title compound (32%). NMR(CDCl$_3$) δ 7.50–6.60 (m, 19H), 5.25 (m, 2H), 5.11 (d, 2H, J=11.03 Hz), 4.68 (m, 1H), 4.39 (m, 2H), 3.97 (m, 1H), 3.67 (m, 1H), 2.88 (m, 1H), 2.72–2.28 (m, 6H), 1.85 (m, 1H), 1.60 (m, 1H), 0.92–0.81 (m, 15H), 0.80 (s, 3H), 0.06 (s, 3H); MS (ES) m/e 793 [M+H]$^+$.

c) (2R,4S,5S,1'S)-5-(imidazoyl-2-yl-methyloxycarbonyl) amino-4-t-butyldimethylsiloxy-N-(1'-isopropyl-1'-imidazol-2-yl)methyl-6-phenyl-2-phenylmethyl-hexanamide The compound of Example 46(b) (58 mg, 0.073 mmol), methanol (3 mL), and 10% Pd on carbon (50 mg) were combined and stirred under 1 atm of H$_2$ for 24 h. Additional catalyst (50 mg) was added and stirring under H$_2$ was continued for 8 h. The reaction was filtered through Celite®, concentrated and flash chromatographed (silica, step gradient, 0–8% MeOH/CH$_2$Cl$_2$) to yield the title compound (28 mg, 57%). NMR(CDCl$_3$) δ 7.29–6.83 (m, 14H); 5.05 (d, 1H, J=11.2 Hz), 4.91 (d, 1H, J=11.2 Hz), 4.71 (m, 1H), 3.92 (m, 1H), 3.61 (m, 1H), 3.02 (m, 1H), 2.81–2.54 (m, 4H), 2.36 (m, 1H), 1.93 (m, 1H), 1.59 (m, 1H), 0.91 (d, 3H, J=7.1 Hz), 0.89 (s, 9), 0.69 (d, 3H, J=7.1 Hz), 0.84–0.05 (m, 6H); MS(ES) m/e 673 [M+H]$^+$.

d) (2R,4S,5S,1'S)-5-(imidazol-2-yl-methyloxycarbonyl) amino-4-hydroxy-N-(1'-isopropyl-1'-imidazol-2-yl)methyl-6-phenyl-2-phenylmethyl-hexanamide The compound of Example 46(c) (24 mg, 0.035 mmoL), 95% aqueous EtOH (0.50 mL), and concentrated aqueous HCl (0.050 mL) were stirred at 23° C. for 24 h. The solution was diluted with H$_2$O (5 mL) washed with EtOAc and then the aqueous phase was made basic by addition of solid K$_2$CO$_3$. Extraction with EtOAc, concentration of the organic extract and trituration with CH$_2$Cl$_2$ afforded the title compound (14 mg, 72%). NMR (CDCl$_3$) δ 7.33–6.85 (m, 14H), 5.11 (d, 1H, J=10.8 Hz), 4.96 (d, 1H, J=10.8 Hz), 4.47 (m, 1H), 3.72 (m, 1H), 3.38 (m, 1H), 2.81 (m, 4H), 2.59 (m, 1H), 2.07 (m, 1H), 1.72 (m, 1H), 1.62 (m, 1H), 0.78 (d, 3H, J=6.63 Hz), 0.67 (d, 3H, J=6.63 Hz); (m, 6H); MS (ES) m/e 559 [M+H]$^+$.

EXAMPLE 47

Preparation of (2R,4S,5S,1'S,1"RS)-5-((1"-(imidazol-2-yl)-2"-methyl)propyloxycarbonyl) amino-4-hydroxy-N-(1'-isopropyt-1'-imidazol-2-yl) methyl-6-phenyl-2-phenylmethyl-hexanamide a) (1RS)-1-((1-benzyloxymethylimidazol-2-yl)-2-methyl) propyl-(4-nitrophenyl)carbonate A mixture of bis(4-nitrophenyl)carbonate, (1RS)-1-((1-benzyloxymethylimidazol-2-yl)-2-methyl)propanol and 4-dimethylaminopyridine was reacted according to the procedure of Example 14(a) to afford the title compound (61%). NMR (CDCl$_3$) δ 8.18 (d, 2H, J=8.31 Hz), 7.38–7.21 (m, 7H), 7.13 (s, 1H), 6.94 (s, 1H), 5.74 (d, 1H, J=11.1 Hz), 5.47 (d, 1H, J=10.2 Hz), 5.28 (d, 1H, J=10.2 Hz), 4.53 (d, 1H, J=11.3 Hz), 4.41 (d, 1H, J=11.3 Hz), 2.64 (m, 1H), 1.18 (d, 3H, J=6.02 Hz), 0.87 (d, 3H, J=6.02 Hz); MS(ES) m/e 426 [M+H]$^+$.

b) (2R,4S,5S,1'S,1"RS)-5-((1"-(1-benzyloxymethylimidazol-2-yl)-2"-methyl-propyl) oxycarbonyl)amino-4-t-butyldimethylsiloxy-N-(1'-isopropyl-1'-(1-(1"-(1-benzyloxymethylimidazol-2-yl)-2"-methylpropyl) oxycarbonyl)imidazol-2-yl)methyl-6-phenyl-2-phenylmethyl-hexanamide A mixture of the compound of Example 47(a) (145 mg, 0.33 mmol), the compound of Example 13(a) (75.9 mg, 0.14 mmol), 4-dimethylaminopyridine (41 mg, 0.33 mmol) and DMF (0.5 mL) was stirred under argon for 18 h. The DMF was evaporated in vacuo and the residue was combined with 10% aq K$_2$CO$_3$ (10 mL) and extracted with EtOAc. The combined extracts were washed with saturated aq NaHCO$_3$, dried (K$_2$CO$_3$), filtered and concentrated in vacuo. The residue was flash chromatographed (silica, step gradient, 0–4% MeOH/CH$_2$Cl$_2$) to afford the title compound (96.1 mg, 57%). NMR (CDCl$_3$) δ 7.38–6.78 (m, 26H), 5.67 (m, 1H), 5.61–5.00 (m, 6H), 4.58–4.27 (m, 5H), 3.97–3.61 (m, 3H), 2.78–2.10 (m, 8H), 1.95–1.51 (m, 2H), 1.10–0.55 (m, 27H), 0.50–0.05 (m, 6H).

c) (2R,4S,5S,1'S,1"RS)-5-[(1"-(1-benzyloxymethyl-imidazol-2-yl)-2"-methyl-propyl)oxycarbonyl]amino-4-hydroxy-N-(1'-isopropyl-1'-imidazol-2-yl)methyl-6-phenyl-2-phenylmethyl-hexanamide A solution of the compound of Example 47(b) (81 mg, 0.07 mmol), CH$_3$OH (0.75 mL), and 3N aqueous HCl (0.25 mL) was stirred at 23° C. for 20 h. The reaction mixture was diluted with H$_2$O (10 mL) and washed with EtOAc (3×15mL). Solid K$_2$CO$_3$ was added to give a basic solution (pH>12), which was extracted with EtOAc. The extracts were dried (K$_2$CO$_3$), filtered, concentrated and flash chromatographed (silica, step gradient, 0–8% CH$_3$OH/CH$_2$Cl$_2$) to give the title compound (34.9 mg, 65%). $^1$H NMR (CDCl$_3$) δ 7.43–6.79 (m, 9H), 5.87, 5.66 (2d, 1H, J=10.66, 10.85 Hz), 5.28 (m, 2H), 4.68 (m, 1H), 4.42 (m, 2H), 3.71 (m, 1H), 3.58 (m, 1H), 2.90–2.31 (m, 6H), 2.11 (m, 1H), 1.75, 1.51 (2m, 2H), 1.05, 0.97 (2d, 3H, J=6.32,6.45), 0.68 (m, 9H).

d) (2R,4S,5S,1'S,1"RS)-5-((1"-(imidazol-2-yl)-2"-methyl) propyloxycarbonyl)amino-4-hydroxy-N-(1'-isopropyl-1'-imidazol-2-yl)methyl-6-phenyl-2-phenylmethyl-hexanamide.

A mixture of the compound of Example 47 (c) (34 mg, 0.047 mmol), CH$_3$OH (4 mL), and 10% Pd/C (34 mg), was stirred under H$_2$ (1 atm) for 26 h. The suspension was filtered through Celite®, concentrated, and triturated with $CH_2Cl_2$ to yield the title compound (4 mg, 14%). $^1H$ NMR $(CDCl_3/CD_3OD)$ δ 7.7.32–6.71 (m, 14H), 5.38 (m, 1H), 4.55 (m, 1H), 3.72 (m, 1H), 3.55 (m, 1H), 2.78 (m, 4H), 2.55 (m, 1H), 2.15 (m, 2H), 1.60 (m, 2H), 1.03–0.61 (m, 12H).

EXAMPLE 48

Preparation of (2R,4S,5S,1'S)-5-(t-butoxycarbonyl) amino-4-hydroxy-N-[1'-isopropyl-1'-(4-(imidazol-2-yl)imidazol-2-yl)]methyl-6-phenyl-2-phenylmethyl-hexanamide (a) (1'S)-1'-(carbobenzyloxy)amino-1'-isopropyl-1'-(4-(imidazol-2-yl)imidazol-2-yl)methane Cbz-(L)-valinal (0.45 g, 1.4 mmol) was stirred in anhydrous methanol at 0° C. under argon. Glyoxal (40% in water) (0.22 mL, 1.4 mmol) and ammonium hydroxide (29% $NH_3$) (0.88 mL, 14 mmol) were added and the mixture was allowed to stir at 0° C. for 1 h. The cooling bath was removed and the solution stirred at room temperature for 16 h. The methanol was evaporated in vacuo and the residue was diluted with 5% aqueous HCl. After extracting with dichloromethane, the aqueous layer was made basic with solid sodium carbonate and extracted with dichloromethane. The combined organic extracts were dried over sodium carbonate, filtered, and evaporated to a solid which was chromatographed (silica, 4% methanol/dichloromethane) to give the title compound (0.216 g, 43%) as a white solid. NMR $(CDCl_3)$ δ 7.15 (6H, s(br)), 6.88 (2H, s), 6.30 (1H, d), 4.89 (2H, dd), 4.52 (1H, t), 2.05 (1H, m), 0.73 (3H, d), 0.62 (3H, d). MS m/e 340.2 $[M+H]^+$ (b) (2R,4S,5S,1'S)-5-(t-butoxycarbonyl)amino-4-hydroxy-N-[1'-isopropyl-1'-(4-(imidazol-2-yl)imidazol-2-yl)]methyl-6-phenyl-2-phenylmethyl-hexanamide The compound of Example 48(a) (0.13 gm.) was dissolved in anhydrous methanol with 10% Pd on activated carbon (0.02 g). Hydrogen gas was bubbled through the solution via balloon for 1 h and the solution was stirred overnight under a hydrogen atmosphere. The mixture was filtered through a pad of Celite® and evaporated to yield 1'-amino-1'-isopropyl-[4-(imidazol-2-yl)imidazol-2-yl] methane as a white solid (0.13 g, 100%).

This compound was combined with the compound of Example 13(a) (0.334 g, 0.63 mmol), BOP reagent (0.28 g, 0.63 mmol), and triethylamine (0.13 mL, 0.945 mmol) in DMF (1 mL) and allowed to stir under Ar for 3 d. The DMF was evaporated in vacuo and the residue was diluted with dichloromethane. The solution was washed with water and brine. The organic layer was dried over sodium carbonate, filtered, and evaporated to yield (2R,4S,5S,1'S)-5-(t-butoxycarbonyl)amino-4-t-butyldimethysiloxy-N-[1'-isopropyl-1'-(4-(imidazol-2-yl)imidazol-2-yl)methyl-6-phenyl-2-phenylmethyl hexanamide as a white solid.

A portion of the solid (0.100 g, 0.14 mmol) was stirred in THF at room temperature under argon. Tetrabutylammonium fluoride (0.84 mL, 0.84 mmol) was added and the mixture was allowed to stir for 16 h. The solution was diluted with water and extracted twice with dichloromethane. The combined organic extracts were washed with water and evaporated to an oily residue. The residue was dissolved in THF and several drops of diethyl ether were added until a white precipitate formed. The precipitate was collected by filtration and dried in vacuo to yield the title compound as a white solid (76 mg, 90%). NMR $(CD_3OD)$ δ 7.37–6.84 (13H, m), 4.61 (1H, d), 3.69 (2H, m), 3.54 (1H, d), 2.84–2.52 (5H, m), 2.06 (1H, m), 1.83 (2H, m), 1.57 (1H, m), 1.30 (9H, s), 0.87 (3H, d), 0.69 (3H, d); MS m/e 601.2 $[M+H]^+$

EXAMPLE 49

Preparation of (2R,4S,5S,1'S)-5-[di(hydroxymethyl)-methoxycarbonyl]amino-4-hydroxy-N-(1'-isopropyl-1'-imidazol-2-yl)methyl-6-phenyl-2-phenylmethyl-hexanamide a) di(t-butyldimethylsiloxymethyl) methyt-(4-nitrophenyl) carbonate A mixture containing bis(4-nitrophenyl) carbonate(1.89 g, 6.21 mmol), di(t-butyldimethylsiloxymethyl)methanol (2.00 g, 1 eq) and 4-dimethylaminopyridine (757 mg, 1 eq) in dichloromethane (100 mL) was stirred at room temperature for 2 d. The mixture was diluted with dichloromethane and washed with saturated aqueous $Na_2CO_3$, brine, and dried over $Na_2SO_4$. The solvent was removed in vacuo, and the residue was purified by flash chromatography (silica, 10% ethyl acetate/hexanes) to afford the title compound (75%). NMR $(CDCl_3)$ δ 8.29 (2H, m), 7.37 (2H, m), 3.96 (1H, m), 3.85 (2H, d), 3.82 (2H, d), 0.89 (18H, s), 0.09 (12H, s).

b) (2R,4S,5S,1'S)-5-(di(t-butyldimethylsiloxymethyl) methyloxycarbonyl]amino-4-t-butyldimethylsiloxy-N-(1'-isopropyl-1'-imidazol-2-yl)methyl-6-phenyl-2-phenylmethyl-hexanamide A solution of di(t-butyldimethylsiloxymethyl)-methyl 4-nitrophenyl carbonate (475 mg, 0.974 mmol), the compound of Example 13(a) (178 mg, 0.325 mmol) and dimethylaminopyridine (119 mg, 0.974 mmol) in methylene choride was stirred at 20° C. under Ar for 24 h. The solution was washed with aqueous $Na_2CO_3$, dried over solid $Na_2CO_3$ and concentrated in vacuo. Flash chromatography (silica, 4% methanol/dichloromethane) of the residue provided the intermediate (2R,4S,5S,1'S)-5-(di(t-butyldimethylsiloxymethyl)methyloxycarbonyl)amino-4-t-butyldimethylsiloxy-N-(1'-isopropyl-1'-(1-(di(t-butyldimethylsiloxymethyl) methyloxycarbonyl)imidazol-2-yl)methyl-6-phenyl-2-phenylmethyl-hexanamide, which was dissolved in ether, washed with 10% NaOH, dried over $Na_2CO_3$, and concentrated to provide the title compound (197 mg, 71%). NMR $(CDCl_3)$ δ 7.43–7.05 (10H, m), 6.90 (2H, s), 6.65 (1H, bs), 5.09 (1H, d), 4.78 (1H, bd), 4.08 (1H, m), 3.89–3.50 (7H,m) 3.00–2.80 (4H, m), 2.65 (1H, m), 2.55 (2H, m), 1.90 (1H, m), 1.78 (1H, m), 1.10–0.85 (33H, m), 0.20–0.06 (18H, m).

c) (2R,4S,5S,1'S)-5-(di (hydroxymethyl)methoxycarbonyl) amino-4-hydroxy-N-(1'-isopropyl-1'-imidazol-2-yl)methyl-6-phenyl-2-phenylmethyl-hexanamide A mixture containing the compound of Example 49(b) (50 mg) and ethereal HCl (4 eq) was allowed to stir in methanol:water (9:1) at room temperature overnight. The solvent was removed in vacuo, and the residue was diluted with ethyl acetate and washed with saturated aqueous $Na_2CO_3$. The product was, purified by flash chromatography (silica, 4% methanol/dichloromethane) to afford the title compound (29 mg, 94%). NMR $(CD_3OD)$ δ 7.20–6.80 (10H, m), 6.71 (2H, s), 4.50 (1H, d), 3.90 (1H,m), 3.65–3.34 (5H, m), 2.82–2.45 (6H, m), 1.99 (1H, m), 1.74 (1H, m), 1.52 (1H, m), 0.78 (3H, d), 0.60 (3H, d).

EXAMPLE 50

Preparation of (2R,4S,5S,1'S)-5-(1-oxo-thian-4-yl) oxycarbonyl)amino-4-hydroxy-N-(1'-isopropyl-1'-imidazol-2-yl)methyl-6-phenyl-2-phenylmethylhexanamide Reacting the compound of Example 32 (b) (81 mg, 0.133mmol) with m-chloro perbenzoic acid (23 mg, 0.133mmol) in $CH_2Cl_2$ yielded the title compound. NMR (CD$_3$OD) δ 7.20–6.85 (10H, m), 6.78 (2H, s), 4.51 (1H, d), 3.66 (1H, m), 3.42(1H, m), 2.95–2.41 (9H, m), 2.32–2.01 (2H, m), 1.99–1.63 (4H, m), 1.60–1.41 (2H, m), 0.78 (3H, d), 0.60 (3H, d); MS m/e 595.2 [M+H]$^+$.

EXAMPLE 51

Preparation of (2R,4S,5S,1'S)-5-((tetrahydrosulfonylpyran-4-yl)oxycarbonyl)amino-4-hydroxy-N-(1'-isopropyl-1'-imidazol-2-yl)methyl-6-phenyl-2-phenylmethylhexanamide Reacting the compound of Example 50 (31 mg, 49.2 μmol) with m-chloro perbenzoic acid (10 mg, 59.2 μmol) in methylene chloride yielded the title compound. NMR (CD$_3$OD) δ 7.20–6.85 (10H, m), 6.76 (2H, s), 4.48 (1H, d), 3.68 (1H, m), 3.44(1H, m), 2.96–2.42 (9H, m), 2.32–2.04 (2H, m), 1.97–1.62 (4H, m), 1.61–1.43 (2H, m), 0.79(3H, d), 0.60 (3H, d); MS m/e 611.2 [M+H]$^+$.

EXAMPLE 52

Preparation of (2R,4S,5S,1'S)-5-(1,1-dimethyl-2-acetoxyethoxycarbonyl)amino-4-hydroxy-N-(1'-isopropyl-1'-imidazol-2-yl)methyl-6-phenyl-2-phenylmethyl-hexanamide (a) (2R,4S,5S,1'S)-5-(1,1-dimethyl-2-hydroxyethoxycarbonyl)amino-4-(t-butyldimethylsilyl)oxy-N-(1'-isopropyl-1'-imidazol-2-yl)methyl-6-phenyl-2-phenylmethyl-hexanamide The compound of Example 38(b) (223 mg, 0.221 mmol) was dissolved in 10% aqueous methanol and combined with 1M HCl in ether (0.221 mL, 1 eq) at room temperature. After completion of the reaction the solvents were removed in vacuo. The residue was dissolved in dichloromethane and washed with aqueous saturated Na$_2$CO$_3$. The organic layer was concentrated and the residue was purified by flash chromatography (silica, 4% methanol/dichloromethane) to provide the title compound (138 mg, 94%). NMR (CDCl$_3$) δ 7.38–6.81 (12H, m), 4.93+4.65 (1H, d, rotamers), 4.81+4.48 (1H, t, rotamers), 4.15+4.08 (1H, d, rotamers), 3.90 (1H, q), 3.72 (2H, m), 3.50+3.38 (1H, d, rotamers), 2.98–2.48 (5H, m), 2.35 (1H, m), 1.98 (1H, m), 1.79 (1H, m), 1.60 (1H, m), 1.30 (3h, s), 1.29 (3H, s), 1.09–0.85 (15H, m), 0.79 (3H, d), 0.11 (6H, m).

(b) (2R,4S,5S,1'S)-5-(1,1-dimethyl-2-acetoxyethoxycarbonyl)amino-4-hydroxy-N-(1'-isopropyl-1'-imidazol-2-yl)methyl-6-phenyl-2-phenylmethyl-hexanamide The compound of Example 52(a) (103 mg, 0.155 mmol) was stirred with acetic anhydride (30 mg, 0.309 mmol) and DMAP (40 mg, 0.309 mmol) in methylene chloride at room temperature under argon overnight. The solvent was removed in vacuo and the residue was flash chomatagraphed (silica, 4% methanol/dichloromethane).

The resulting 4-t-butyldimethylsiloxy intermediate (105 mg, 0.140 mmol) was stirred in methanol:water (9:1) with 1M HCl in ether (0.14 mL, 1 eq). The solvents were removed in vacuo, the residue was diluted with dichloromethane, and the solution was washed with aqueous Na$_2$CO$_3$. The organic layer was concentrated and the residue was purified by flash chromatography (silica, 5% methanol/dichloromethane) to provide the title compound (82 mg, 91%). NMR (CD$_3$OD) δ 7.29–6.90 (10H, m), 6.81 (2H, s), 4.51 (1H, d), 4.05 (2H, s), 3.59(1H, m), 3.42 (1H, m), 2.80–2.45 (5H, m), 2.00 (1H, m), 1.98 (3H, s), 1.72 (1H, m), 1.50 (1H, m), 1.34 (6H, d), 0.81 (3H, d), 0.60 (3H, d).

EXAMPLE 53

Preparation of (2R,4S,5S,1'S)-5-((1,1-dimethyl-2-(benzyloxy-carbonylglycyloxy)ethoxycarbonyl) amino-4-hydroxy-N-(1'-isopropyl-1'-imidazol-2-yl) methyl-6-phenyl-2-phenylmethyl-hexanamide hydrochloride salt a) (2R,4S,5S,1'S)-5-((1,1-dimethyl-2-carbobenzyloxyglycyloxy)ethoxycarbonyl)amino-4-(t-butyldimethylsilyloxy)-N-(1'-isopropyl-1'-imidazol-2-yl)methyl-6-phenyl-2-phenylmethyl-hexanamide The compound of Example 52(a) (100 mg, 0.151 mmol) was reacted with 2-chloro-1-methyl-pyridium iodide (92 mg, 0.36 mmol), DMAP (75 mg, 0.60 mmol) and Cbz-glycine (63 mg, 0.30 mmol) in methylene chloride (5 mL) under argon at reflux for 3 h. Solvents were removed in vacuo and the product was purified by flash chromatagraphy (silica, 4% methanol/dichloromethane) to provide the title compound (95 mg, 73%). NMR (CDCl$_3$) δ 7.41–6.71 (17H, m), 6.62 (1H, bs), 6.00 (1H,m), 5.20 (1H, m), 5.15 (2H, s), 4.83+4.55 (1H, d, rotamers), 4.65+4.48 (1H, t, rotamers), 4.81+4.38 (1H, q, rotamers), 4.03 (1H, q), 4.02 (2H, d), 3.85+3.68 (2H, d, rotamers), 2.85–2.48 (5H, m), 2.38 (1H, m), 1.90 (1H, m), 1.55 (1H, m), 1.38 (3h, s), 1.29 (3H, s), 0.90 (9H, m), 0.85 (3H, d), 0.70 (3H, d), 0.11 (6H, m).

b) (2R,4S,5S,1'S)-5-((1,1-dimethyl-2-(benzyloxycarbonyl) ethoxycarbonyl)amino-4-hydroxy-N-(1'-isopropyl-1'-imidazol-2-yl)methyl-6-phenyl-2-phenylmethy-hexanamide hydrochloride salt The compound of Example 53(a) (12 mg, 0.014 mmol) was stirred in methanol:water (9:1) with 1M HCl (2 eq) in ether overnight. The solvents were removed in vacuo to give the title compound (8 mg, 73%). NMR(CD$_3$OD) δ 7.35 (2H, s), 7.31–6.85 (15H, m), 5.00 (2H, s), 4.59 (1H, d),4.15 (1H, d, rotamers), 4.65+4.48(1H, t, rotamers), 4.81+4.38 (2H, dd), 3.80 (2H, d), 3.59 (1H, m), 3.40 (1H, d), 2.85–2.48 (5H, m), 2.00 (1H, m), 1.60 (1H, m), 1.55 (1H, m), 1.31 (3h, s), 1.29 (3H, s), 0.91 (3H, d), 0.60 (3H, d).

EXAMPLE 54

Preparation of (2R,4S,5S,1'S)-5-((1,1-dimethyl-2-glycyloxy)ethoxycarbonyl)amino-4-hydroxy-N-(1'-isopropyl-1'-imidazol-2-yl)methyl-6-phenyl-2-phenylmethyl-hexanamide dihydrochloride salt a) (2R,4S,5S,1'S)-5-(1,1-dimethyl-2-glycyloxyethoxycarbonyl)amino-4-(t-butyldimethylsilyl)oxy-N-(1'-isopropyl-1'-imidazol-2-yl)methyl-6-phenyl-2-phenylmethyl-hexanamide The compound of.Example 53(a) (58 mg, 0.0678mmol) was stirred in methanol with 10% Pd/C (50 mg) under 1 atm hydrogen overnight. The reaction mixture was filtered through Celite® and the solvents were removed in vacuo to yield the title compound (48 mg, 98%). NMR(CD$_3$OD) δ 7.32–7.02 (10H, m), 6.99 (2H, s), 4.68 (1H, d),4.40–4.28 (2H, dd), 3.81 (2H, d), 3.80–3.67 (2H, m), 2.90–2.49 (5H, m), 2.15 (1H, m), 1.97 (1H, m), 1.48 (1H, m), 1.40 (3H, s), 1.39 (3H, s), 1.15 (3H, d), 0.95 (9H, s), 0.70 (3H, d), 0.11 (6H, d).

b) (2R,4S,5S,1'S)-5-((1,1-dimethyl-2-glycyloxy)ethoxycarbonyl)amino-4-hydroxy-N-(1'-isopropyl-1'-imidazol-2-yl)methyl-6-phenyl-2-phenylmethyl-hexanamide dihydrochloride salt The compound of Example 54(a) (43.5 mg, 0.060 mmol) was stirred in methanol:water (9:1) with 1M HCl in ether (0.12 mL, 2 eq) for 2 d. The solvents were removed in vacuo and the product was triturated with ether:methanol (20:1) to yield the title compound (40 mg, 98%). NMR(CD$_3$OD) δ

7.35 (2H, s), 7.30–6.92 (10H, m), 4.60 (1H, d), 4.25 (2H, dd), 3.75 (2H, d), 3.59 (1H, m),3.49 (1H, m), 2.90–2.51 (6H, m), 2.10 (1H, m), 1.65 (1H, m), 1.54 (1H, m), 1.30 (6H, s), 0.90 (3H, d), 0.60 (3H, d).

EXAMPLE 55

Preparation of (2R,4S,5S,1'S)-5-((1,1-dimethyl-2-hydroxy)ethoxycarbonyl)amino-4-hydroxy-N-(1'-isopropyl-1'-(4-isopropylcarbonylimidazol-2-yl)) methyl-6-phenyl-2-phenylmethyl-hexanamide dihydrochtoride salt a) (2R,4S,5S,1'S)-5-amino-4-t-butyldimethylsiloxy-N-[1'-isopropyl-1'-(4-isopropylcarbonyl-imidazol-2-yl)]methyl-6-phenyl-2-phenylmethyt-hexanamide Using the procedure of Example 13(a), except substituting the compound of Example 28(d), the title compound was prepared.

b) (2R,4S,5S,1'S)-5-((1,1-dimethyl-2-hydroxy) ethoxycarbonyl)amino-4-hydroxy-N-(1'-isopropyl-1'-( 4-isopropylcarbonylimidazol-2-yl) )methyl-6-phenyl-2-phenylmethyl-hexanamide dihydrochloride salt Following the procedures of Example 38(b)–38(c), except substituting the compound of Example 55(a) for (2R,4S,5S, 1'S)-5-amino-4-t-butyldimethylsiloxy-N-('-isopropyl-1'-imidazol-2-yl)methyl-6-phenyl-2-phenylmethyl-hexanamide, the title compound was prepared. NMR (CDCl₃) δ 7.49 (1H, s), 7.13 (5H, m), 6.84 (5H, m), 5.53 (1H, d), 4.47 (1H, d), 3.79 (1H, m), 3.60 (1H, m), 3.44 (2H, m), 3.16 (1H, m), 2.81–2.50 (5H, m), 1.92 (1H, m), 1.62 (2H, m), 1.18 (14H, m), 0.72 (3H, d), 0.58 (3H, d); MS m/e 621.4 [M+H]⁺.

EXAMPLE 56

Preparation of (2R,4S,5S,1'S)-5-((1S)-1-methyl-2-hydroxyethoxycarbonyl)amino-4-hydroxy-N-(1'-isopropyl-1'-imidazol-2-yl)methyl-6-phenyl-2-phenylmethylhexanamide Using the procedure of Example 41, except substituting 2 (S)-t-butyldimethylsiloxy-1-methylethanol in 41(a) (prepared from 2 (S)-1,2-propanediol), the title compound was prepared. NMR(CD₃OD) δ 7.38–6.90 (10H, m), 6.83 (2H, s), 4.58 (2H, m), 3.61 (1H, m), 3.34 (3H, m), 2.82–2.44 (5H, m), 2.00 (1H, m), 1.66 (1H, m), 1.52 (1H, m), 1.08 (3H, d), 0.85 (3H, d), 0.60 (3H, d).

EXAMPLE 57

Preparation of (2R,4S,5S,1'S)-5-((1R)-1-methyl-2-hydroxyethoxycarbonyl)amino-4-hydroxy-N-(1'-isopropyl-1'-imidazol-2-yl)methyl-6-phenyl-2-phenylmethylhexanamide Using the procedure of Example 41, except substituting 2 (R)-t-butyldimethylsiloxy-1-methylethanol in 41(a), the title compound was prepared. NMR(CD₃OD) δ 7.39–6.88 (10H, m), 6.82 (2H, s), 4.56 (2H, m), 3.60 (1H, m), 3.36 (3H, m), 2.81–2.45 (5H, m), 1.99 (1H, m), 1.65 (1H, m), 1.51 (1H, m), 1.03 (3H, d), 0.84 (3H, d), 0.60 (3H, d).

EXAMPLE 58

Preparation of (2R,4S,5S,1'S)-5-((1-acetyl)amino-4-hydroxy-N-(1'-isopropyl-1'-imidazol-2-yl)methyl-6-phenyl-2-phenylmethylhexanamide The title compound was prepared by the procedure of Example 13(a)–(c), except substituting acetic anhydride in place of isopropyl chloroformate. NMR(CD₃OD) δ 7.21–6.90 (10H, m), 6.81 (2H, s), 4.58 (1H, d), 3.98 (1H, m), 3.51 (1H, m), 2.85–2.49 (5H, m), 1.99 (1H, m), 1.68 (3H, s), 1.61 (3H, m), 1.50 (1H, m), 0.80 (3H, d), 0.60 (3H, d).

EXAMPLE 59

Preparation of (2R,4S,5S,1'S)-5-(t-butoxycarbonyl) amino-4-hydroxy-N-(1'-isopropyl-1'imidazol-2-yl) methyl-6-phenyl-2-(4-benzyloxyphenylmethyl) hexanamide a) (3R,5S,1'S)-(1'-t-butoxycarbonylamino-2'-phenyl)ethyl-3-(4-benzyloxy)phenylmethyl-tetrahydrofuran-2-one Following the procedure of Example 12(a), except using (4-benzyloxy)benzyl bromide, the title compound was prepared (284 mg, 27%). NMR(CDCl₃) δ 7.48–6.72 (14H, m), 4.94 (2H, s), 4.43 (1H, d), 4.12 (1H, dd), 3.83 (1H, q), 2.97–2.62 (5H, m), 2.12 (1H, m), 1.85 (1H, m), 1.27 (9H, s).

b) (2R,4S,5S)-5-(t-butoxycarbonyl)amino-4-t-butyldimethyl-siloxy-6-phenyl-2-(4-benzyloxyphenylmethyl)hexanoic acid Folowing the procedure of Evans et al., *J. Org. Chem.* 50, 4615 (1985), except substituting the compound of Example 59(a) for benzyl bromide, the title compound was prepared. NMR(CDCl₃) δ 7.42–6.76 (14H, m), 4.99 (2H, s), 4.69 (1H, d), 3.91 (1H, q), 3.66 (1H, m), 2.98–2.36 (5H, m), 1.85 (1H, m), 1.52 (1H, m), 1.30 (9H, s), 0.88 (9H, s), 0.04 (6H, m).

c) (2R,4S,5S,1'S)-5-(t-butoxycarbonyl)amino-4-t-butyldimethylsiloxy-N-(1'-isopropyl-1'-imidazol-2-yl) methyl-6-phenyl-2-(4-benzyloxyphenylmethyl) hexanamide.

Following the procedure of Example 12(c), except using (b), the title compound was prepared (284 mg, 92%). NMR(CDCl₃) δ 7.42–6.74 (16H, m), 5.04 (2H, s), 4.99 (1H, d), 4.77 (1H, d), 4.51 (1H, dd), 3.93 (1H, q), 3.69 (1H, m), 2.80–2.39 (5H, m), 1.81 (1H, m), 1.62 (1H, m), 1.33 (9H, s), 0.92 (9H, s), 0.75 (6H, dd), 0.07 (6H, d).

d) (2R,4S,5S,1'S)-5-(t-butoxycarbonyl)amino-4-hydroxy-N-(1'-isopropyl-1'-imidazol-2-yl)methyl-6-phenyl-2-(4-benzyloxyphenylmethyl) hexanamide Following the procedure of 12(d), except using (c), the title compound was prepared (100 mg, 94%). NMR (CD₃OD) δ 7.41–7.09 (10H, m), 6.85 (2H, d), 6.79 (2H, s), 6.58 (2H, d), 5.41 (1H, d), 4.90 (2H, s), 4.47 (1H, d), 3.62 (1H, q), 3.48 (1H, d), 2.79–2.48 (6H, m), 2.02 (1H, m), 1.62 (2H, m), 1.33 (9H, s), 0.74 (3H, d), 0.61 (3H, d).

EXAMPLE 60

Preparation of (2R,4S,5S,1'S)-5-(t-butoxycarbonyl) amino-4-hydroxy-N-(1'-isopropyl-1'imidazol-2-yl) methyl-6-phenyl-2-(4-hydroxyphenylmethyl) hexanamide Following the procedure of Example 4(b), except using the compound of 59(d), the title compound was prepared (56 mg, 86%). NMR(CD₃OD) δ 7.18 (5H, m), 6.84 (2H, s), 6.73 (2H, d), 6.44 (2H, d), 5.32 (1H, d), 4.45 (1H, d), 3.61 (1H, q), 3.42 (1H, m), 2.80–2.42 (5H, m), 2.04 (1H, m), 1.61 (2H, m), 1.31 (9H, s), 0.70 (3H, d), 0.61 (3H, d).

EXAMPLE 61

Preparation of (2R,4S,5S)-5-(t-butoxycarbonyl) amino-4-hydroxy-2-phenylmethyl-6-phenyl-N-[1'-cyclopropyl-1'-imidazol-2-yl]methyl-hexanamide a) α-(t-butoxycarbonyl)-amino-α-cyclopropylacetonitrile To a solution of cyclopropylmethanol (10.2 g, 141 mmol) in methylene chloride (250 mL) sodium acetate (1 g) and 20 g of Celite® were added. Pyridinium chlorochromate (30 g, 140 mmol) was added in small portions over a period of 30 m. After 1 h the reaction mixture was diluted with ether (100mL), filtered through Celite® and washed with ether. The combined organic extracts (1 L) were concentrated in vacuo at 15°–18° C. to yield formyl cyclopropane.

The crude aldehyde was dissolved in water (50 mL), and ammonium chloride (6.51 g), potassium cyanide (7.16 g) and aqueous ammonium hydroxide (100 mL, 28% w/w). The reaction mixture was stirred at room temperature overnight, extracted with ethyl acetate, and the combined organic extracts were dried over MgSO$_4$. Filtration and evaporation of the solvent in vacuo yielded α-amino-α-cyclopropyl acetonitrile as an oil.

To a solution of the crude aminonitrile (2 g) in THF (20 mL) di-tert-butyldicarbonate (1.53 g, 7 mmol) was added. The reaction was stirred overnight. Removal of the solvent in vacuo followed by flash chromatography (silica, 1:8 ethyl acetate:hexane) yielded the title compound (2.8 g). $^1$H NMR(CDCl$_3$, 200 MHz) δ 5.0 (bs, 1H), 4.4 (bs, 1H), 1.4 (s, 9H), 1.2 (m, 1H), 0.7 (m, 2H), 0.5 (m, 2H).

b) α-(t-butoxycarbonyl)-amino-α-cyclopropylacetaldehyde

To a solution of the compound of Example 61(a) (1 g, 5.1 mmol) in THF (20 mL), diisobutylaluminium hydride (10.5 mL, 10.5 mmol, 1M in THF) was added at –78° C., over 5 min. The reaction mixture was allowed to warm to 0° C. over a period of 2 h, and stirred at 0° C. for an additional 1 h. The reaction mixture was quenched with MeOH (2 mL), and saturated potassium sodium tartrate solution (100 mL) was added. Extraction with ether, drying over MgSO4 and removal of solvents in vacuo yielded an oil. Flash chromatography (silica, 1:10 ethyl acetate:hexane) gave the title compound as a colorless solid (225 mg). NMR(CDCl$_3$, 400 MHz) δ 9.45 (bs, 1H), 4.95 (bs, 1H), 3.5 (bs, 1H), 1.3 (s, 9H), 0.7 (m, 1H), 0.3–0.6 (m, 4H).

c) 1-(t-butoxycarbonyl)amino-1-(imidazol-2-yl)-1-cyclopropyl-methane

A mixture of the compound of Example 61(b) (178 mg, 0.89 mmol), glyoxal (150 mL, 1 mmol, 40% aq), ammonium hydroxide (5 mL, 28% aq) and MeOH (5mL) was stirred at room temperature for 10 h. The solvents were removed in vacuo and the residue was titurated with ether to yield a brown solid (53 mg). The solid was passed through Florisil® and eluted with 5% MeOH/methylene chloride. Removal of the solvent in vacuo followed by trituration provided the title compound as a colorless solid (19 mg). MS (Cl/NH$_3$) m/e 238.3 [M+H]$^+$. $^1$H NMR(CD$_3$OD, 200 MHz) δ 6.9 (s, 2H), 4.1 (bd, 1H), 1.4 (s, 9H), 1.3 (m, 1H), 0.6 (m, 2H), 0.4 (m, 2H).

d) 1-amino-1-(imidazol-2-yl)-1-cyclopropyl-methene, trifluoroacetate

The compound of Example 61(c) (15 mg) was dissolved in 1 mL of TFA and stirred at room temperature for 20 min. Solvents removed in vacuo to give the title compound as a semisolid residue. $^1$H NMR(CD$_3$OD, 200 MHz) δ 7.1 (s, 2H), 3.8 (d, 1H, j=7 Hz), 1.5 (m, 1H), 0.5–0.8 (m, 4H).

e) (2R,4S,5S)-5-(t-butoxycarbonyl)amino-4-(t-butyldimethyl)-siloxy-2-phenylmethyl-6-phenyl-N-[1'-cyclopropyl-1'-imidazol-2-yl]methyl-hexanamide The compound of Example 61(d) was dissolved in DMF (2 mL) and NMM (26 mg, 0.25 mmol) was added and the solution was stirred at 0° C. for 30 min. (2R,4S,5S)-2-phenylmethyl-4-(t-butyldimethyl)siloxy-5-(t-butoxycarbonyl)amino-6-phenyl hexanoic acid (38 mg, 0.07 mmol) and BOP reagent (30 mg, 0.07 mmol) were added and the reaction was stirred at room temperature for 24 h. The reaction was diluted with ethyl acetate (100 mL), washed with aqueous sodium bicarbonate and dried over anhydrous potassium carbonate. Removal of solvents in vacuo, followed by flash chromatography (silica, 5% methanol/methylene chloride) yielded the title compound as a mixture of diastereomers (25 mg). f) (2R,4S,5S)-5-(t-butoxycarbonyl)amino-4-hydroxy-2-phenylmethyl-6-phenyl-N-[1'-cyclopropyl-1'-imidazol-2-yl]methyl-hexanamide The compound of Example 61(c) was dissolved in THF (2 mL) and tetrabutyl ammonium fluoride (200 mL, 1M in THF) was added. The reaction was stirred at room temperature overnight and methylene chloride (100 mL) and water (10 mL) were added. The organic layer was dried over potassium carbonate, and the solvent was removed in vacuo to give an oil. Flash chromatography (silica, 5% methanol/methylene chloride) gave a colorless solid which was a 1:1 diastereomeric mixture of the title compound.

EXAMPLE 62

Preparation of (2R,4S,5S,1'R)-5-(t-butoxycarbonyl) amino-4-hydroxy-2-phenylmethyl-6-phenyl-N-[1'-cyclopropyl-1'-imidazol-2-yl]methyl-hexanamide; and (2R,4S,5S,1'S)-5-(t-butoxycarbonyl)amino-4-hydroxy-2-phenylmethyl-6-phenyl-N-[1'-cyclopropyl-1'-imidazol-2-yl]methyl-hexanamide a) Purification of the 125 mg of the compound of Example 61(e) by flash chromatography (silica, 3% methylene chloride/methanol), yielded 48 mg of isomer 1, 15 mg of isomer 2 and 20 mg of combined fractions. $^1$H NMR for isomer 1 (CDCl$_3$, 400 MHz) δ 7.1–7.4 (m, 10H), 6.95 (s, 2H), 6.1 (d, 1H), 4.85 (d, 1H), 4.15 (dd, 1H), 3.75(q, 1H), 3.6(m, 1H), 2.9(dd, 1H), 2.7 (d, 2H), 2.6 (dd, 1H), 2.3 (m, 1H), 2.0 (m, 1H), 1.6 (m, 1H), 1.4 (m, 1H), 1.35 (s, 9H), 0.95 (s, 9H), 0.7 (m, 1H), 0.4 (m, 1H), 0.25 (m, 1H), 0.1 (m, 1H), 0.2 (s, 3H), 0.1 (s, 3H). $^1$H NMR for isomer 2 (CDCl$_3$, 400 MHz) δ 7.1–7.4 (m, 10H), 6.8 (s, 2H), 6.26 (d, 1H), 4.6 (d, 1H), 4.0 (m, 2H), 2.5–3.0 (m, 4H), 1.8 (m, 1H), 1.7 (m, 1H), 1.5 (m, 1H), 1.4 (s, 9H), 1.0 (s, 9H), 0.7 (m, 2H), 0.2 (m, 2H), 0.1 (2 overlapping singlets, 6H).

b) Following the procedure of Example 61(f), except substituting the compounds of Example 62(a) yielded the title compounds. $^1$H NMR for isomer 1 (CD$_3$OD, 400 MHz) δ 7.1–7.3 (m, 10H), 6.95 (s, 2H), 4.25 (d, 1H), 3.5–3.7 (m, 2H), 2.5–3.0 (m, 5H), 1.7 (m, 2H), 1.4 (s, 9H), 1.1 (m, 1H), 0.6 (m, 1H), 0.25–0.4 (m, 2H), 0.05 (m, 1H); MS(ESMS) m/e 533.2 [M+H]$^+$. $^1$H NMR for isomer 2 (CD$_3$OD) δ 7.1–7.4 (m, 10H), 6.85 (s, 2H), 4.25 (d, 1H), 3.5–3.7 (m, 2H), 2.5–2.9 (m, 5H), 1.5–1.8 (m, 2H), 1.4 (s, 9H), 1.1 (m, 1H), 0.2–0.6 (m, 4H); MS(ESMS) m/e 533.4 [M+H]$^+$.

EXAMPLE 63

Preparation of (2R,4S,5S,1'S)-5-((isopropylthiol) carbonyl)-amino-4-hydroxy-2-phenylmethyl-6-phenyl-N-[1-isopropyl-1'-imidazol-2-yl]methyl-hexanamide a) 5-((isopropylthiol)carbonyl)amino-4-(t-butyldimethylsiloxy)-2-phenylmethyl-6-phenyl-N-[1'-isopropyl-1'-(1-(isopropylthiol)carbonyl-imidazol-2yl)] methyl-hexanamide To a solution of (2R,4S,5S,1'S)-5-amino-4-t-butyldimethylsiloxy-2-phenylmethyl-6-phenyl-N-[1'-isopropyl-1'-imidazol-2-yl]methyl-hexanamide (81 mg, 148 mmol) and DMAP (37 mg, 303 mmol) in dichloromethane (8 mL), isopropylthiolchloroformate (42 mg, 0.303 mmol) in dichloromethane (1 mL) was added. The solution was stirred for 20 h and an additional equivalent of the chloroformate and DMAP were added. The reaction mixture was stirred for an additional 20 h, diluted with dichloromethane, and washed with saturated sodium bicarbonate. The organic extract was dried over magnesium sulfate, filtered and evaporated to an oil. The oil was dissolved in chloroform and purified by flash chromatography (silica, 1% methanol/chloroform) to give the title compound as an oil (79.5 mg).

b) (2R,4S,5S,1'S)-5-((isopropylthio)carbonyl)amino-4-hydroxy-2-phenylmethyl-6-phenyl-N-[1-isopropyl-1'-imidazol-2-yl]methyl-hexanamide To a solution of the compound of Example 63(a) (79 mg, 105 mmol) in methanol (8 mL), 10% hydrochloric acid (3 mL) was added. The reaction mixture was stirred overnight at 25° C. The methanol was evaporated in vacuo, and the residue was diluted with water. The solution was neutralized with 5% aqueous sodium carbonate, and a solid precipitated. The solid was filtered, washed with water, and triturated with ether. The solid was dried at high vacuum to yield the title compound (27 mg, 48%). NMR(CDCl$_3$, 250 MHz) $\delta$ 6.9–7.3 (m, 10H), 6.85 (s, 2H), 6.20 (d, 1H), 4.42 (d, 1H), 4.22 (m, 1H), 4.0 (m, 1H), 3.55 (m, 3H), 2.5–3.0 (m, 6H), 1.65 (t, 2H), 1.27 (m, 7H), 0.71 (d of d, 6H); MS(FAB) m/e 537 [M+H]$^+$; TLC R$_f$ 0.30 (silica, 4% methanol/chloroform).

EXAMPLE 64

Preparation of (2R,4S,5S,1'S)5-(1-hydroxymethyl-cyclopentyloxycarbonyl)amino-4-hydroxy-N-(1'-isopropyl-1'-imidazol-2-yl)methyl-6-phenyl-2-phenylmethyl-hexamide a) 1-(t-butyldimethysiloxy)methyl-cyclopentanol To a solution of 1-hydroxymethyl-1-cyclopentanol (4.07 g, 0.035 mole) in dichloromethane (30 mL) t-butyldimethylsilyl chloride (5.28 g, 0.035 mol) in dichloromethane (30 mL) was added. Triethylamine (5.37 mL, 0.0385 mol) and DMAP (0.171 g, 0.0014 mol) were added and the soldtion was stirred overnight at 25° C. The solution was diluted with dichl oromethane (30 mL) and washed with water and saturated ammonium chloride solution. The organic solution was dried over sodium sulfate, filtered and the solvent removed at reduced pressure. The product was purified by flash chromatography (silica, 19:1 hexane:ethyl acetate) to yield the title compound as a colorless oil (6.95 g, 86%).

b) 1-(t-butyldimethylsiloxy)methyl-cyclopentyl 4-nitrophenyl carbonate

A solution of the compound of 64(a) (1.15 g, 5 mmol), DMAP (0.611 g, 5 mmol) and bis (4-nitrophenyl)carbonate (1.52 g, 5 mmol) in dichloromethane (16 mL) was stirred overnight at 25° C. The reaction mixture was diluted with dichloromethane and washed with 5% sodium carbonate. The solvent was removed at reduced pressure and the residual oil was triturated with hexane:ethyl acetate (3:2) and filtered. The product was purified by flash chromatography (silica, 19:1 hexane:ethyl acetate) to give a colorless oil (0.599 g, 30%).

c) (2R,4S,5S,1'S)-5-[1-(t-butyldimethylsiloxy)methyl-cyclopentyloxycarbonyl]amino-4-t-butyldimethylsiloxy-N-[1'-isopropyl-1'-(t-butyldimethylsiloxy)methyl-cyclopentyloxy)imidazol-2-yl]-6-phenyl-2-phenylmethyl-hexanamide A solution of the compound of Example 13(a) (173 mg, 0.316 mmol), DMAP (81 mg, 0.663 mmol) and the compound of Example 64(b) (262 mg, 0.663 mmol) in dichloromethane (10 mL) was stirred for 48 h at 25° C. The organic solution was diluted with dichloromethane, washed with 5% sodium carbonate solution and the solvent removed at reduced pressure. The product was purified by flash chromatography (silica, 4:1hexane:ethyl acetate) to yield the title compound as an oil (200 mg, 60%).

d) (2R,4S,5S,1'S)5-(1-hydroxymethyl-cyclopentyloxycarbonyl)amino-4-hydroxy-N-(1'-isopropyl-1'-imidazol-2-yl)methyl-6-phenyl-2-phenylmethyl-hexamide A solution of the silated derivative (200 mg, 0.188 mmol) in methanol (7 mL) and 3N HCl (2.5 mL) was stirred overnight at 25° C. The methanol was removed at reduced pressure and the solution was diluted with water (15 mL) and extracted with ether (25 mL). The aqueous solution was neutralized with 5% sodium carbonate solution to pH 7–7.5 and the product precipitated as a solid. The solid was filtered, washed with water and dried in vacuo to yield the title compound (51 mg, 47%). NMR (CD$_3$OD, 400 MHz) $\delta$ 7.0–7.3 (m, 10H), 6.87 (s, 2H), 4.62 (d, 1H), 3.70 (m, 3H), 3.55 (d, 1H), 2.5–2.9 (m, 5H), 2.05 (m, 1H), 1.5–2.0 (br, 10H), 0.88 (d, 3H), 0.70 (d, 3H); TLC R$_f$ 0.50 (silica, 8% methanol/chloroform).

EXAMPLE 65

Praparation of (2R,4S,5S,1'S)-5-[3-(R)-(1H-imidazol-2-yl)-3-hydroxy-4-methylpentylamido]-4-hydroxy-N-(1'-isopropyl-1'-imidazol-2-yl)methyl-6-phenyl-2-phenylmethyl-hexanamide; and (2R,4S,5S, 1'S)-5-[3-(S)-(1H-imidazol-2-yl)-3-hydroxy-4-methylpentylamido]-4-hydroxy-N-(1'-isopropyl-1'-imidazol-2-yl)methyl-6-phenyl-2-phenylmethyl-hexanamide a) 1-(1-benzyloxymethylimidazol-2-yl)-2-methyl-1-propanol 1-benzyloxymethylimidazole prepared according to the procedure of Ngochindo, R., J. Chem. Res. (S), 58 (1990)) (3.76 g, 20 mmol), and THF (40 mL) at –40° C., was treated dropwise with n-BuLi (8.4 mL, 21 mmol, 2.5M in hexane). The resulting solution was stirred at –40° C. for 15 min, and i-butyraldehyde (2.0 mL, 22 mmol) was added dropwise. The reaction was stirred at –40° C. for 1.5 h, 0° C. for 1 h, warmed to 23° C., poured into H$_2$O, and extracted with EtOAc. The combined ekhracts were washed with brine, dried (Na$_2$SO$_4$) and concentrated in vacuo. Trituration of the residue with Et$_2$O/hexane gave a white solid which was dried in vacuo overnight to afford of the title compound (3.57 g, 69%). $^1$H NMR(CDCl$_3$, 400 MHz) $\delta$ 7.28 (m, 5H), 6.97 (s, 1H), 6.92 (s, 1H), 5.23 (d, 1H, J=12 Hz), 5.42 (d, 1H, J=12 Hz), 4.48 (s, 2H), 4.44 (d, 1H, J=9 Hz), 2.21 (m, 1H), 1.02 (d, 3H, J=7 Hz), 0.83 (d, 3H, J=7 Hz).

b) 1-(benzyloxymethylimidazol-2-yl)-2-methyl-propan-1-one

The compound of Example 65(a) (1.0 g, 3.88 mmol), MnO$_2$, (1.69 g, 19.4 mmol), and CH$_2$Cl$_2$ (75 mL) were combined and stirred for 1 d. Additional MnO$_2$ (1.69 g, 19.4 mmol) was added and stirring was continued for an additional 2 d. Filtration through Celite®, concentration and flash chromatography (silica, 0–1% CH$_3$OH/CH$_2$Cl$_2$) afforded the title compound (0.773 g, 77%). $^1$H NMR (CDCl$_3$, 400 MHz) 7.28 (m, 6H), 7.18 (s, 1H), 5.85 (s, 2H), 4.52 (s, 2H), 3.94 (m, 1H), 1.21 (d, 2H, J=5 Hz).

c) t-butyl 3-(1-benzyloxymethylimidazol-2-yl)-3-hydroxy-4-methyl-pentanoate

Diisopropylamine (83 µL, 0.59 mmol) and THF (1.5 mL) were cooled to –40° C. and n-BuLi (188 µL, 0.47 mmol, 2.5M in hexane) was added. The reaction mixture was warmed to –10° C. and stirred for 15 m, recooled to –70° C. and t-butyl acetate (63 µL, 0.47 mmol) was added. The reaction was stirred for 5 m. and HMPA (254 µL, 1.41 mmol) was added. The reaction was stirred at –70° C. for 5 m and 1-(benzyloxymethylimidazol-2-yl)-2-methyl-propan- 1-one (100 mg, 0.39 mmol) in THF (1.5 mL) was added dropwise. The mixture was stirred at –70° C. for 30 m, –40° C. for 30 m, –10° C. for 30 m, warmed to 23° C., poured into 10% aqueous $K_2CO_3$ and extracted with EtOAc. The combined organic extracts were washed with brine, dried ($K_2CO_3$), concentrated and flash chromatographed (silica gel, step gradient, 0–20% EtOAc/hexanes) to afford the title compound (131 mg, 90%). $^1$H NMR(CDCl$_3$, 400 MHz) δ 7.25 (m, 5H), 6.96 (s, 1H), 6.91 (s, 1H), 5.69 (d, 1H, J=10 Hz), 5.65 (d, 1H, J=10 Hz), 4.53 (d, 1H, J=11 Hz), 4.48 (d, 1H, J=11 Hz), 3.23 (d, 1H, J=6 Hz), 2.57 (d, 1H, J=6 Hz), 2.14 (m, 1H), 1.39 (s, 9H); 0.97 (d, 3H, J=7 Hz), 0.75 (d, 3H, J=7 Hz); MS(ES) m/e 375 [M+H]$^+$.

d) 3-(1-benzyloxymethylimidazol-2-yl)-3-hydroxy-4-methyl pentanoic acid triflouroacetate.

The compound of Example 65(c) (93 mg, 0.24 mmol) was dissolved in TFA (1 mL) and stirred for 20 m. The TFA was removed in vacuo to give the title compound (102 mg, 100%). $^1$H NMR(CDCl$_3$, 400 MHz) 7.30(m, 7H); 6.06 (d, 1 H, J=9 Hz), 5.74 (d, 1H, J=1 Hz), 4.67 (d, 1H, J=9 Hz), 4.61 (d, 1H, J=9 Hz), 3.62 (d, 1H, J=12 Hz), 2.93 (d, 1H, J=12 Hz), 2.04(m, 1H), 0.92 (d, 3H, J=12 Hz), 0.88 (d, 3H, J=12 Hz); MS(ES) m/e 319 [M+H]$^+$.

e) (2R,4S,5S,1'S)-5-[3-(RS)-(1-benzyloxymethylimidazol-2-yl)-3-hydroxy-4-methylpentanoyl]amino-4-t-butyldimethylsilyloxy-N-(1'-isopropyl-1'-imidazol-2-yl)methyl-6-phenyl-2-phenylmethyl-hexanamide A mixture of the compound of Example 65(d) (1.0 eq) (2R,4S,5S,1'S)-5-amino-4-hydroxy-N-(1'-isopropyl-1'-imidazol-2-yl)methyl-6-phenyl-2-phenylmethyl-hexanamide (1.1 eq), BOP reagent (1.1 eq), and triethylamine (4 eq) were reacted according to the procedure of Example 1(c). The product was purified by flash chromatography to afford the title compound (57%) (silica, step gradient, 0–4% CH$_3$OH/CH$_2$Cl$_2$). $^1$H NMR(CDCl$_3$, 400 MHz) δ 7.36–6.76 (m, 19H), 5.65 (m, 2H), 4.66 (m, ½H), 4.51 (m, 2H), 4.39 (m, ½H), 4.30 (m, ½H), 4.02 (m, ½H), 3.68 (m, 1H), 3.28 (m, 1H), 2.90–2.35 (m, 6H), 2.13 (m, 1H), 1.76 (m, ½H), 1.68 (m, ½H), 1.40 (m, ½H), 1.00–0.70 (m, 21H), 0.10–0.00 (m, 6H); MS(ES) m/e 849 [M+H]$^+$.

f) (2R,4S,5S,1'S)-5-[3-(RS)-(1-benzyloxymethylimidazol-2-yl)-3-hydroxy-4-methylpentanoyl]amino-4-hydroxy-N-(1'-isopropyl-1'-imidazol-2-yl)methyl-6-phenyl-2-phenylmethyl-hexanamide The compound of Example 65(e) (100 mg, 0.12 mmol) was desilylated by the procedure of 47(c) to cleanly afford the title compound (78 mg, 89%). $^1$H NMR(CDCl$_3$, 400 MHz) δ 7.40–6.80 (m, 19H), 5.75 (m, 2H), 4.97 (m, ½H), 4.78 (m, ½H), 4.51 (m, 2H) 3.94 (m, ½H), 3.85 (m, ½H), 3.51 (m, 1H), 3.21 (m, 1H), 2.97–2.43 (m, 6H);2.00 (m, 1H), 1.60 (m, 1H), 1.43 (m, 1H), 0.97–0.49 (m, 12H); MS(ES) m/e 735 [M+H]$^+$.

g) (2R,4S,5S,1'S)-5-[3(R)-(imidazol-2-yl)-3-hydroxy-4-methylpentanoyl]amino-4-hydroxy-N-(1'-isopropyl-1'-imidazol-2-yl)methyl-6-phenyl-2-phenylmethyl-hexanamide; and (2R,4S,5S,1'S)-5-[3-(S)-(imidazol-2-yl)-3-hydroxy-4-methylpentanoyl]amino-4-hydroxy-N-(1'-isopropyl-1'-imidazol-2-yl)methyl-6-phenyl-2-phenylmethyl-hexanamide Using the procedure of Example 47(d), the compound of Example 65(f) (72 mg, 0.98 mmol) was hydrogenated to afford a diastereomeric mixture of the title compounds. The mixture was purified by flash chromatography (silica, step gradient, 0–8% CH$_3$OH/CH$_2$Cl$_2$) to afford tail fractions containing the pure diastereomers (35 mg total, 58%).

Isomer 1, last eluting, (2R,4S,5S,1'S)-5-[3-(R)-(1H-Imidazol-2-yl)-3-hydroxy-4-methylpentylamido]-4-hydroxy-N-(1'-isopropyl-1'-imidazol-2-yl)methyl-6-phenyl-2-phenylmethyl-hexanamide. $^1$H NMR(CDCl$_3$, 400 MHz) δ 7.35–6.82 (m, 10H), 6.93 (s, 1H), 6.84 (s, 1H), 4.42 (d, 1H, J=9 Hz), 3.77 (m, 1H), 3.40 (m, 1H), 3.00–2.40 (m, 5H), 2.14 (m, 1H), 1.99 (m, 1H), 1.56 (m, 1H), 1.47 (m, 1H), 0.93–0.64 (m, 12H); MS (ES) m/e 615 [M+H]$^+$.

Isomer 2, first eluting, (2R,4S,5S,1'S)-5-[3(S)-(1H-Imidazol-2-yl)-3-hydroxy-4-methylpentylamido]-4-hydroxy-N-(1'-isopropyl-1'-imidazol-2-yl)methyl-6-phenyl-2-phenylmethyl-hexanamide. $^1$H NMR(CDCl$_3$, 400 MHz) δ 7.35–6.81 (m, 10H), 6.83 (s,1H), 6.81 (s,1H), 4.46 (d, 1H, J=9 Hz), 3.93 (m, 1H), 3.40 (m, 1H), 3.00–2.40 (m, 5H), 2.13 (m, 1H), 1.91 (m, 1H), 1.41 (m, 1H), 1.10 (m, 1H), 0.93–0.64 (m, 12H); MS (ES) m/e 615 [M+H]$^+$.

EXAMPLE 66

Preparation of (2R,4S,5S,1'S)-5-[(4-methoxyphenoxy)carbonyl]-amino-4-hydroxy-N-(1'-isopropyl-1'-imidazol-2-yl)methyl-6-phenyl-2-phenylmethyl-hexanamide a) (2R,4S,5S,1'S)-5-[(4-methoxyphenoxy)carbonyl]amino-4-t-butyldimethylsiloxy-N-[1'-isopropyl-1'-(N'-methoxycarbonyl)imidazol-2-yl]methyl-6-phenyl-2-phenylmethyl-hexanamide Following the procedure of Example 13(b), except using p-methoxyphenyl chloroformate and (2R,4S,5S,1'S)-5-amino-4-t-butyldimethylsiloxy-N-(1'-isopropyl-1'-imidazol-2-yl)methyl-6-phenyl-2-phenylmethyl-hexanamide (114 mg, 0.21 mmol), the title compound was prepared (63%). NMR(CDCl$_3$), δ 7.44–6.76 (m, 20H), 5.66 (m, 1H), 5.18 (d, 1H), 4.40 (m, 1H), 3.83 (s,3H), 3.76 (m, 1H), 3.73 (s, 3H), 2.96–2.50 (m, 5H), 2.05 (m, 5H), 1.60 (m, 1H), 0.94 (s, 9H), 0.79 (d, 3H, J=7 Hz), 0.74 (s, 3H), 0.12 (s, 3H), 0.11 (s, 3H).

b) (2R,4S,5S,1'S)-5-(methoxycarbonyl)amino-4-hydroxy-N-(1'-isopropyl-1'-imidazol-2-yl)methyl-6-phenyl-2-phenylmethyl-hexanamide Following the procedure of Example 13(c), except using the compound of Example 66(a), the title compound was prepared (32%). NMR(CDCl$_3$/CD$_3$OD), δ 7.36–6.84 (m, 16H), 4.49 (d, 1H, J=9 Hz), 3.79 (s, 3H), 3.37 (m, 1H), 2.92–2.60 (m, 5H), 2.10–1.70 (m, 3H), 0.78 (d, 3H, J=7 Hz), 0.67 (d, 3H, J=7 Hz); MS(ES) m/e 585 [M+H]$^+$.

EXAMPLE 67

Preparation of (2R,4S,5S,1'S)-5-(t-butylaminocarbonyl)amino-4-hydroxy-N-(1'-isopropyl-1'-imldazol-2-yl)methyl-6-phenylmethyl-hexanamide a) (2R,4S,5S,1'S) 5-(t-butylaminocarbonyl)amino-4-(t-butyldimethylsiloxy)-N-(1'-isopropyl-1'-imidazol-2-yl)methyl-6-phenylmethyl-hexamide The compound of Example 13(a) (0.13 g, 0.24 mmol) was dissolved in dichloromethane (3 mL) and t-butyl isocyanate (0.028 g, 0.29 mmol) was added. After stirring at 30° C. for 18 h, the solvent was removed under reduced pressure and the residue was chromatographed (silica, 2:3 ethylacetate:hexane) to give the title compound as a white solid (0.12 g, 77%). NMR(CDCl$_3$), δ 7.35–7.05 (12H, m), 6.85 (2H, s), 4.69 (1H, d, J=9 Hz), 4.60 (1H, t, J=8 Hz), 4.38 (1H, br), 4.24 (1H, q, J=8 Hz), 3.66 (1H, dd, J=4 Hz, 10 Hz), 2.95 (1H, dd, J=9 Hz, 13 Hz), 2.73(2H, m), 2.54 (1H, dd, J=5 Hz, 13 Hz), 2.42 (1H, m), 1.82 (1H, m), 1.67 (1H, m), 1.22 (9H, s), 0.93 (9H, s), 0.84 (3H, d, J=7 Hz), 0.79 (3H, d, J=7 Hz), 0.08 (3H, s), 0.07 (3H, s); MS(ES) m/e 648.4 [M+H]$^+$.

b) (2R,4S,5S,1'S)-5-(t-butylaminocarbonyl)amino-4-hydroxy-N-(1'-isopropyl-1'-imidazol-2-yl)methyl-6-phenylmethyl-hexanamide.

The compound of Example 67(a) (0.033 g, 0.05 mmol) was stirred in dry THF (0.25 mL) and tetrabutylammonium flouride (0.25 mL, 0.25 mmol) in THF was added. After 18 h at 50° C. the reaction was cooled, diluted with ethyl acetate (25 mL), washed with water (5 mL), and dried (MgSO$_4$). The combined organic extracts were filtered and concentrated in vacuo. Chromatography (silica, 1:1 ethyl acetate:hexane) gave the title compound as a white solid (0.018 g, 66%). M.p 226° C. (dec); NMR(CD$_3$OD) δ 7.37–6.90 (10H, m), 6.90 (2H, s), 4.58 (1H, d, J=9 Hz), 3.71 (1H, t, J=7 Hz), 3.52 (1H, d, J=9 Hz), 2.75 (4H, m), 2.53 (1H, dd, J=4 Hz, 12 Hz), 2.03 (1H, m), 1.76 (1H, m), 1.66 (1H, m), 1.22 (9H, s), 0.79 (3H, d, J=7 Hz), 0.67 (3H, d, J=7 Hz); MS(ES) m/e 534 [M+H]$^+$.

EXAMPLE 68

Preparation of (2R,4S,5S,1'S)-5-(methylaminocarbonyl)-amino-4-hydroxy-N-(1'-isopropyl-1'-imidazol-2-yl)methyl-6-phenylmethyl-hexanamide.

Following the procedure of Examples 67(a)–67(b), except substituting methyl isocyanate for t-butylisocyanate, the title compound was prepared (0.075 mg, 51%). Mp 253° C. (dec); NMR(DMSOd$^6$) δ 7.78 (1H, d, J=9 Hz), 7.80–6.96 (11H, m), 6.88 (2H, s), 5.78 (1H, d, J=5 Hz), 5.72 (1H, d, J=9 Hz), 4.84 (1H, d, J=4 Hz), 4.65 (1H, m), 3.68 (1H, q, J=7 Hz), 3.44 (1H, br), 2.74 (3H, m), 2.58 (1H, dd, J=7 Hz, 13 Hz), 2.50 (3H, s), 2.41 (1H, d, J=8 Hz), 1.92 (1H, m), 1.46 (2H, m), 0.72 (3H, d, J=7 Hz), 0.63 (3H, d, J=7 Hz); MS(ES) m/e 492 [M+H]$^+$.

EXAMPLE 69

Preparation of (2R,4S,5S,1'S)-5-(phenylaminocarbonyl)amino-4-hydroxy-N-(1'-isopropyl-1'-imidazol-2-yl)methyl-6-phenylmethyl-hexamide.

Following the procedure of Examples 67(a)–67(b), except substituting phenyl isocyanate for t-butylisocyonate, the title compound was prepared (87 mg, 79%). Mp 273° C. (dec); NMR(DMSO-d$_6$), 8.50 (1H, s), 7.81 (1H, d, J=9 Hz), 7.34–6.83 (18H, m), 6.07 (1H, d, J=9 Hz), 4.99 (1H, d, J=4 Hz), 4.65 (1H, t, J=8 Hz), 3.75 (1H, m), 3.52 (1H, br), 2.77 (3H, m), 2.66 (1H, m), 2.42 (1H, d, J=7 Hz), 1.89 (1H, m), 1.50 (2H, m), 0.68 (3H, d, J=7 Hz), 0.61 (3H, d, J=7 Hz); MS (DCI/NH$_3$) m/e 554.3 [M+H]$^+$.

EXAMPLE 70

(2R,4S,5S,1'S)-5-N-(propylaminocarbonyl)amino-4-hydroxy-N-(1'-isopropyl-1'-imidazol-2-yl)methyl-6-phenylmethyl-hexanamide.

Following the procedure of Examples 67(a), except substituting n-propyl isocyanate for t-butylisocyanate, the title compound was prepared (0.048 g, 54%). Mp 247°–9° C. (dec); NMR(DMSO-d$_6$) δ 7.75 (1H, d, J=8 Hz), 7.23–6.94 (11H, m), 6.85 (2H, s), 5.87 (1H, t, J=5 Hz), 5.65 (1H, d, J=9 Hz), 4.82 (1H, d, J=4 Hz), 4.64 (1H, t, J=8 Hz), 3.66 (1H, m), 3.38 (1H, br), 2.87 (2H, q, J=6 Hz), 2.74 (3H, m), 2.56 (1H, dd, J=7 Hz, 13 Hz), 2.39 (1H, d, J=7 Hz), 1.91 (1H, m), 1.43 (2H, m), 1.28 (2H, q, J=7 Hz), 0.77 (3H, t, J=7 Hz), 0.71 (3H, d, J=7 Hz), 0.62 (3H, d, J=7 Hz); MS(CI) m/e 520.2 [M+H]$^+$.

EXAMPLE 71

Preparation of (2R,4S,5S,1'S)-5-(n-propylaminothiono)amino-4-hydroxy-N-(1'isopropyl-1'-imidazol-2-yl)methyl-6-phenylmethyl-hexamide.

Following the method of Example 67(a)–67(b), except using n-propyl thioisocyanate, the title compound was prepared (0.012 g, 21%). Mp 195–7° C. (dec); NMR (CD$_3$OD) δ 7.32–6.86 (12H, m), 4.59 (1H, m), 3.64 (1H, br), 3.34 (2H, br), 2.79 (5H, m), 2.03 (1H, m), 1.73 (1H, m), 1.58 (3H, m), 0.92 (3H, t, J=7Hz), 0.83 (3H, d, J=7Hz), 0, 68 (3H, d, J=7 Hz); MS (CI) m/e 536.2 [M+H]$^+$.

EXAMPLE 72

Preparation of (2R,4S,5S,1'S)-5-(isopropylaminocarbonyl)-amino-4-hydroxy-N-(1'-isopropyl-1'-imidazol-2-yl)methyl-6-phenylmethyl-hexamide Following the method of Example 67(a)–67(b), except substituting isopropyl isocyanate for t-butyl isocyanate, the title compound was prepared (0.034 g, 46%). NMR(DMSO-d$_6$) δ 7.78 (1H, d, J=8 Hz), 7.24–6.97 (11H, m), 6.85 (2H, s), 5.74 (1H, d, J=8 Hz), 5.57 (1H, d, J=9 Hz), 4.83 (1H, d, J=4 Hz), 4.66 (1H, d, J=7 Hz), 3.62 (2H, m), 3.43 (1H, br), 2.73 (3H, m), 2.57 (1H, dd, J=7 Hz, 13.5 Hz), 2.41 (1H, d, J=7 Hz), 1.91 (1H, m), 1.45 (2H, m), 0.95 (3H, d, J=6.5 Hz), 0.93 (3H, d, J=6.5 Hz), 0.72 (3H, d, J=6.5 Hz), 0.63 (3H, d, J=6.5 Hz); MS (CI) m/e 520.2 [M+H]$^+$.

EXAMPLE 73

Preparation of (2R,4S,5S,1'S)-5-(aminocarbonyl)amino-4-hydroxy-N-(1'-isopropyl-1'-imidazol-2-yl)methyl-6-phenylmethyl-hexamide The compound of Example 67(a) (0.050 g, 0.094 mmol) was dissolved in triflouroacetic acid (2 mL) and stirred at 50° C. for 2 h. After cooling, the reaction mixture was poured into saturated sodium bicarbonate solution (50 mL) and was extracted into ethyl acetate (100 mL). The organic solution was washed with brine, dried (MgSO$_4$) and the solvent removed under reduced pressure. Chromatography of the residue (silica, 19:1 dichloromethane:methanol) gave the title compound as a white solid (0.036 g, 80%). Mp 235° C. (dec); NMR(DMSO) δ 7.82 (1H, d), 7.30–6.90 (11H, m), 6.85 (2H, d), 5.88 (1H, m), 4.86 (1H, d), 4.67 (1H, t), 3.67 (1H, m), 3.45 (1H, m), 2.75 (3H, m), 2.60 (1H, m), 2.43 (1H, m), 1.94 (1H, m), 1, 49 (2H, m), 0.73 (3H, d), 0.62 (3H, d); MS (CI) m/e 478 [M+H]$^+$.

EXAMPLE 74

Preparation of (2R,4S,5S,1'S)-5-(6-quinolinylmethylozy-carbonyl)amino-4-hydroxy-N-(1'-isopropyl-1'-imidazol-2-yl)methyl-6-phenylmethyl-hexanamide Using the procedure of Example 34, except substituting (6-quinolinylmethyl)-(4-nitrophenyl) carbonate for (4-picolinyl)-(4-nitrophenyl) carbonate, the title compound was prepared.

EXAMPLE 75

Preparation of (2R,4S,5S,1'S)-5-(benzoyl)amino-4-hydroxy-N-(1'-isopropyl-1'-imidazol-2-yl)methyl-6-phenylmethyl-hexanamide a) (2R,4S,5S,1'S)-5-benzoyl)amino-4-t-butyldimethylsiloxy-N-(1'-isopropyl-1'-imidazol-2-yl)methyl-6-phenylmethyl-hexamide.

The compound of Example 13(a) (0.11 g, 0.2 mmol), benzoyl chloride (0.025 g, 2.2 mmol) and di(isopropyl)ethylamine (0.026 g, 0.2 mmol) were stirred together in dichloromethane (4 mL) at ambient temperature for 48hr. The solvent was removed under reduced pressure and the residue chromatographed (silica, 1:1 ethyl acetate:hexane) to yield the title compound as a white solid (0.080 g, 61%). NMR(CDCl$_3$)7.53 (2H, d), 7.40–7.04 (11H, m), 6.93 (2H, d), 6.69 (2H, s), 6.59 (1H, d), 6.37 (1H, d), 4.54 (2H, m), 3.68 (1H, t), 2.78 (2H, m), 2.66 (2H, m), 2.39 (1H, dd), 2.13 (1H, m), 1.62 (2H, t), 0.87 (9H, s), 0.53 (3H, d), 0.48 (3H, d), 0.02 (3H, s), 0.00 (3H, s).

b) (2R,4S,5S,1'S)-5-(benzoyl)amino-4-hydroxy-N-(1'-isopropyl-1'-imidazol-2-yl)methyl-6-phenylmethyl-hexanamide The compound of Example 75 (a) (0.080 g, 0.12 mmol) was dissolved in THF (1 mL) and to this was added tetrabutyl-ammomium fluoride, 0.16 mL, 0.16 mmol, 1M solution in THF). After stirring at 40° C. for 24 hr, the solvent was removed under reduced pressure and the residue was chromatographed (silica, step gradient, 1:1 ethyl acetate:hexane, 9:9:2 ethyl acetate:hexane:methanol) to give the title compound as a white solid (0.051 g, 79%). Mp 253–6° C.; NMR(DMSO-d$_6$) δ 7.99 (1H, d), 7.91 (1H, d), 7.72 (2H, d), 7.50–7.02 (13H, m), 6.94 (2H, s), 4.83 (1H, br), 4.68 (1H, d), 4.14 (1H, m), 3.58 (1H, d), 2.82 (4H, m), 2.49 (1H, m), 1.92 (1H, m), 1.73 (1H, t), 1.40 (1H, m), 0.73 (3H, d), 0.63 (3H, d); MS (ES) m/e 539.2 [M+H]$^+$.

EXAMPLE 76

Preparation of (2R,4S,5S,1'S)-5-(2-furylcarbonyl)amino-4-hydroxy-N-(1'-isopropyl-1'-imidazol-2-yl)methyl-6-phenylmethyl-hexanamide Following the procedure of Example 75(a), except using furoyl chloride in place of benzoyl chloride, the title compound was prepared as a white solid (0.019 g, 18%). Mp 212–3° C. (dec); NMR(CDCl$_3$/CD$_3$OD) δ 7.46 (1H, s), 7.30–6.88 (12H, m), 6.85 (2H, s), 6.49 (1H, m), 4.48 (1H, d), 4.20 (1H, m), 3.67 (1H, m), 2.96 (4H, m), 2.77 (2H, m), 2.58 (1H, d), 2.07 (1H, m), 1.71 (2H, m), 0.74 (3H, d), 0.65 (3H, d); MS (ES) m/e 528.32 [M+H]$^+$.

EXAMPLE 77

Preparation of (2R,4S,5S,1'S)-5-(4-methoxybenzoyl)amino-4-hydroxy-N-(1'-isopropyl-1'-imidazol-2-yl)methyl-6-phenylmethyl-hexanamide Following the procedure of Example 75(a), except using 4-methoxybenzoyl chloride in place of benzoyl chloride, the title compound was prepared as a white solid (32%). Mp 235°–7° C. (dec); NMR(CDCl$_3$/CD$_3$OD) δ 7.64 (2H, d), 7.22–6.87 (14H, m), 6.80 (2H, m), 4.52 (1H, d), 4.16 (1H, m), 3.81 (3H, s), 3.62 (1H, d), 2.92 (2H, d), 2.72 (2H, m), 2.53 (1H, dd), 1.98 (1H, m), 1.73 (1H, m), 1.63 (1H, m), 0.71 (3H, d), 0.62 (3H, d); MS (ES) m/e 569.4 [M+H]$^+$.

EXAMPLE 78

Preparation of (2R,4S,5S,1'S)-5-benzylcarbonyl)amino-4-hydroxy-N-(1'-isopropyl-1'-imidazol-2-yl)methyl-6-phenylmethyl-hexamide.

a) (2R,4S,5S,1'S)-5-benzylcarbonyl)amino-4-t-butyldimethylsiloxy-N-(1'-isopropyl-1'-imidazol-2-yl)methyl-6-phenylmethyl-hexanamide.

Following the procedure of Example 75(a), except using phenylacetyl chloride in place of benzoyl chloride and triethylamine in place of di(isopropyl)ethylamine, the title compound was prepared as a white solid (20%). NMR (CDCl$_3$) δ 7.40–6.75 (19H, m), 5.40 (1H, d), 4.73 (1H, t), 4.41 (1H, q), 3.68 (1H, m), 3.48 (2H, s), 2.96 (1H, dd), 2.69 (1H, m), 2.49 (4H, m), 1.61 (2H, m), 0.92 (6H, t), 0.77 (9H, s), 0.04 (3H, s), 0.00 (3H, s).

b) (2R,4S,5S,1'S)-5-benzylcarbonyl)amino-4-hydroxy-N-(1'-isopropyl-1'-imidazol-2-yl)methyl-6-phenylmethyl-hexanamide The product of Example 78(a) (0.018 g, 0.03 mmol) was dissolved in methanol (5 mL) and 2N hydrochloric acid (0.027 mL, 0.06 mmol) was added. After stirring at ambient temperature for 18 h the solvent was removed under reduced pressure and the residue was chromatographed (silica, gradient, dichloromethane/methanol) to yield the title compound (0.011 g, 66%). Mp 240°–2° C.; NMR(CDCl$_3$/CD$_3$OD) δ 7.38–7.06 (18H, m), 6.98 (2H, s), 4.72 (1H, d), 4.14 (1H, m), 3.67 (1H, m), 3, 54 (2H, s), 2.99 (4H, m), 2.67 (1H, m), 2.14 (1H, m), 1.87 (1H, m), 1.63 (1H, m), 0.94 (3H, d), 0.79 (3H, d); MS (ES) m/e 553.2 [M+H]$^+$.

EXAMPLE 79

Preparation of (2R,4S,5S,1'S)-5-(4-hydroxybenzoyl)amino-4-hydroxy-N-(1'-isopropyl -1'-imidazol-2-yl)methyl-6-phenylmethyl-hexanamide a) (2R,4S,5S,1'S)-5-(4-acetoxyphenyl)-4-t-butyldimethylsiloxy-N-(1'-isopropyl-1'-imidazol-2-yl)methyl-6-phenylmethyl-hexanamide.

The compound of Example 13(a) (0.11 g, 0.2 mmol) was dissolved in dichloromethane (2 mL), and BOP reagent (0.089 g, 0.2 mmol), triethylamine (0.028 mL, 0.2 mmol) and 4-acetoxybenzoic acid (0.043 g, 0.24 mmol) were added. After stirring at ambient temperature overnight the solvent was removed under reduced pressure. The residue was chromatographed (silica, 49:1 dichloromethane:methanol) to give the title compound as a white solid (0.11 g, 78%). NMR(CDCl$_3$) δ 7.53 (2H, d), 7.28–6.97 (13H, m), 6.83 (1H, d), 6.78 (2H, s), 6.44 (1H, d), 4.54 (2H, m), 3.72 (1H, dd), 2.79 (4H, m), 2.49 (1H, dd), 2.24 (3H, s), 2.20 (1H, m), 1.70 (2H, m), 0.91 (9H, s), 0.66 (3H, d), 0.57 (3H, d), 0.07 (3H, s), 0.02 (3H, s).

b) (2R,4S,5S,1'S)-5-(4-hydroxybenzoyl)amino-4-t-butyl dimethylsiloxy-N-(1'-isopropyl-1'-imldazol-2-yl)methyl-6-phenylmethyl-hexanamide The product from reaction 79(a) (0.11 g, 0.15 mmol) was dissolved in methanol (5 mL) and powdered potassium carbonate (0.12 g, 0.9 mmol) was added. After stirring the suspension vigorously for 2 h, the mixture was filtered and the solvent removed from the filtrate at reduced pressure. Chromatography of the residue (silica, 19:19:2 ethyl acetate:hexane:methanol) gave the title compound as a white solid (0.066 g, 66%). NMR(CDCl$_3$) δ 7.35 (2H, d), 7.24–6.98 (12H, m), 6.67 (4H, m), 6.32 (1H, d), 4.63 (2H, m), 3.76 (1H, dd), 2.78 (4H, m), 2.44 (1H, d), 2.12 (1H, m), 1.64 (2H, m), 0.88 (9H, s), 0.44 (3H, d), 0.32 (3H, d), 0.05 (3H, s), 0.01 (3H, s).

c) (2R,4S,5S,1'S)-5-(4-hydroxybenzoyl)amino-4-hydroxy-N-(1'-isopropyl-1'-imidazol-2-yl)methyl-6-phenylmethyl-hexanamide Following the procedure of Example 75(b), except using the compound of Example 79(b) in place of the compound of Example 75(a), the title compound was prepared as a white solid (57%). Mp 267°–8° C. (dec); NMR(CDCl₃/CD₃OD) δ 7.57 (2H, d), 7.33–6.75 (17H, m), 4.48 (1H, d), 4.14 (1H, m), 3.58 (1H, d), 2.90 (2H, m), 2.82 (1H, m), 2.73 (1H, m), 2.53 (1H, dd), 2.04 (1H, m), 1.65 (2H, m), 0.73 (3H, d), 0.58 (3H, d); MS (ES) m/e 555.2 [M+H]⁺.

EXAMPLE 80

Preparation of (2R,4S,5S,1'S)-5-(cinnamoyl)amino-4-hydroxy-N-(1'-isopropyl-1'-imidazol-2-yl)methyl-6-phenylmethyl-hexanamide Following the procedure of Example 75 (a), except using cinnamoyl chloride in place of benzoyl chloride, the title compound was prepared as a white solid (25%). Mp 273° C.; NMR(CDCl₃/CD₃OD) δ 7.55–6.91 (19H, m), 6.86 (2H, s), 6.53 (1H, d), 4.37 (1H, d), 4.15 (1H, dt), 3.62 (1H, d), 2.91 (2H, m), 2.78 (2H, m), 2.59 (1H, dd), 2.04 (1H, m), 1.76 (1H, m), 1.65 (1H, m), 0.79 (3H, d), 0.69 (3H, d); MS (ES) m/e 565.2 [M+H]⁺.

EXAMPLE 81

Preparation of (2R,4S,5S,1'S)-5-(2-hydroxybenzoyl)amino-4-hydroxy-N-(1'-isopropyl-1'-imidazol-2-yl)methyl-6-phenylmethyl-hexanamide Following the procedure of Example 79(a), except using 2-acetoxybenzoic acid in place of 4-acetoxybenzoic acid, the title compound was prepared (50%). Mp 197° C.; NMR(CD₃OD) δ 7.77 (1H, d), 7.42–6.78 (17H, m), 4.62 (1H, d), 4.32 (1H, dt), 3.71 (1H, m), 2.94 (2H, m), 2.78 (2H, m), 2.57 (1H, m), 2.03 (1H, m), 1.84 (1H, m), 1.67 (1H, m), 0.82 (3H, d), 0.68 (3H, d); MS (ES) m/e 555.2 [M+H]⁺.

EXAMPLE 82

Preparation of (2R,4S,5S,1'S)-5-(imidazoyl-4-yl-acetyl)amino-4-hydroxy-N-(1'-isopropyl-1'-imidazol-2-yl)methyl-6-phenylmethyl-hexanamide Following the procedure of Example 79(a)–79(c), except using (imidazol-4-yl)acetic acid in place of 4-acetoxy benzoic acid, the title compound was prepared.

EXAMPLE 83

Preparation of (2R,4S,5S,1'S)-5-(t-butoxycarbonyl)amino-4-hydroxy-N-[1'-isopropyl-1'-(4-carbomethoxyethylimidazol-2-yl)]methyl-6-phenyl-2-phenylmethyl-hexanamide a) (1S) 1-carbobenzyloxyamino-1-isopropyl-1-[(4-(E-carbomethoxyethylene)imidazol-2-yl)]methane The compound of Example 27(b) (100 mg, 0.33 mmol), lithium chloride (28 mg, 0.66 mmol) and trimethylphosphonoacetate (61 mg, 0.33 mmol) were dissolved in anhydrous acetonitrile (2 mL). 1,8-Diazabicyclo[5.4.0]-undec-7-ene (55 mg, 0.36 mmol) was added and the reaction mixture was stirred at room temperature overnight. The solvent was removed under reduced pressure and the residue was purified by flash chromatography (silicaa, 2% methanol/dichloromethane to afford the title compound (72 mg, 61%). NMR(CDCl₃) δ 7.60–7.10 (6H, m), 6.50 (1H, br s), 6.10 (1H, br s), 5.15–4.95 (2H, m), 4.50 (1H, br m), 3.75 (3H, s), 2.30 (1H, br m), 1.10–0.80 (6H, m); MS m/e 358.2 [M+H]⁺.

b) (1S)-1-amino-1-isopropyl-1-(4-carbomethoxyethylimidazol-2-yl)methane

Following the procedure of Example 1(b), except substituting the compound of Example 82(a) for the compound of Example 1(a), the title compound was prepared. NMR (CDCl₃) δ 6.65 (1H, s), 4.40 (2H, br s), 3.82 (1H, d, J=3 Hz), 3.65 (3H, s), 2.90–2.55 (4H, m), 2.05 (1H, m), 0.90 (6H, d, J=3 Hz).

c) (2R,4S,5S,1'S)-5-(t-butoxycarbonyl)amino-4-t-butyldimethylsiloxy-N-[1'-isopropyl-1'-(4-carbomethoxyethylimidazol-2yl)]methyl-6-phenyl-2-phenylmethyl-hexanamide Following the procedure of Example 1 (c) except using the compound of Example 82 (b), the title compound was prepared. NMR(CDCl₃) δ 7.35–6.90 (12H, m), 6.55 (1H, s), 4.75 (1H, d, J=4 Hz), 4.45 (1H, m) 3.95 (1H, m), 3.70 (3H, s), 2.90–2.40 (9H, m), 1.90–1.60 (2H, m), 1.38 (9H, s), 0.90–0.70 (15H, m), 0.10 (6H, d, J=2 Hz).

d) (2R,4S,5S,1'S)-5-(t-butoxycarbonyl)amino-4-hydroxy-N-[1'-isopropyl-1'-(4-carbomethoxyethylimidazol-2-yl)]methyl-6-phenyl-2-phenylmethyl-hexanamide.

Following the procedure of Example of 9(d) except using the compound of Example 83 (c), the title compound was prepared. NMR(CDCl₃) δ 7.30–6.90 (10H, m), 6.55 (1H, s), 5.00 (1H, d, J=4 Hz), 4.45 (1H, m), 3.70 (3H, s), 2.95–2.50 (9H, m), 2.25 (1H, m), 1.80–1.60 (2H, m), 0.85 (9H, s), 0.70 (6H, d, J=3 Hz); MS m/e 621.4 [M+H]⁺.

EXAMPLE 84

Preparation of (2R,4S,5S,1'S)-5-(t-butoxycarbonyl)amino-4hydroxy-N-[1'-isopropyl-1'-(4-carboxamidoimidazol-2-yl)]methyl-6-phenyl-2-phenylmethyl-hexanamide a) (1S)-1-carbobenzyloxyamino-1-isopropyl-1-[(4-(hydrazinocarbonyl)imidazol-2-yl)]methane Anhydrous hydrazine (47 µL, 1.5 mmol) was added to a solution of the compound of Example 26(b) (100 mg, 0.30 mmol) in anhydrous methanol. The resulting mixture was stirred overnight at room temperature and concentrated under reduced pressure. The residue was partitioned between ethyl acetate and 10% aqueous Na₂CO₃ and the organic extract was dried over Na₂CO₃ and evaporated under reduced pressure. The residue was purified by flash chromatography (silica, 4% methanol/dichloromethane) to afford the title compound (52 mg, 52%). NMR(CD₃OD) δ 7.50 (1H, s), 7.30–7.20 (5H, m), 5.00–4.90 (2H, m), 4.45 (1H, d, J=6 Hz), 2.10 (1H, br m), 0.95–0.75 (6H, m); MS m/e 332.2 [M+H]⁺ b) (1S)-1-carbobenzyloxyamino-1-isopropyl-1-[(4-azidocarbonyl)imidazol-2-yl]methane The compound of Example 83(a) was dissolved in 2N HCl (1 mL) and glacial acetic acid (0.2 mL) and cooled in an ice bath. A solution of sodium nitrite (11 mg, 0.16 mmol) in H₂O (200 µL) was added dropwise. The reaction mixture was stirred for 0.5 h, neutralized with cold concentrated ammonium hydroxide and extracted with ethyl acetate. The organic extract was dried over Na₂CO₃ and the solvent removed in vacuo to yield the title compound (54mg, 100%). NMR(CDCl₃) δ 7.75 (1H, s), 7.35–7.20 (5H, m), 5.20–5.00 (2H, m), 4.62 (1H, br m), 2.60 (1H br m), 1.10–0.80 (6H, m); IR 2123cm⁻¹ (CON₃).

c) (1S)-1-carbobenzyloxyamino-1-isopropyl-1-(4-carboxamidoimidazol-2-yl)methane

The compound of Example 83(b) was dissolved in 2 mL of ethyl acetate and stirred with of concentrated ammonium hydroxide (1 mL) at 0° C. for 0.5 h, then at room temperature overnight. The reaction mixture was diluted with H₂O, extracted with ethyl asolvent was dried over Na₂CO₃. The solvent was removed in vacuo and the residue was purified by flash chromatography (silica, 4% methanol/ dichloromethane) to afford the title compound (50mg, 100%). NMR(CDCl₃) δ 7.45 (1H, s), 7.25–7.10 (5H, m), 5.00–4.85 (2H, m), 4.35 (1H, d, J=3 Hz), 2.00 (1H, br m), 0.90–0.70 (6H, m); MS m/e 317.2 [M+H]⁺.

d) (1S)-1-amino-1-isopropyl-1-(4-carboxamidoimidazol-2-yl)methane.

Following the procedure of Example 1(b), except substituting the compound of Example 83(c) for the compound of Example 1(a), the title compound was prepared. NMR (CDCl₃)

EXAMPLE 85

δ 7.45 (1H, s), 3.47 (1H, d, J=3 Hz), 1.80 (1H, br m), 0.75–0.60 (6H, m).

e) (2R,4S,5S,1'S)-5-(t-butoxycarbonyl)amino-4-t-butyldimethylsiloxy-N-[1'-isopropyl-1'-(4-carboxamidoimidazol-2-yl)]methyl-6-phenyl-2-phenylmethyl-hexanamide Following the procedure of Example 1(c), except using the compound of Example 83 (d), the title compound was prepared. NMR(CDCl₃) δ 7.50 (1H, s), 7.45–6.90 (11H, m), 6.25 (1H, d, J=4 Hz), 4.50 (1H, d, J=6 Hz), 4.10 (1H, br m), 3.60 (1H, m), 2.90–2.40 (5H, m), 1.90 (1H, br m), 1.70–1.50 (2H, br m), 1.35 (9H, s), 0.90 (9H, s), 0.70–0.60 (6H, m), 0.10 (6H, m).

f) (2R,4S,5S,1'S)-5-(t-butoxycarbonyl)amino-4-hydroxy-N-[1'-isopropyl-1'-(4-carboxamidoimidazol-2-yl)]methyl-6-phenyl -2-phenylmethyl-hexanamide Following the procedure of Example 9(d) except using the compound of Example 83(e) the title compound was prepared. NMR(CD₃OD) δ 7.45 (1H, s), 7.25–6.85 (10H, m), 4.50 (1H, d, J=6 Hz), 4.10 (1H, m), 3.60 (1H, m), 2.85–2.50 (5H, m), 2.00 (1H, br m), 1.80–1.50 (2H, m), 1.30 (9H, s), 0.80–0.65 (6H, m); MS m/e 578.2 [M+H]⁺.

Preparation of (2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide a) (2R,4S,5S,1'S)-2-phenylmethyl-4-t-butyldimethyl-siloxy-5-thioureido-6-phenyl-N-(1'-isopropyl-1'-(imidazo-2-yl))methyl-hexanamide A solution of benzoyl isothiocyanate (prepared from ammonium thiocyanate (147 mg, 1.93 mmol) and benzoyl chloride (257 mg, 1.84 mmol) in of acetone (10 mL) according to the procedure of J. Amer. Chem. Soc., 56, 1408 (1934)) was treated with a solution of (2R,4S,5S,1'S)-2-phenylmethyl-4-t-butyldimethylsiloxy-5-amino-6-phenyl-N-(1'-isopropyl-1'-(imidazo-2-yl))methyl-hexanamide (1.0 g, 1.83 mmol) in acetone. After 20 min at 23° C., the solvent was evaporated, and the residue was dissolved in diethyl ether. The ether extract was washed with water, dried, and the solvent was evaporated. This residue was dissolved in of MeOH (25 mL), treated with 2.5N NaOH (0.1 mL) and heated to 50° C. for 30 min. The solvent was evaporated, and the residue was dissolved in EtOAc. The organic solution was washed with water, dried, and the solvent evaporated. The residue was chromatographed (silica, 5% MeOH/CHCl₃) to yield the title compound (520 mg, 47%). NMR (DMSO) δ 7.80 (1H, d), 7.35 (1H, d), 6.70–7.20 (15H, m), 4.69 (1H, t), 4.54 (1H, m), 3.78 (1H, m), 2.72–2.86 (3H, m), 2.54 (1h, dd), 2.42 (1H, dd), 2.04 (1H, m), 1.82 (1H, m), 1.30 (1H, m), 0.92 (9H, s), 0.86 (3H, d), 0.74 (3H, d), 0.15 (6H, d).

b) dimethylformamidino derivative of (2R,4S,5S,1'S)-2-phenylmethyl-4-dimethyl-t-butyl silyloxy-5-thioureido-6-phenyl-N-(1'-isopropyl-1'-(imidazo-2-yl))methyl-hexanamide A solution of the compound of Example 85(a) (122 mg, 0.2 mmol) and dimethylformamide dimethylacetal (26 mg, 0.22 mmol) in CHCl₃ (2 mL) was stirred at 23° C. for 16 h. The solvent and excess reactant was removed under high vacuum, and the residue was chromatographed (Florisil®, 2% MeOH/CHCL₃) to yield the title compound (100 mg, 76%). NMR(CDCl₃) δ 8.82 (1H, s), 7.05–7.40 (12H, m), 6.76 (1H, br s), 6.60 (1H, d), 5.32 (1H, m), 4.66 (1H, dd), 3.88 (1H, dd), 3.14 (3H, s), 3.05 (3H, s), 2.70–3.04 (4H, m), 2.40 (2H, m), 1.68 (2H, m), 1.00 (9H, s), 0.80 (6H, dd), 0.14 (6H, d).

c). (2R,4S,5S,1'S)-2-phenylmethyl-4-dimethyl-t-butyl silyloxy-5-(5-(1-oxopropyl)-2-thiazolyl)amino)-6-phenyl-N-(1'-isopropyl-1'-(imidazo-2-yl))methyl-hexanamide A solution of the compound of Example 85(b) (1 00 mg, 0.15 mmol), 1-bromo-2-butanone (25 mg, 0.165 mmol), and triethylamine (33 mg, 0.165 mmol) in acetonitrile (10 mL) was heated at 80° C. for 3.5 h. The solvent was evaporated, and the residue shaken with a mixture of diethyl ether and aqueous NaHCO₃. The ether was seperated, washed with water, dried, and the solvent was evaporated. The residue was recrystallized from a mixture of CHCl₃ and hexane to yield the title compound (59 mg, 57%). NMR(CDCl₃) δ 7.75 (1H, s), 7.02–7.38 (10H, m), 6.88 (2H, m), 6.80 (1H, br s), 6.70 (1H, d), 6.60 (1H, d), 4.62 (1H, t), 3.96 (1H, m), 3.78 (1H, t), 2.82 (3H, m), 2.72 (2H, q), 2.54 (2H, m), 2.20 (1H, m), 2.04 (1H, m), 1.66 (1H, m), 1.15 (3H, t), 0.96 (9H, s), 0.72 (6H, t), 0.10 (6H, d).

d). (2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide A solution of the compound of Example 85(c) (50 mg, 0.07 mmol) in (2 mL) of THF was treated with) of tetrabutyl-ammonium fluoride (0.2 mL, 1N solution in THF) 58° C. for 1 h. The solvents were evaporated, and the residue dissolved in ether. The ether was washed with water, dried, and the solvent evaporated. The residue was chromatographed (neutral alumina, Activity V, impurities removed with 2% MeOH/EtOAc, product eluted with 5% MeOH/CHCl₃) to yield the title compound (22 mg, 55%). NMR (DMSO) δ 7.75 (1H, s), 7.66 (1H, d), 6.80–7.30 (13H, m), 4.93 (1H, br s), 4.78 (1H, t), 3.78 (1H, m), 3.68 (1H, dd), 3.00 (1H, dd), 2.92 (1H, dd), 2.86 (1H, m), 2.80–2.90 (1H, br), 2.76 (2H, q), 2.56 (2H, m), 2.12 (1H, m), 1.74 (1H, m), 1.69 (1H, m), 1.20 (3H, t), 0.80 (3H, d), 0.73 (3H, d).

EXAMPLE 86

Preparation of (2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide a) (2R,4S,5S,1'S)-2-phenylmethyl-4-dimethyl-t-butyl silyloxy-5-(2-thiazolylamino)-6-phenyl-N-(1'-isopropyl-1'-(imidazo-2-yl))methyl-hexanamide.

The compound of Example 85(a) (50 mg, 0.08 mmol) in CHCl₃ (2 mL) was treated with chloroacetaldehyde (50 mg, 0.64 mmol). After 20 min the solvent and excess reagent were evaporated. The residue was dissolved in EtOAc, washed with aqueous NaHCO₃, dried and the solvent evaporated. The residue was chromatographed (Florisil®, 60% EtOAc/hexane) to yield the title compound (42 mg, 83%). NMR(CDCl₃) δ 7.12–7.30 (10H, m), 7.02 (1H, d), 6.92 (2H, m), 6.82 (1H, br), 6.62 (1H, br), 6.38 (1H, d), 5.86 (1H, br), 4.58 (1H, t), 4.00 (1H, m), 3.86 (1H, m), 2.85 (3H, m), 2.52 (2H, m), 2.26 (1H, m), 2.16 (1H, m), 1.68 (1H, m), 0.98 (9H, s), 0.70 (6H, t), 0.12 (6H, d).

b) (2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide.

Following the procedure of Example 85(d), except substituting the compound of Example 86(a) for the compound of Example 85(c), the title compound was prepared. NMR (CDCl$_3$/DMSO) δ 6.80–7.42 (14H, m), 6.40 (2H, m), 5.18 (1H, br), 4.74 (1H, t), 3.70 (1H, m), 3.62 (1H, m), 3.00 (2H, m), 2.88 (2H, m), 2.58 (1H, m), 2.18 (1H, m), 1.80 (2H, m), 1.72 (6H, dd).

EXAMPLE 87

Preparation of (2R,4S,5S,1'S)-2-phenylmethyl-4-hydroxy-5-(5-propyl-2-thiazolyl)aminol-6-phenyl-N-(1'-isopropyl-1'-(imidazo-2-yl))methyl-hexanamide a) (2R,4S,5S,1'S)-2-phenylmethyl-4-t-butyldimethylsilyloxy-5-(5-propyl-2-thiazolyl)amino)-6-phenyl-N-(1'-isdpropyl-1'-(imidazo-2-yl))methyl-hexanamide.

A solution of the compound of Example 85(a) (120 mg, 0.2 mmol) in CHCl$_3$ (5 mL) was treated with 2-bromovaleraldehyde (100 mg, 0.6 mmol) and warmed to 60° C. for 30 min and 80° C. for 5 min. The solvent and excess reagent were removed under reduced pressure. The residue was dissolved in EtOAc, washed with aqueous K$_2$CO$_3$, dried, and the solvent evaporated. The residue was chromatographed (silica, 3% MeOH/CHCl$_3$) to yield the title compound (55 mg, 41%). NMR(CDCl$_3$) δ 7.10–7.30 (10H, m), 6.88 (2H, m), 6.72 (1H, br), 6.68 (1H, s), 6.60 (1H, br), 5.60 (1H, br), 4.62 (1H, t), 3.94 (1H, m), 3.78 (1H, t), 2.82 (3H, m), 2.50 (4H, m), 2.26 (1H, m), 2.04 (1H, m), 1.66 (1H, m), 1.55 (2H, sextet), 0.94 (9H, s), 0.92 (3H, t), 0.70 (6H, dd), 0.08 (6H, d).

b). (2R,4S, 5S, 1'S)-2-phenylmethyl-4-hydroxy-5-(5-propyl-2-thiazolyl)amino)-6-phenyl-N-(1'-isopropyl-1'-(imidazo-2-yl))methyl-hexanamide.

Following the procedure of Example 85(d), except substituting the compound of Example 87(a) for the compound of Example 85(c), the title compound was prepared. NMR (CDCl$_3$) δ 7.50 (1H, br), 6.90–7.24 (10H, m), 6.78 (2H, s), 6.60 (1H, s), 6.18 (1H, br), 5.76 (1H, br), 4.60 (1H, t), 3.68 (1H, m), 3.52 (1H, m), 3.05 (1H, dd), 2.95 (2H, m), 2.82 (1H, dd), 2.62 (1H, m), 2.58 (2H, t), 2.32 (1H, m), 1.86 (2H, m), 1.60 (2H, sextet), 0.96 (6H, t), 0.75 (6H, dd).

EXAMPLE 88

Preparation of (2R,4S,5S,1'S)-5-nicotinyl)amino-4-hydroxy-N-(1'-isopropyl-1'-imidazol-2-yl)methyl-6-phenylmethyl-hexamide Following the procedure of Example 75(a), except using nicotinoyl chloride in place of benzoyl chloride, the title compound was prepared as a white solid (43%). Mp 233°–4° C. (dec); NMR(CDCl$_3$/CD$_3$OD) δ 8.81 (1H, d), 8.59 (1H, dd), 7.99 (1H, m), 7.35–6.86 (14H, m), 6.79 (2H, s), 4.44 (1H, d), 4.19 (1H, dt), 3.59 (1H, m), 2.90 (2H, d), 2.68 (2H, m), 2.52 (2H, m), 1.96 (1H, m), 1.71 (1H, m), 1.58 (1H, m), 0.70 (3H, d), 0.58 (3H, d); MS(ES) m/e 540.2 [M+H]$^+$.

The above description fully discloses how to make and use the present invention. However, the present invention is not limited to the particular embodiments described hereinabove, but includes all modifications thereof within the scope of the following claims.

What is claimed is:

1. A compound of the formula (I):

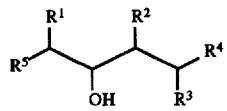

wherein:

R$^1$ and R$^3$ are each independently Q, Q—C$_{1-6}$alkyl, Q—C$_{2-6}$alkenyl, Q—C$_{2-6}$alkynyl or C$_{1-6}$alkyl substituted by one to five fluorine atoms, each optionally substituted by R$^{23}$;

Q is H, C$_{3-6}$cycloalkyl, C$_{5-6}$cycloalkenyl, Ar or Het

R$^2$ is H or OH;

R$^4$ is R$^6$—NR$^{11}$— or CONR$^{11}$CHR$^6$R$^7$;

R$^5$ is R$^6$—NR$^{11}$— or R$^{10}$—NR$^{11}$—;

R$^6$ is

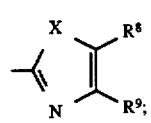

X is NR$^{11}$, O or S;

R$^7$ is Q, Q—C$_{1-6}$alkyl or Q—C$_{2-6}$alkenyl;

R$^8$ and R$^9$ are each independently H, OH, halo, NO$_2$, COR$^{12}$, CF$_3$, Ar, C$_{1-6}$alkyl-R$^{15}$, or R$^{17}$(R$^{18}$R$^{19}$C)$_m$, or together form a fused C$_{2-4}$alkylene, aryl or heteroaryl moiety;

R$^{10}$ is A—(B)$_n$—;

R$^{11}$ is H or C$_{1-4}$alkyl;

R$^{12}$ is R$^7$, OR$^7$, NR$^7$R$^{11}$ or an amino acid or amino alcohol attached via its amino group; B is an amine acid;

A is H, Ar, Het, R$^{17}$(R$^{18}$R$^{19}$C)$_m$, Ar—W, Het—W or R$^{17}$(R$^{18}$R$^{19}$C)$_m$—W, or phthaloyl each optionally substituted by one to three groups chosen from R$^{15}$ or C$_{1-6}$alkyl-R$^{15}$;

W is C=O, OC(=O), NR$^{11}$C(=O), SC(=O), NR$^{11}$C(=S), SO$_2$, NR$^{11}$SO$_2$ or P(=O)(OR$^{22}$);

R$^{15}$ is H, nitro, C$_{1-6}$alkoxy, C$_{1-6}$alkylthio, O(C=O)R$^{16}$, C=OR$^{22}$, CO$_2$R$^{22}$, CON(R$^{16}$)$_2$, N(R$^{22}$)$_2$, NHC(=N) NH—A, I, Br, Cl, F, OR$^{10}$, or OH, provided that when R$^{15}$ is a substituent of the carbon adjacent to W, R$^{15}$ is not halogen or OH when W is OC(=O) or NHCO;

R$^{16}$ is H or C$_{1-6}$alkyl;

R$^{17}$, R$^{18}$ and R$^{19}$ are independently: i) H, R$^{15}$ or C$_{1-4}$alkyl, C$_{2-6}$alkenyl, phenyl, naphthyl, C$_{3-6}$cycloalkyl or Het, each optionally substituted by one to three R$^{15}$ or R$^{15}$-C$_{1-6}$ alkyl groups, or ii) R$^{17}$ is as above and (R$^{18}$R$^{19}$C) are joined together to form a phenyl, naphthyl, C$_{3-6}$cycloalkyl or Het ring, or iii) R$^{17}$ is as above and R$^{18}$ and R$^{19}$ together are =O;

R$^{22}$ is H, C$_{1-6}$alkyl, phenyl or phenyl-C$_{1-4}$alkyl; R$^{23}$ is —X—(CH$_2$)$_q$NR$^{24}$R$^{25}$, X"[((CH$_2$)$_r$O)$_s$]R$^{26}$, CH$_2$X"[(CH$_2$)$_r$O)$_s$]R$^{26}$, or benzofuryl, indolyl, azacycloalkyl, azabicyclo C$_{7-11}$cycloalkyl or benzopiperidinyl, optionally substituted with C$_{1-4}$alkyl;

q is 2–5;

s is 1–6 and r is 1–3 within each repeating unit s;

X' is CH$_2$, O, S or NH;

X" is CH$_2$, NR', O, S, SO or SO$_2$;

$R^{24}$ and $R^{25}$ are i) $C_{1-6}$alkyl, optionally substituted by OH, $C_{1-3}$alkoxy, or $N(R')_2$, ii) the same or different and joined together to form a 5–7 member heterocycle containing up to two additional heteroatoms selected from NR, O, S, SO, $SO_2$, said hererecycle optionally substituted with $C_{1-4}$alkyl, iii) aromatic hererecycle, optionally substituted with $C_{1-4}$alkyl;

R' is H or $C_{1-4}$alkyl;

$R^{26}$ is H, $C_{1-4}$alkyl, $C(=O)R^{27}$, $C(=O)U[(CH_2)_mO]_nR'$, $P(=O)(OM)_2$, $CO_2R^{27}$, $C(=O)NR^{27}R^{28}$, where M is a mono or divalent metal ion, and U is NR' or O;

$R^{27}$ is $C_{1-6}$alkyl or Ar, optionally substituted with one or more hydroxy, carboxy, halo, $C_{1-3}$alkoxy, $CONR'_2$, $NR'_2$, $CO_2R'$, $SO_2NR'_2$, $CH_2NR_2$, NR'COR', NR'$SO_2R'$, $X"[(CH_2)_nO]_nR'$ or $CH_2X"[(CH_2)_nO]_nR'$;

$R^{28}$ is H, $C_{1-6}$alkyl or together with $R^{27}$ forms a 5–7 membered hererecycle or a 6 membered heterocycle containing a heteroatom selected from N, O and S;

Ar is phenyl or naphthyl, optionally substituted with one to three groups chosen from halo, OH, $OR^{10}$, $C_{1-6}$alkyl, $C_{1-6}$alkoxy, $C_{1-6}$alkylthio, $C_{1-6}$alkylamino, $CF_3$, amino, $NO_2$, carboxy, $C_{1-4}$alkylcarbonyl, aminocarbonyl, $C_{1-6}$alkyl-Het, $C_{1-6}$alkoxy-Het, $C_{1-6}$alkyl-phenyl, $C_{1-6}$alkoxy-phenyl, $C_{1-6}$alkyl-, $C_{1-6}$alkoxy-, $HetC_{1-6}$alkyl-,$HetC_{1-6}$alkoxy-, phenyl$C_{1-6}$alkyl-, phenyl$C_{1-6}$alkoxy- or phenyloxy;

Het or heterocycle is a stable 5-to 7-membered monocyclic or a stable 7-to 10-membered bicyclic heterocyclic ring, optionally substituted with one to three halo, OH, alkyl, alkoxy, alkyl-Het, alkoxy-Het, alkyl-phenyl, alkoxy-phenyl, wherein the monocyclic or bicyclic is either saturated or unsaturated, and consists of carbon atoms and from one to three heteroatoms selected from the group consisting of N, O and S, wherein the nitrogen and sulfur heteroatoms may optionally be oxidized, and the nitrogen heteroatom may optionally be quaternized;

m is 1–4; and n is 0 or 1;

or a pharmaceutically acceptable salt thereof.

2. A compound according to claim 1 wherein:

$R^1$ and $R^3$ are $C_{1-6}$alkyl, Ar-$C_{1-6}$alkyl, Ar-$C_{2-6}$alkenyl, Ar-$C_{2-6}$alkynyl, or $C_{1-6}$alkyl optionally substituted by one to five fluorine atoms;

X is N—$R^{11}$;

$R^4$ is $CONR^{11}CHR^6R^7$;

$R^5$ is $R^{10}$—$NR^{11}$;

$R^7$ is H, $C_{1-6}$alkyl, $C_{3-6}$cycloalkyl, phenyl or benzyl;

$R^8$ is H, $C_{1-6}$alkyl, $COR^{12}$, $NO_2$ or Br;

$R^9$ is H, $NO_2$, Br, $COR^{12}$, $CF_3$, Ar, $C_{1-6}$alkyl or $C_{1-6}$alkyl-$R^{15}$, wherein $R^{12}$ is H, $C_{1-6}$alkyl, Ar, $OC_{1-6}$alkyl, $NH_2$, and $R^{15}$ is OH;

A is H, Het, $R^{17}(R^{18}R^{19}C)_m$—W or Het—W;

B is absent or Val;

$R^{17}$, $R^{18}$ and $R^{19}$ are H, or $C_{1-4}$alkyl, Het or Ar, each optionally substituted by one or two $R^{15}$ or $R^{15}C_{1-6}$alkyl groups, or $(R^{18}R^{19}C)$are joined together to form a phenyl, $C_{3-6}$cycloalkyl or Het ring; and W is C=O, OC (=O), NHC (=O), NHC (=S) or SC (=O).

3. A compound according to claim 1 wherein $R^4$ is $CONR^{11}CHR^6R^7$ and X is N—H.

4. A compound according to claim 3 wherein $R^8$ is H and $R^9$ is H or $COR^{12}$.

5. A compound according to claim 4 wherein $R^7$ is $C_{1-6}$alkyl.

6. A compound according to claim 3 wherein $R^1$ is benzyl and $R^3$ is benzyl, 4-hydroxy-benzyl or phenylpropenyl.

7. A compound according to claim 3 wherein A is $R^{17}(R^{18}R^{19}C)_m$—W, and $R^{17}$, $R^{18}$ and $R^{19}$ are H, or $C_{1-4}$alkyl, Het or Ar.

8. A compound according to claim 3 wherein B is absent and A is $C_{1-6}$alkylOC(=O).

9. A compound according to claim 3 wherein W is C=O.

10. A compound according to claim 1 wherein the compound is:

(2R,4S,5S,1'S)-2-phenylmethyl-4-hydroxy-5-(t-butoxycarbonyl)-amino-6-phenyl-N-(1'-isopropyl-1'-(imidazo-2-yl))methyl-hexanamide hydrochloride;

(2R,4S,5S,1'S)-2-phenylmethyl-4-hydroxy-5-(t-butoxycarbonyl)-amino-6-phenyl-N-[1'-isopropyl-1'-(4-aminocarbonyl-thiazo-2-yl)]methyl-hexanamide;

(2R,4S,5S,1'S)-2-phenylmethyl-4-hydroxy-5-(t-butoxycarbonyl)-amino-6-phenyl-N-[1'-isopropyl-1'-(thiazo-2-yl)]methyl-hexanamide;

(2R,4S,5S,1'S)-2-phenylmethyl-4-hydroxy-5-(t-butoxycarbonyl)-amino-6-phenyl-N-(1'-imidazo-2-yl) methyl-hexanamide hydrochloride;

(2R,4S,5S,1'S)-2-phenylmethyl-4-hydroxy-5-(t-butoxycarbonyl)-amino-6-phenyl-N-[1'-methyl-1'-(imidazo-2-yl)]methyl-hexanamide hydrochloride;

(2R,4S,5S,1'S)-2-phenylmethyl-4-hydroxy-5-(t-butoxycarbonyl)-amino-6-phenyl-N-[1'-benzyl-1'-(imidazo-2-yl)]methyl-hexanamide hydrochloride;

(2R,4S,5S,1'S)-5-(carbobenzyloxy)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4,5-dimethyl)imidazol-2-yl]methyl-6-phenyl-2-phenylmethyl-hexanamide;

(2R,4S,5S,1'S)-5-(t-butoxycarbonyl)amino-4-hydroxy-N-[1'-isopropyl-1'-(N'-methyl)imidazol-2-yl]methyl-6-phenyl-2-phenylmethyl-hexanamide;

(2R,4S,5S,1'S)-5-(t-butoxycarbonyl)amino-4-hydroxy-N-(1'-isopropyl-1'-imidazol-2-yl)methyl-6-phenyl-2-(3-phenylpropargyl)hexanamide;

(2R,4S,5S,1'S)-5-(isopropoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(benzyloxyethoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(methoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(ethoxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-(1'-isopropyl-1'-imidazol-2-yl)methyl-6-phenyl-2-(3-phenyl-2-propenyl)hexanamide;

(2R,4S,5S,1'S)-5-(t-butoxycarbonyl)amino-4-hydroxy-N-[1'-isopropyl-1'-(4-nitroimidazol-2-yl)]methyl-6-phenyl-2-phenylmethyl-hexanamide;

(2R,4S,5S,1'S)-5-(t-butoxycarbonyl)amino-4-hydroxy-N-(1'-ethyl-1'-imidazol-2-yl)methyl-6-phenyl-2-phenylmethyl-hexanamide;

(2R,4S,5S,1'S)-5-(t-butoxycarbonyl)amino-4-hydroxy-N-(1'-propyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4-bromoimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4,5-dibromoimidazol-2-yl)]methyl-6-phenyl-2-phenylmethyl-hexanamide;

(2R,4S,5S,1'S)-5-(t-butoxycarbonyl)amino-4-hydroxy-N-1'-isopropyl-1'-(4-methylimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-trifluoromethylimidazol-2-yl)]methyl-6-phenyl-2-phenylmethyl-hexanamide;

(2R,4S,5S,1'S)-5-(t-butoxycarbonyl)amino-4-hydroxy-N-methyl-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4-carbomethoxyimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-methylcarbonylimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-isopropylcarbonyl-imidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-phenylcarbonyl-imidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-formylimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-(hydroxymethyl)-imidazol-2-yl)]methyl-6-phenyl-2-phenylmethyl-hexanamide;

(2R,4S,5S,1'S)-5-((tetrahydrothiopyran-4-yl)oxycarbonyl)-amino-4-hydroxy-N-(1'-isopropyl-1'-imidazol-2-yl)methyl-6-phenyl-2-phenylmethyl-hexanamide;

(2R,4S,5S,1'S)-5-((tetrahydro-4H-pyran-4-yl)oxycarbonyl)-amino-4-hydroxy-N-(1'-isopropyl-1'-imidazol-2-yl)methyl-6-phenyl-2-phenylmethyl-hexanamide;

(2R,4S,5S,1'S)-5-(4-picolinyloxy)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-(1'-isopropyl-1'-imidazol-2-yl)methyl-6-phenyl-2-(4,4,4-trifluorobut-1-yl)hexanamide;

(2R,4S,5S,1'S)-5-(t-butoxycarbonyl)amino-4-hydroxy-N-[1'-isopropyl-1'-(4-((1RS)-1-hydroxyethyl)-imidazol-2-yl)]methyl-6-phenyl-2-phenylmethyl-hexanamide;

(2R,4S,5S,1'S)-5-(t-butoxycarbonyl)amino-4-hydroxy-N-[1'-(1-methyl)propyl-1'-(imidazol-2-yl)]methyl-6-phenyl-2-phenylmethyl-hexanamide;

(2R,4S,5S,1'S)-5-(propylaminocarbonyl)amino-4-hydroxy-N-[1'-isopropyl-1'-(imidazol-2-yl)]methyl-6-phenyl-2-phenylmethyl-hexanamide;

(2R,4S,5S,1'S)-5-(4-hydroxybutanoyl)amino-4-hydroxy-N-(1'-isopropyi-1'-imidazol-2-yl)methyl-6-phenyl-2-phenylmethylhexanamide;

(2R,4S,5S,1'S)-2-phenylmethyl-4-hydroxy-5-(benzyloxy-carbonyl)valylamino-6-phenyl-N-(1'-isobutyl-1'-imidazo-2-yl)methyl-hexanamide;

(2R,4S,5S,1'S)-2-phenylmethyl-4-hydroxy-5-(N-acetylvalyl)-amino-6-phenyl -N-(1'-isobutyl-1'-imidazo-2-yl)methyl-hexanamide;

(2R,4S,5S,1'S)-5-[(imidazol-2-yl)methyloxycarbonyl]amino-4-hydroxy-N-(1'-isopropyl-1'-imidazol-2-yl)methyl-6-phenyl-2-phenylmethyl-hexanamide;

(2R,4S,5S,1'S,1"RS)-5-((1"-(imidazol-2-yl)-2"-methyl)-propyloxycarbonyl)amino-4-hydroxy-N-(1'-isopropyl-1'-imidazol-2-yl)methyl-6-phenyl-2-phenylmethyl-hexanamide;

(2R,4S,5S,1'S)-5-(t-butoxycarbonyl)amino-4-hydroxy-N-[1'-isopropyl-1'-(4-(imidazol-2-yl)imidazol-2-yl)]methyl-6-phenyl-2-phenylmethyl-hexanamide;

(2R,4S,5S,1'S)-5-(1-oxo-thian-4-yl)oxycarbonyl)amino-4-hydroxy-N-(1'-isopropyl-1'-imidazol-2-yl)methyl-6-phenyl-2-phenylmethylhexanamide;

(2R,4S,5S,1'S)-5-((tetrahydrosulfonylpyran-4-yl)oxycarbonyl)amino-4-hydroxy-N-(1'-isopropyl-1'-imidazol-2-yl)methyl-6-phenyl-2-phenylmethylhexanamide;

(2R,4S,5S,1'S)-5-((1,1-dimethyl-2-(benzyloxycarbonyl-glycyloxy)ethoxycarbonyl)amino-4-hydroxy-N-(1'-isopropyl-1'-imidazol-2-yl)methyl-6-phenyl-2-phenylmethyl-hexanamide hydrochloride salt;

(2R,4S,5S,1'S)-5-((1,1-dimethyl-2-glycyloxy)ethoxycarbonyl)-amino-4-hydroxy-N-(1'-isopropyl-1'-imidazol-2-yl)methyl-6-phenyl-2-phenylmethyl-hexanamidedihydrochloridesalt;

(2R,4S,5S,1'S)-5-((1-acetyl)amino-4-hydroxy-N-(1'-isopropyl-1'-imidazol-2-yl)methyl-6-phenyl-2-phenylmethylhexanamide;

(2R,4S,5S,1'S)-5-(t-butoxycarbonyl)amino-4-hydroxy-N-(1'-isopropyl-1'imidazol-2-yl)methyl-6-phenyl-2-(4-benzyloxyphenylmethyl)hexanamide;

(2R,4S,5S,1'S)-5-(t-butoxycarbonyl)amino-4-hydroxy-N-(1'-isopropyl-1'imidazol-2-yl)methyl-6-phenyl-2-(4-hydroxyphenylmethyl)hexanamide;

(2R,4S,5S)-5-(t-butoxycarbonyl)amino-4-hydroxy-2-phenylmethyl-6-phenyl-N-[1'-cyclopropyl-1'-imidazol-2-yl]methyl-hexanamide;

(2R,4S,5S,1'S)-5-((isopropylthiol)carbonyl)-amino-4-hydroxy-2-phenylmethyl-6-phenyl-N-[1-isopropyl-1'-imidazol-2-yl]methyl-hexanamide;

(2R,4S,5S,1'S)-5-[3-(1H-imidazol-2-yl)-3-hydroxy-4-methylpentylamido]-4-hydroxy-N-(1'-isopropyl-1'-imidazol-2-yl)methyl-6-phenyl-2-phenylmethyl-hexanamide;

(2R,4S,5S,1'S)-5-[(4-methoxyphenoxy)carbonyl]amino-4-hydroxy-N-(1'isopropyl-1'-imidazol-2-yl)methyl-6-phenyl-2-phenylmethyl-hexanamide;

2R,4S,5S,1'S)-5-(t-butylaminocarbonyl)amino-4-hydroxy-N-(1'-isopropyl-1'-imidazol-2-yl)methyl-6-phenylmethyl-hexanamide;

(2R,4S,5S,1'S)-5-(methylaminocarbonyl)-amino-4-hydroxy-N-(1'-isopropyl-1'-imidazol-2-yl)methyl-6-phenylmethyl-hexanamide;

(2R,4S,5S,1'S)-5-phenylaminocarbonyl)amino-4-hydroxy-N-(1'-isopropyl-1'-imidazol-2-yl)methyl-6-phenylmethyl-hexamide;

(2R,4S,5S,1'S)-5-N-(propylaminocarbonyl)amino-4-hydroxy-N-(1'-isopropyl-1'-imidazol-2-yl)methyl-6-phenylmethyl-hexanamide;

(2R,4S,5S,1'S)-5-(n-propylaminothiono)amino-4-hydroxy-N-(1'isopropyl-1'-imidazol-2-yl)methyl-6-phenylmethyl-hexamide;

2R,4S,5S,1'S)-5-(isopropylaminocarbonyl)-amino-4-hydroxy-N-(1'-isopropyl-1'-imidazol-2-yl)methyl-6-phenylmethyl-hexanamide;

79

(2R,4S,5S,1'S)-5-(aminocarbonyl)amino-4-hydroxy-N-(1'-isopropyl-1'-imidazol-2-yl)methyl-6-phenylmethyl-hexamide;

(2R,4S,5S,1'S)-5-(6-quinolinylmethyloxy-carbonyl)amino-4-hydroxy-N-(1'-isopropyl-1'-imidazol-2-yl)methyl-6-phenylmethyl-hexanamide;

(2R,4S,5S,1'S)-5-(benzoyl)amino-4-hydroxy-N-(1'-isopropyl-1'-imidazol-2-yl)methyl-6-phenylmethyl-hexanamide;

(2R,4S,5S,1'S)-5-(2-furylcarbonyl)amino-4-hydroxy-N-(1'-isopropyl-1'-imidazol-2-yl)methyl-6-phenylmethyl-hexanamide;

(2R,4S,5S,1'S)-5-(4-methoxybenzoyl)amino-4-hydroxy-N-(1'-isopropyl-1-imidazol-2-yl)methyl-6-phenylmethyl-hexanamide;

(2R,4S,5S,1'S)-5-benzylcarbonyl)amino-4-hydroxy-N-(1'-isopropyl-1-imidazol-2-yl)methyl-6-phenylmethyl-hexamide;

(2R,4S,5S,1'S)-5-(4-hydroxybenzoyl)amino-4-hydroxy-N-(1'-isopropyl-1'-imidazol-2-yl)methyl-6-phenylmethyl-hexanamide;

(2R,4S,5S,1'S)-5-(cinnamoyl)amino-4-hydroxy-N-(1'-isopropyl-1'-imidazol-2-yl)methyl-6-phenylmethyl-hexanamide;

(2R,4S,5S,1'S)-5-(2-hydroxybenzoyl)amino-4-hydroxy-N-(1'-isopropyl-1'-imidazol-2-yl)methyl-6-phenylmethyl-hexanamide;

(2R,4S,5S,1'S)-5-(imidazoyl-4-yl-acetyl)amino-4-hydroxy-N-(1'-isopropyl-1'-imidazol-2-yl)methyl-6-phenylmethyl-hexanamide;

(2R,4S,5S,1'S)-5-(t-butoxycarbonyl)amino-4-hydroxy-N-[1'-isopropyl-1'-(4-carbomethoxyethylimidazol-2-yl)]methyl-6-phenyl-2-phenylmethyl-hexanamide;

(2R,4S,5S,1'S)-5-(t-butoxycarbonyl)amino-4-hydroxy-N-[1'-isopropyl-1'-(4-carboxamidoimidazol-2-yl)]methyl-6-phenyl-2-phenylmethyl-hexanamide;

(2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide;

(2R,4S,5S,1'S)-2-phenylmethyl-4-hydroxy-5-(5-(1-oxopropyl)-2-thiazolyl)amino)-6-phenyl-N-(1'-isopropyl-1'-(imidazo-2-yl))methyl-hexanamide;

(2R,4S,5S,1'S)-2-phenylmethyl-4-hydroxy-5-(5-propyl-2-thiazolyl)amino)-6-phenyl-N-(1'-isopropyl-1'-(imidazo-2-yl))methyl-hexanamide; and (2R,4S,5S,1'S)-5-(nicotinyl)amino-4-hydroxy-N-(1'-isopropyl-1'-imidazol-2-yl)methyl-6-phenylmethyl hexamide.

11. A compound according to claim 1 which is (2R,4S,5S,1'S)-5-(t-butoxycarbonyl)amino-4-hydroxy-N-[1'-isopropyl-1'( 4-isopropylcarbonylimidazol-2-yl)]methyl-6-phenyl-2-phenylmethyl-hexanamide.

12. A compound according to claim 1 which is (2R,4S,5S,1'S)-2-phenylmethyl-4-hydroxy-5-(t-butoxycarbonyl)-amino-6-phenyl-N-(1'-isopropyl-1'-(imidazo-2-yl))methyl-hexanamide.

13. A pharmaceutical composition comprising a compound according to claim 1 and a pharmaceutically acceptable carrier.

14. A pharmaceutical formulation comprising a compound according to claim 1 and an oil.

15. A method of treating HIV infection comprising administering an effective amount of a compound according to claim 1.

80

16. A compound of formula:

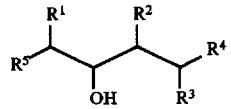

wherein:

$R_1$ and $R_3$ are each independently $C_{1-6}$alkyl, Ar-$C_{1-6}$alkyl, Het—$C_{1-6}$alkyl, $C_{2-6}$alkenyl, Ar-$C_{2-6}$alkenyl, Het—$C_{2-6}$alkenyl, $C_{3-6}$cycloalkyl-$C_{1-6}$alkyl or $C_{3-6}$cycloalkenyl-$C_{1-6}$alkyl;

$R_2$ is H or OH;

$R_4$ is $R_6$—NH—, or

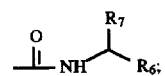

$R_5$ is $R_6$—NH— or $R_{10}$—NH;

$R_6$ is wherein:

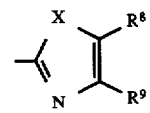

X is $NR_{11}$, O, or S, $R_{11}$ is H or $C_{1-3}$alkyl;

$R_8$ and $R_9$ are each independently H, OH, halo, acyl, or substituted alkyl;

or $R_6$ is

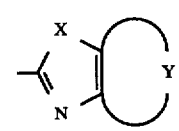

wherein:

X is NH, O, or S;

Y is a fused $C_{2-4}$ alkylene, aryl or heteroaryl moiety;

$R_7$ is $C_{1-6}$alkyl, Ar-$C_{1-6}$alkyl, Het—$C_{1-6}$alkyl, $C_{2-6}$alkenyl, Ar-$C_{2-6}$alkenyl, Het—$C_{2-6}$alkenyl, $C_{3-6}$cycloalkyl-$C_{1-6}$ alkyl or $C_{3-6}$cycloalkenyl-$C_{1-6}$ alkyl;

$R_{10}$ is a moiety A—(B)$_n$—, where n=0 or 1; and B is, independently, an α-amino acid chosen from the group: Ala, Asn, Cys, Trp, Gly, Gln, Ile, Leu, Met, Phe, Pro, Ser, Thr, Tyr, Val, His, or trifluoroalanine, wherein the amino group of B is bonded to A and the carboxy group of B is bonded to the structure;

A is covalently attached to the amino group of the adjacent residue B or to the amino group of the structure if n=0 and is:

1) trityl,
2) hydrogen,
3) $C_{1-6}$alkyl,
4) $R_{14}$—CO— wherein $R_{14}$ is:
   a) hydrogen,
   b) $C_{1-6}$alkyl, unsubstituted or substituted with one or more hydroxyl groups, chlorine atoms, or fluorine atoms,
   c) phenyl or naphthyl unsubstituted or substituted with one or more substituents $R_{15}$ wherein $R_{15}$ is:

81 i) $C_{1-4}$alkyl,
  ii) halogen, where halogen is F, Cl, Br or I,
  iii) hydroxyl,
  iv) nitro,
  v) $C_{1-3}$alkoxy, or
  vi) —CO—N($R_{16}$)$_2$ wherein $R_{16}$ is, independently, H or $C_{1-4}$alkyl; or
  d) a 5–7 member heterocycle such as pyridyl, furyl, or benzisoxazolyl;
5) phthaloyl wherein the aromatic ring is unsubstituted or substituted with one or more substituents $R_{15}$;
6) $R_{17}(R_{18}R_{19}C)_m$-CO— wherein m=1–3 and $R_{17}$, $R_{18}$, and $R_{19}$ are independently:
  a) hydrogen,
  b) chlorine or fluorine,
  c) $C_{1-3}$alkyl unsubstituted or substituted with one or more chlorine or fluorine atoms or hydroxyl groups,
  d) hydroxyl,
  e) phenyl or naphthyl unsubstituted or substituted with one or more substituents $R_{15}$,
  f) $C_{1-3}$alkoxy,
  g) a 5–7 member heterocycle, or
  h) $R_{17}$, $R_{18}$, and $R_{19}$ may be independently joined to form a monocylic, bicyclic, or tricycle ring system each ring of which is $C_{3-6}$ cycloalkyl;
7) $R_{17}(R_{18}R_{19}C)_m$—W— wherein m=1–3 and W is OCO or $SO_2$ and $R_{17}$, $R_{18}$, and $R_{19}$ are as defined above, except $R_{17}$, $R_{18}$, and $R_{19}$ are not chlorine, fluorine or hydroxyl if they are adjacent to W;
8) $R_{20}$—W— wherein $R_{20}$ is a 5–7 member heterocycle such as pyridyl, furyl, or benzisoxazolyl;
9) $R_{21}$—W— wherein $R_{21}$ is phenyl or naphthyl unsubstituted or substituted with one or more subsituents $R_{15}$;
10) $R_{17}$—($R_{18}R_{19}C)_m$—P(0)(O$R_{22}$)— wherein $R_{22}$ is $C_{1-4}$ alkyl or phenyl;
11) $R_{20}$—P O)(O$R_{22}$)—; or
12) $R_{21}$—P(O)(O$R_{22}$)—;

or pharmaceutically acceptable salt thereof.

17. A compound according to claim 1 wherein $R^{10}$ is $C_{1-6}$alkylOC(=O) or $C_{5-6}$cycloalkylOC(=O) substituted by one or two OH or $CH_2OH$ groups.

18. A compound according to claim 17 selected from the group of:

82

(2R,4S,5S,1'S)-5-(1,1-dimethyl-2-hydroxyethoxycarbonyl)amino-4-hydroxy-N-(1'-isopropyl-1'-imidazol-2-yl)methyl-6-phenyl-2-phenylmethyl-hexanamide hydrochloride;

(2R,4S,5S,1'S)-5-(hydroxyethoxycarbonyl)amino-4-hydroxy-N-(1'-isopropyl-1'-imidazol-2-yl)methyl-6-phenyl-2-phenylmethylhexanamide;

(2R,4S,5S,1'S)-5-(2-hydroxy-1-methylethoxycarbonyl)amino-4-hydroxy-N-(1'-isopropyl-1'-imidazol-2-yl)methyl-6-phenyl-2-phenylmethylhexanamide;

(2R,4S,5S,1'S)-5-(2-hydroxy-1-cyclopentyloxycarbonyl)amino-4-hydroxy-N-(1'-isopropyl-1'-imidazol-2-yl)methyl-6-phenyl-2-phenylmethylhexanamide;

(2R,4S,5S,1'S)-5-[di(hydroxymethyl)-methoxycarbonyl]amino-4-hydroxy-N-(1'-isopropyl-1'-imidazol-2-yl)methyl-6-phenyl-2-phenylmethyl-hexanamide;

(2R,4S,5S,1'S)-5-((1,1-dimethyl-2-hydroxy)ethoxycarbonyl)amino-4-hydroxy-N-(1'-isopropyl-1'-(4-isopropylcarbonylimidazol-2-yl))methyl-6-phenyl-2-phenylmethyl-hexanamide dihydrochloride salt;(2R,4S,5S,1'S)-5-((1S)-1-methyl-2-hydroxyethoxycarbonyl)amino-4-hydroxy-N-(1'-isopropyl-1'-imidazol-2-yl)methyl-6-phenyl-2-phenylmethylhexanamide;

(2R,4S,5S,1'S)-5-((1S)-1-methyl-2-hydroxyethoxycarbonyl)amino-4-hydroxy-N-(1'-isopropyl-1'-imidazol-2-yl)methyl-6-phenyl-2-phenylmethylhexanamide;

(2R,4S,5S,1'S)-5-(1-hydroxymethyl-cyclopentyloxycarbonyl)amino-4-hydroxy-N-(1'-isopropyl-1'-imidazol-2-yl)methyl-6-phenyl-2-phenylmethyl-hexamide;

(2R,4S,5S,1'S)-5-[3-(R)-(1H-imidazol-2-yl)-3-hydroxy-4-methylpentylamido]-4-hydroxy-N-(1'-isopropyl-1'-imidazol-2-yl)methyl-6-phenyl-2-phenylmethyl-hexanamide; and (2R,4S,5S,1'S)-5-[3-(S)-(1H-imidazol-2-yl)-3-hydroxy-4-methylpentylamido]-4-hydroxy-N-(1'-isopropyl-1'-imidazol-2-yl)methyl-6-phenyl-2-phenyhnethyl-hexanamide.

* * * * *